(12) United States Patent
Matsunaga et al.

(10) Patent No.: US 12,134,784 B2
(45) Date of Patent: Nov. 5, 2024

(54) METHOD FOR PREPARING INTESTINAL TRACT CELL LAYER DERIVED FROM PLURIPOTENT STEM CELL

(71) Applicant: PUBLIC UNIVERSITY CORPORATION NAGOYA CITY UNIVERSITY, Nagoya (JP)

(72) Inventors: Tamihide Matsunaga, Nagoya-chi (JP); Takahiro Iwao, Nagoya-chi (JP); Daichi Onozato, Nagoya-chi (JP); Isamu Ogawa, Nagoya-chi (JP)

(73) Assignee: PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 750 days.

(21) Appl. No.: 17/290,446

(22) PCT Filed: Oct. 31, 2019

(86) PCT No.: PCT/JP2019/042938
§ 371 (c)(1),
(2) Date: Apr. 30, 2021

(87) PCT Pub. No.: WO2020/091020
PCT Pub. Date: May 7, 2020

(65) Prior Publication Data
US 2022/0033780 A1 Feb. 3, 2022

(30) Foreign Application Priority Data

Nov. 2, 2018 (JP) .................................. 2018-207108
May 15, 2019 (JP) .................................. 2019-092336

(51) Int. Cl.
*C12N 5/071* (2010.01)
*A61L 27/38* (2006.01)
*G01N 33/50* (2006.01)

(52) U.S. Cl.
CPC ........ *C12N 5/0679* (2013.01); *A61L 27/3804* (2013.01); *G01N 33/5014* (2013.01); *G01N 33/5044* (2013.01); *C12N 2501/01* (2013.01); *C12N 2501/11* (2013.01); *C12N 2501/115* (2013.01); *C12N 2501/119* (2013.01); *C12N 2501/15* (2013.01); *C12N 2501/155* (2013.01); *C12N 2501/415* (2013.01); *C12N 2501/727* (2013.01); *C12N 2506/45* (2013.01); *C12N 2533/52* (2013.01)

(58) Field of Classification Search
CPC .............. C12N 5/0679; C12N 2501/01; C12N 2501/11; C12N 2501/115; C12N 2501/119; C12N 2501/15; C12N 2501/155; C12N 2501/415; C12N 2501/727; C12N 2506/45; C12N 2533/52; C12N 2500/32; C12N 2501/16; C12N 2501/72; C12N 2501/734; C12N 2533/70; C12N 2533/90; A61L 27/3804; G01N 33/5014; G01N 33/5044; G01N 33/5082
See application file for complete search history.

(56) References Cited

U.S. PATENT DOCUMENTS

2017/0240866 A1   8/2017   Wells et al.

FOREIGN PATENT DOCUMENTS

| WO | 2017/154795 A1 | 9/2017 |
| WO | 2017/205511 A1 | 11/2017 |
| WO | 2018/151307 A1 | 8/2018 |

OTHER PUBLICATIONS

Fernando et al. A simple, cost-effective method for generating murine colonic 3D enteroids and 2D monolayers for studies of primary epithelial cell function. Am J Physiol Gastrointest Liver Physiol. Nov. 1, 2017;313(5):G467-G475. (Year: 2017).*
Kozuka et al. Development and Characterization of a Human and Mouse Intestinal Epithelial Cell Monolayer Platform. Stem Cell Reports. Dec. 12, 2017;9(6):1976-1990. (Year: 2017).*
DiMarco et al. Engineering of Three-Dimensional Microenvironments to Promote Contractile Behavior in Primary Intestinal Organoids. Integr Biol (Camb). Feb. 2014;6(2):127-142. (Year: 2014).*
Office Action dated Jun. 27, 2023 issued in Japanese Application No. 2020-554968.

(Continued)

Primary Examiner — Marcia S Noble
Assistant Examiner — Briana N Ebbinghaus
(74) Attorney, Agent, or Firm — Sughrue Mion, PLLC

(57) ABSTRACT

An object is to prepare an intestinal organoid having a characteristic close to the small intestine of a living body, from a pluripotent stem cell. An intestinal organoid is prepared from a pluripotent stem cell, by the following steps of: (1) differentiating the pluripotent stem cell into an endoderm-like cell; (2) differentiating the endoderm-like cell obtained in step (1) into an intestinal stem cell-like cell; (3) culturing the intestinal stem cell-like cell obtained in step (2) in the presence of an epidermal growth factor, a fibroblast growth factor, a TGF β receptor inhibitor, a GSK-3 β inhibitor, and a ROCK inhibitor; (4) culturing the cell obtained in step (3) to form a spheroid; and (5) differentiating the spheroid formed in step (4) to form an intestinal organoid, wherein the differentiation includes culturing in the presence of an epidermal growth factor, a BMP inhibitor, and a Wnt signal activator. Also, a plane culture system is prepared by subjecting the cells constituting the intestinal organoid formed in step (5) to plane culture in the presence of an epidermal growth factor and a TGF β receptor inhibitor. A highly functional evaluation system having the villi structure is constructed by using air-liquid interface culture in the plane culture.

6 Claims, 22 Drawing Sheets

(56) References Cited

OTHER PUBLICATIONS

Extended European Search Report dated Jul. 11, 2022 issued in European Application No. 19878058.7.
Liu et al., "Chemical Modulation of Cell Fate in Stem Cell Therapeutics and Regenerative Medicine", Cell Chemical Biology, Aug. 18, 2016, vol. 23, pp. 893-916 (24 pages).
Onozato et al., "Generation of Intestinal Organoids Suitable for Pharmacokinetic Studies from Human Induced Pluripotent Stem Cells", Drug Metab Dispos, Nov. 2018, vol. 46, No. 11, pp. 1572-1580 (13 pages).
Onozato et al., "Efficient Generation of Cynomolgus Monkey Induced Pluripotent Stem Cell-Derived Intestinal Organoids with Pharmacokinetic Functions", Stem Cells and Development, 2018, vol. 27, No. 15, pp. 1033-1045 (13 pages).
Zhang et al., "Human iPSC-Derived Posterior Gut Progenitors Are Expandable and Capable of Forming Gut and Liver Organoids", Stem Cell Reports, Mar. 13, 2018, vol. 10, pp. 780-793 (14 pages).

* cited by examiner

[Fig. 1]
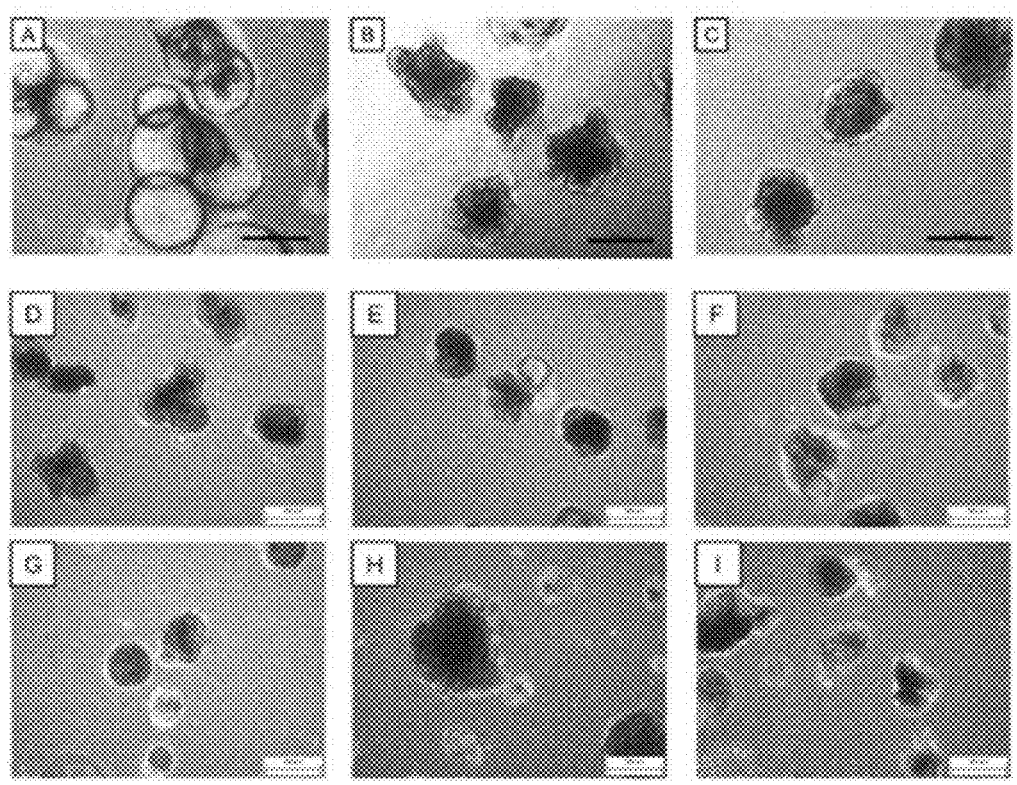

[Fig. 2]
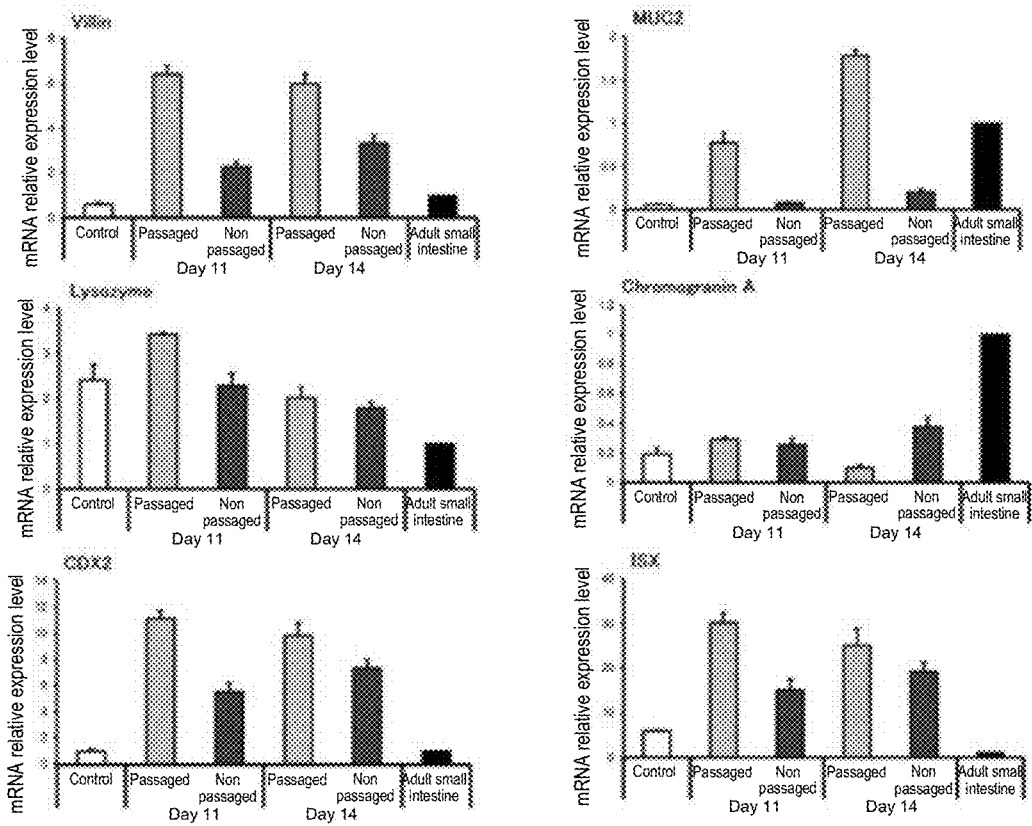

[Fig. 3]
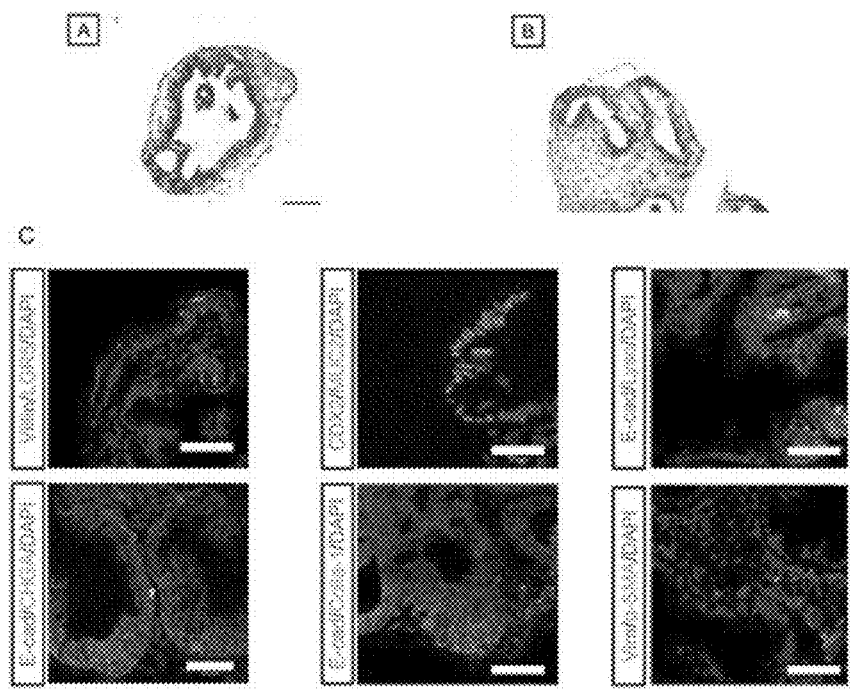

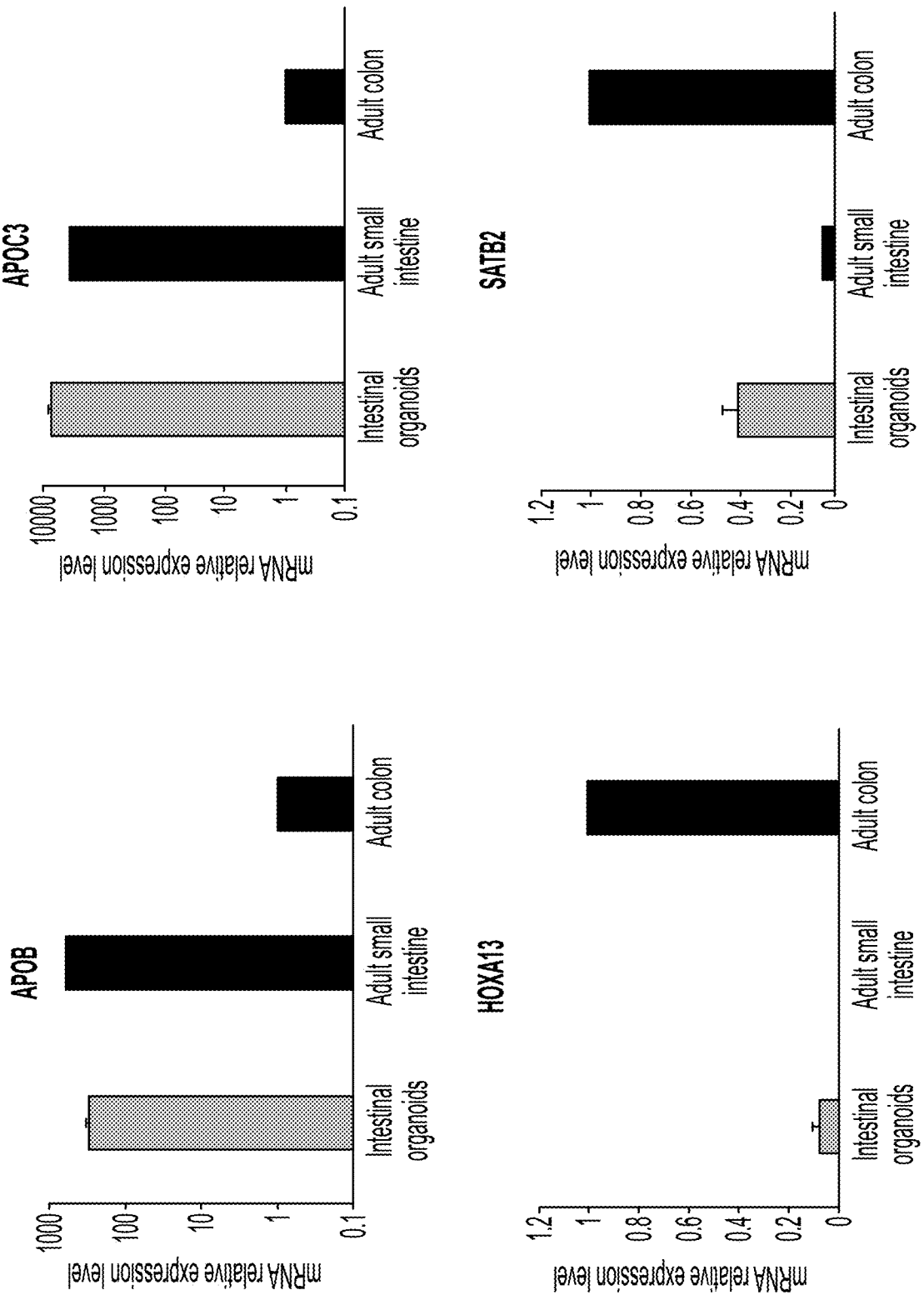
[Fig. 4]

[Fig. 5]
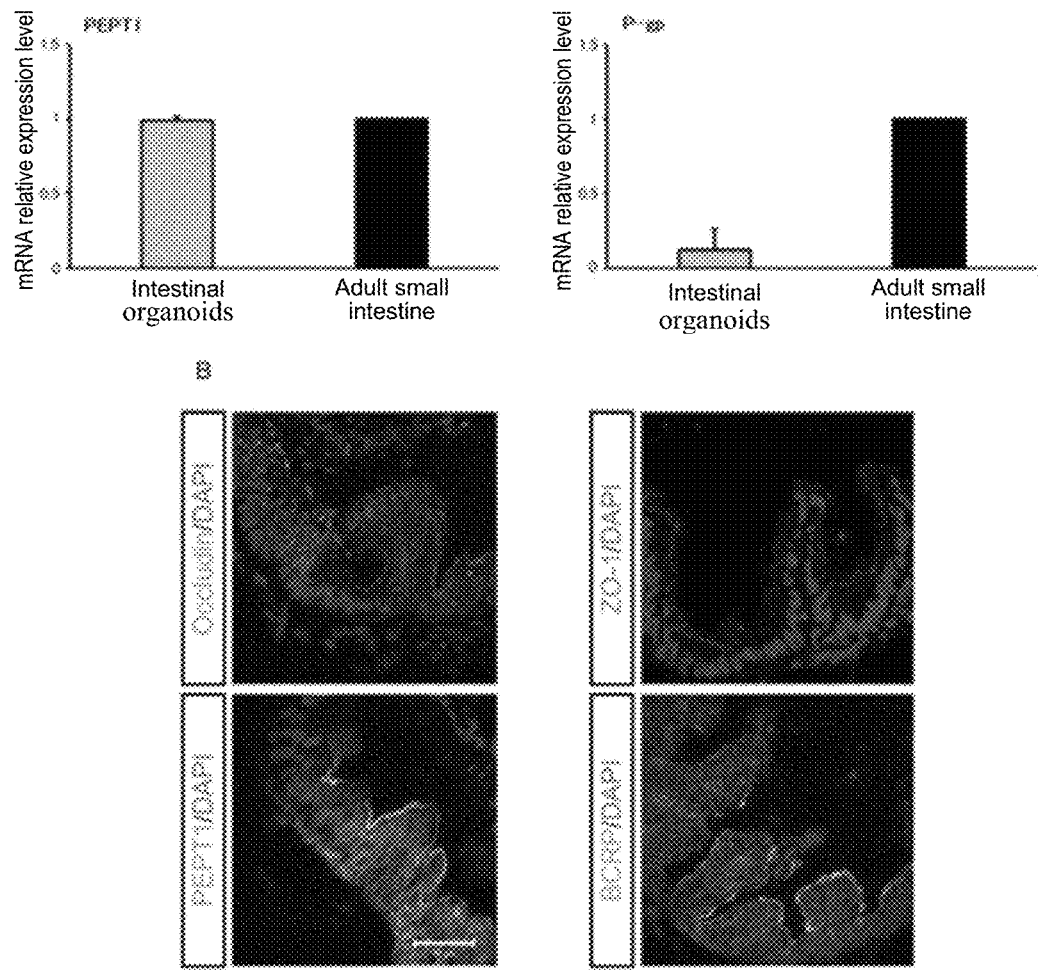

[Fig. 6]
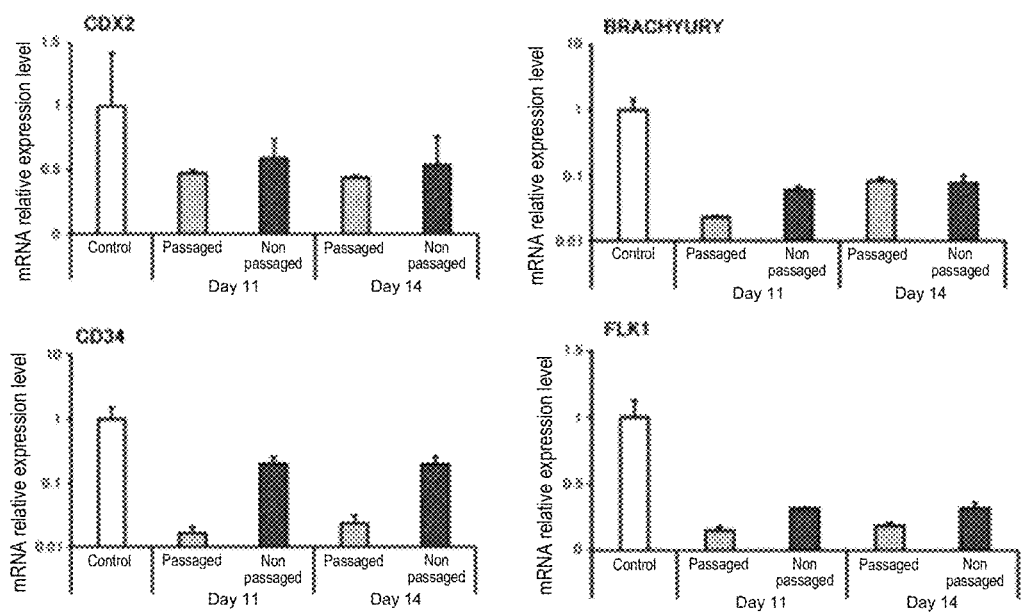

[Fig. 7-1]
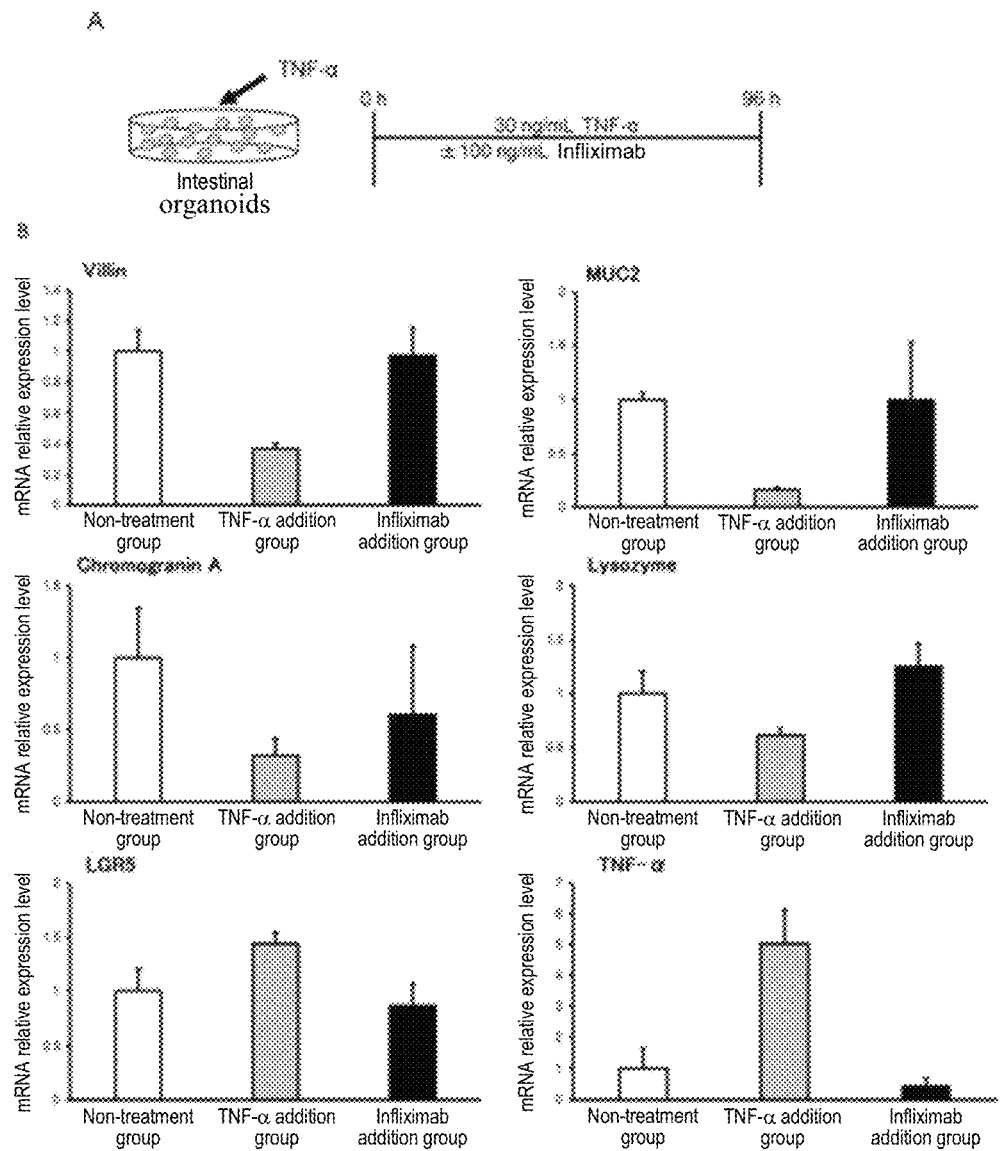

[Fig. 7-2]
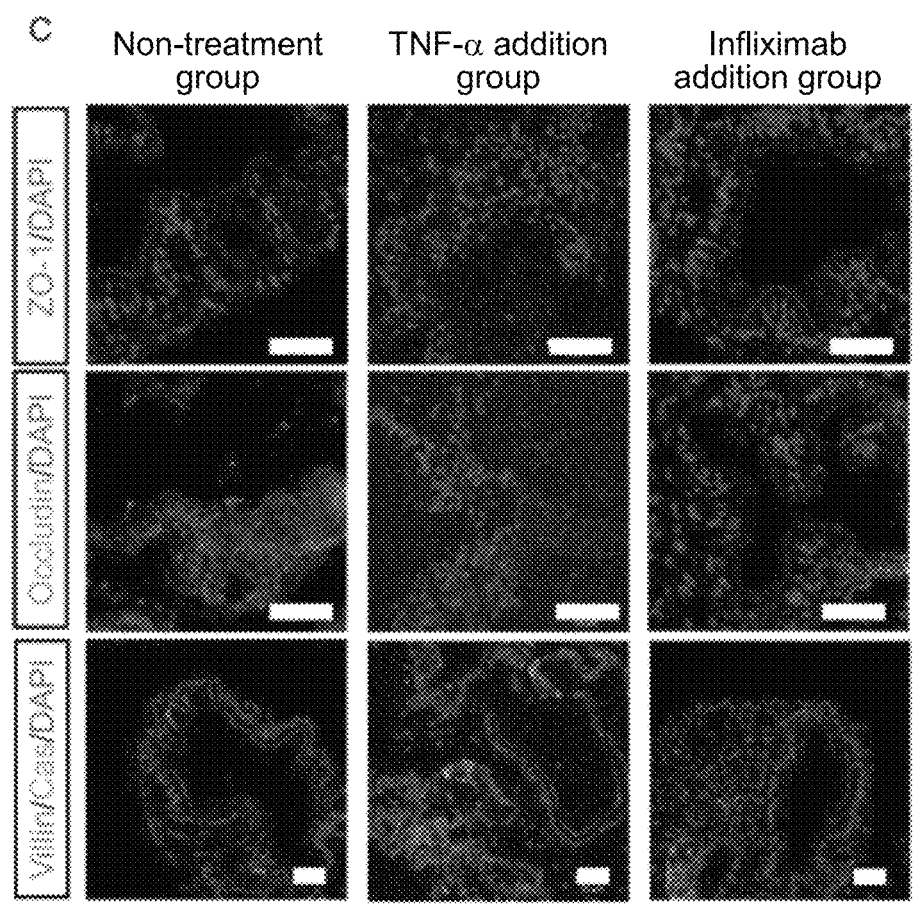

[Fig. 8]
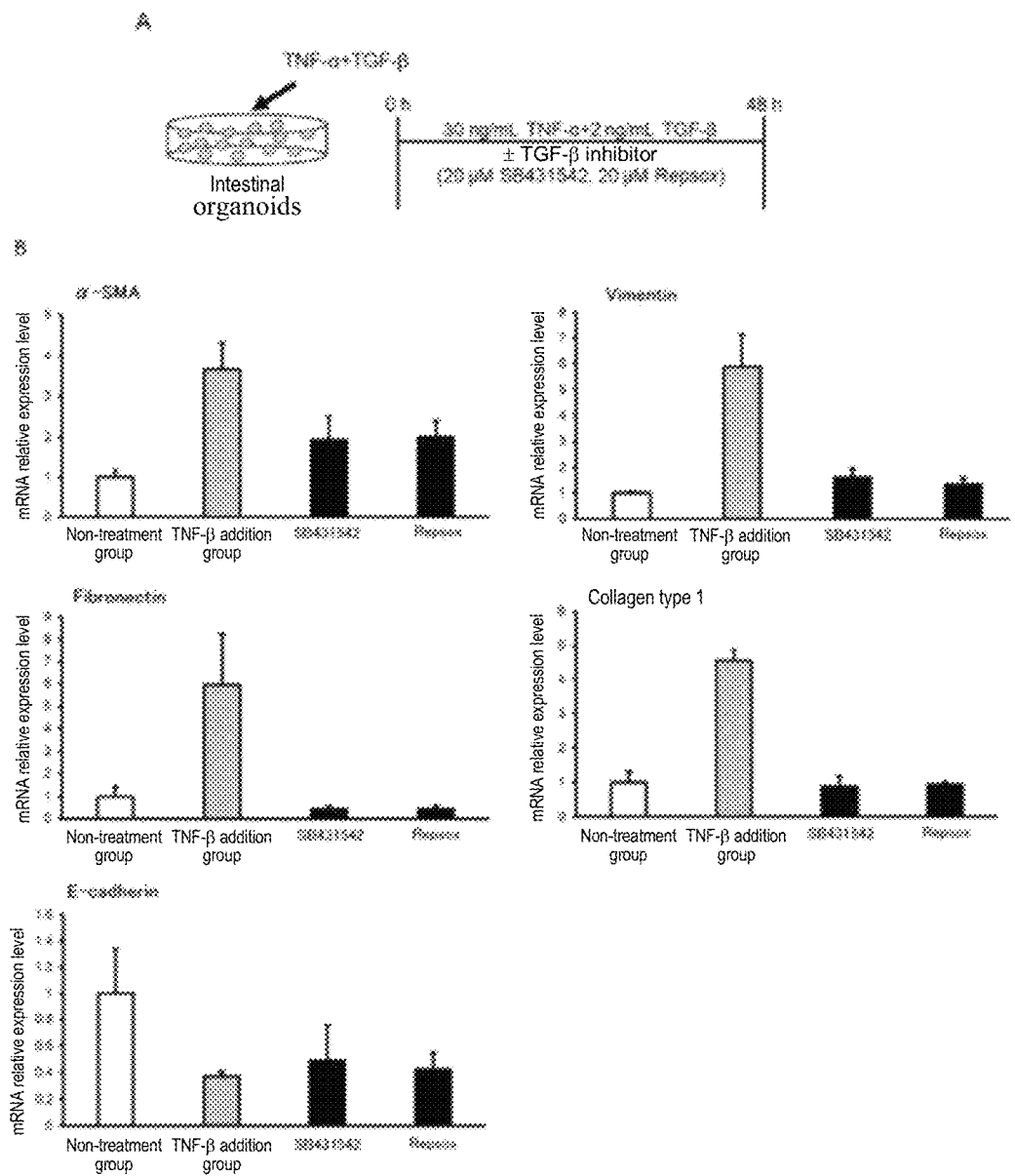

[Fig. 9]
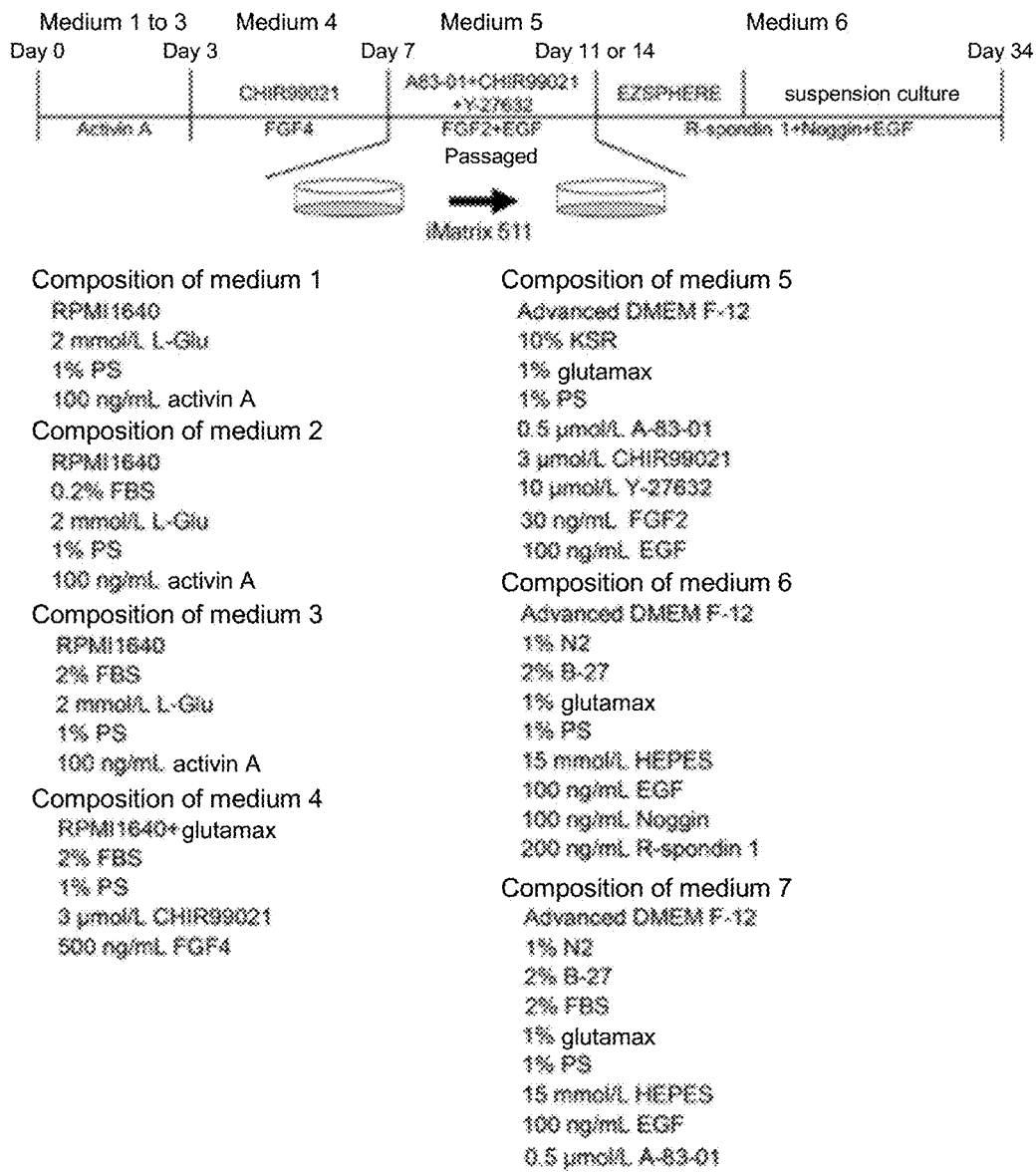

[Fig. 10]
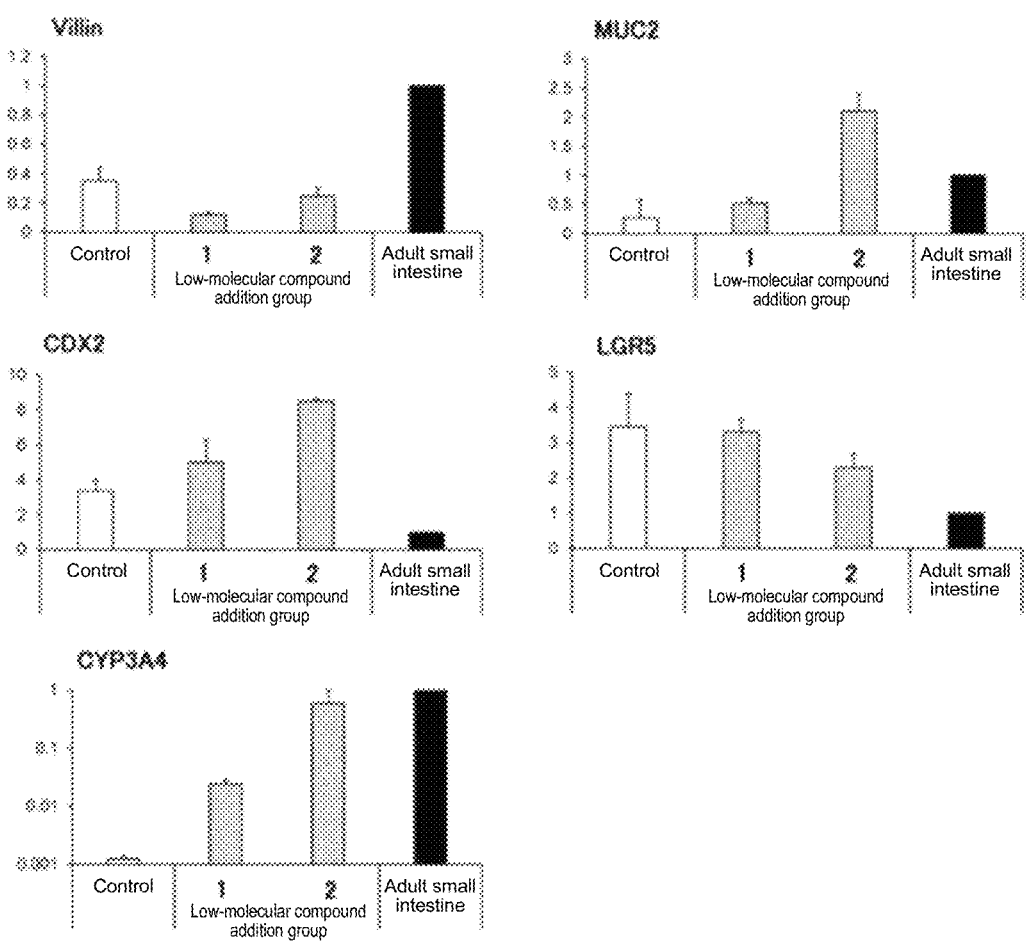

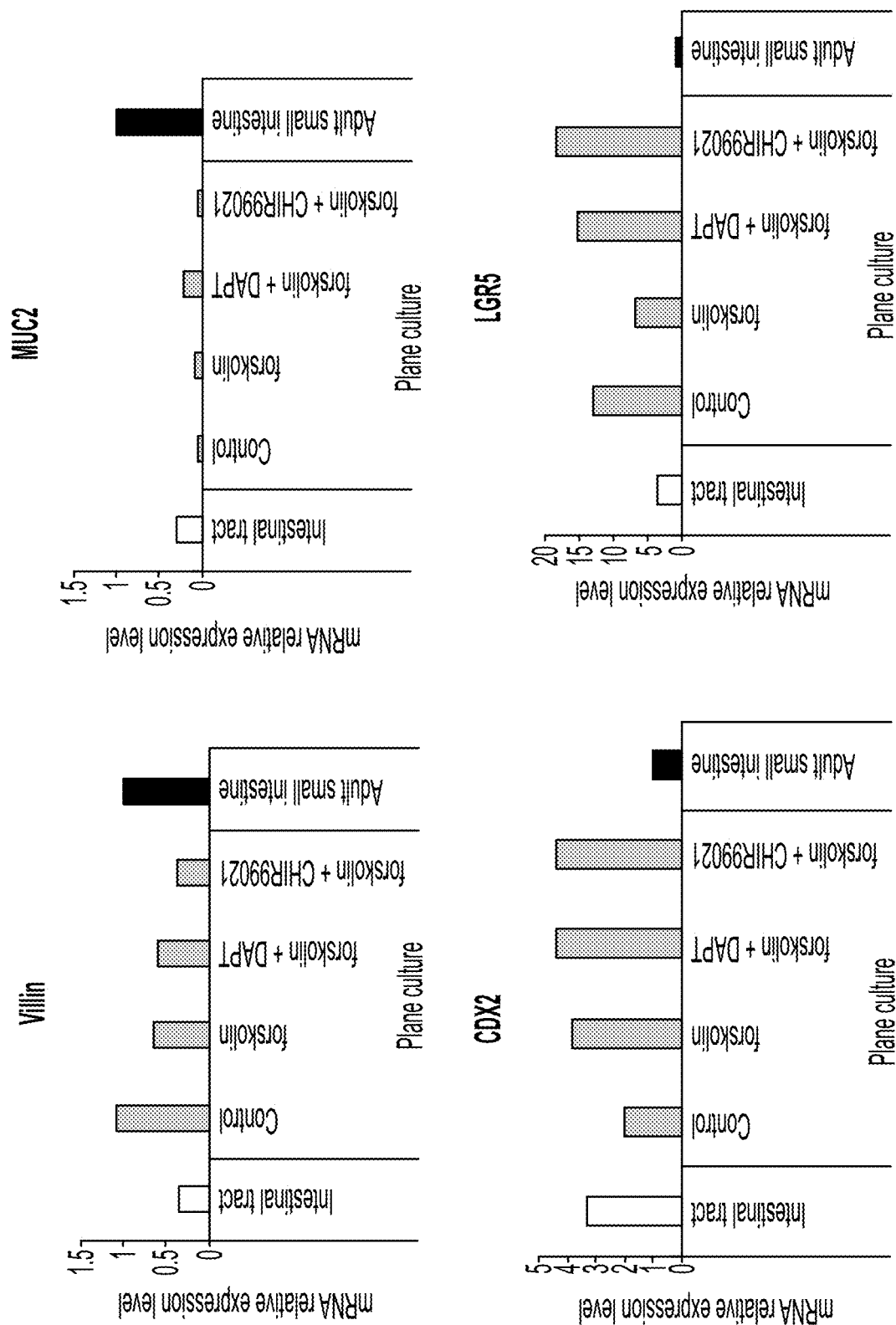
[Fig. 11-1A]

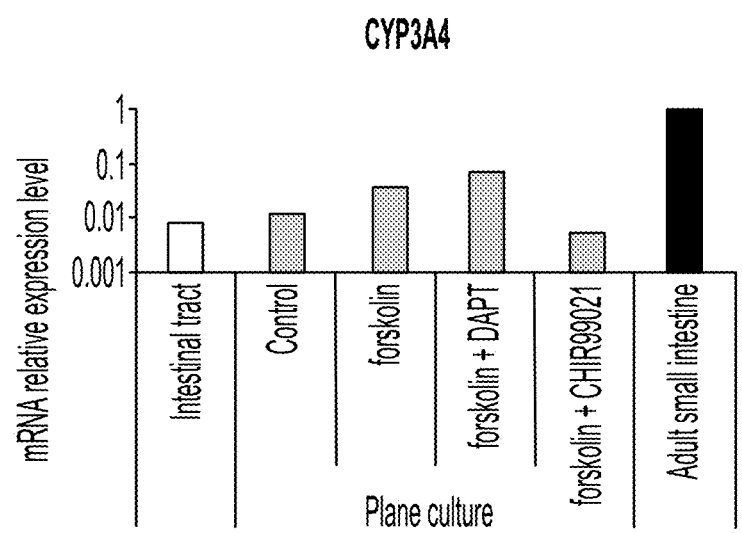
[Fig. 11-1A1]

[Fig. 11-2]
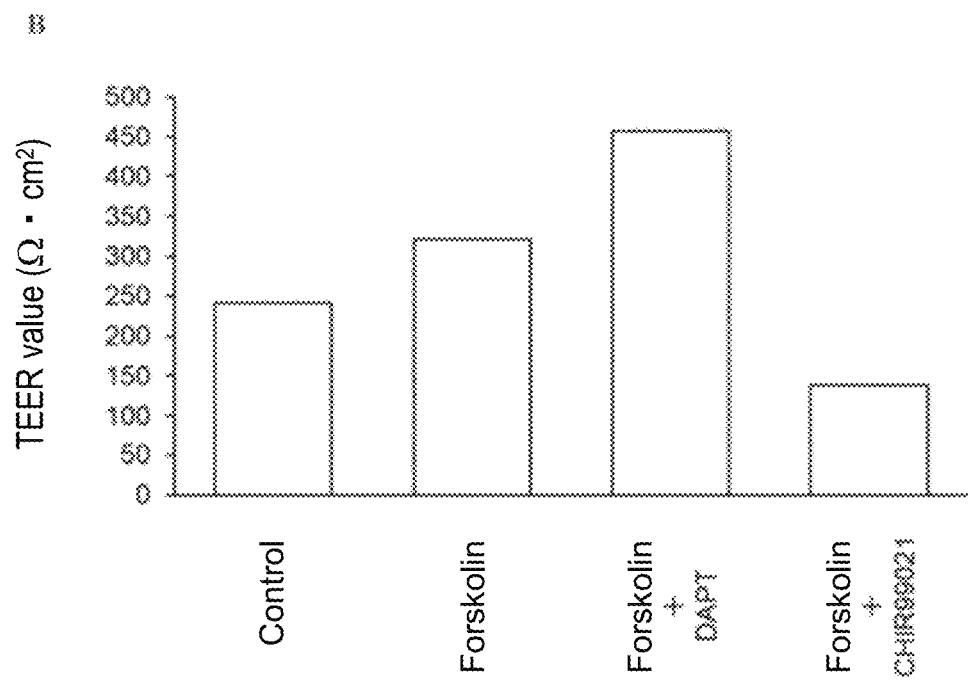
[Fig. 12]
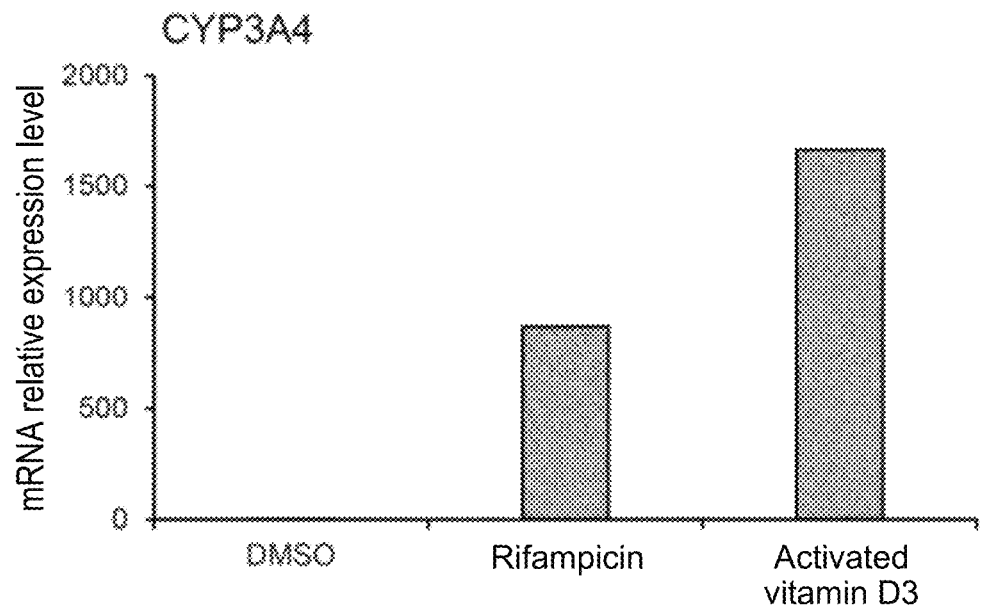

[Fig. 13]
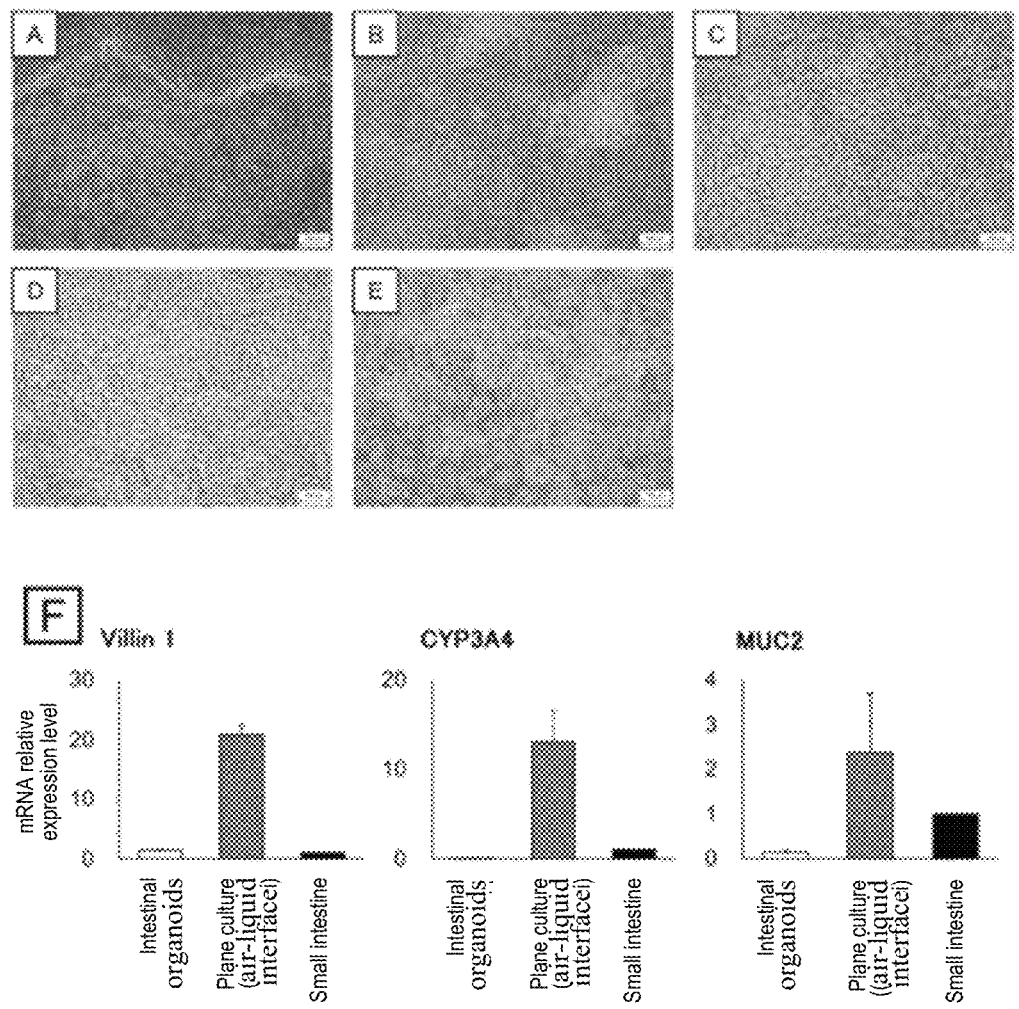

[Fig. 14-1]
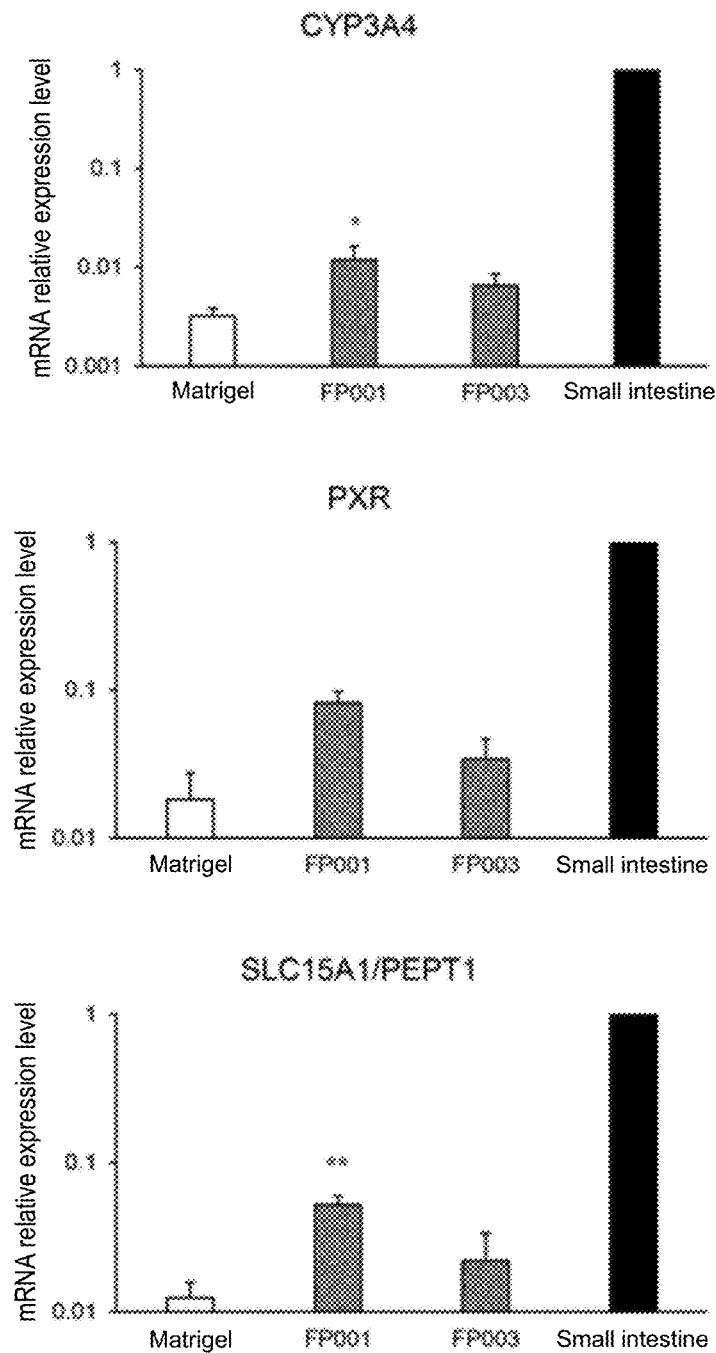

[Fig. 14-2]
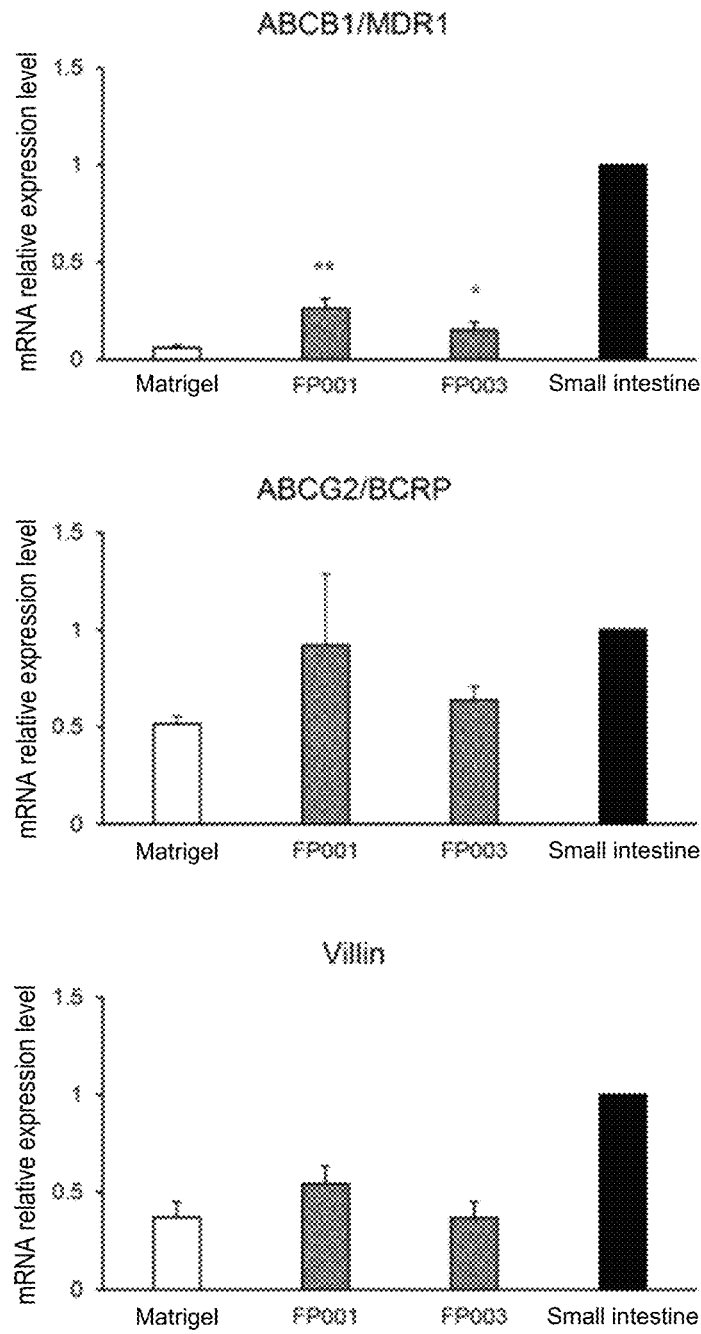

[Fig. 14-3]
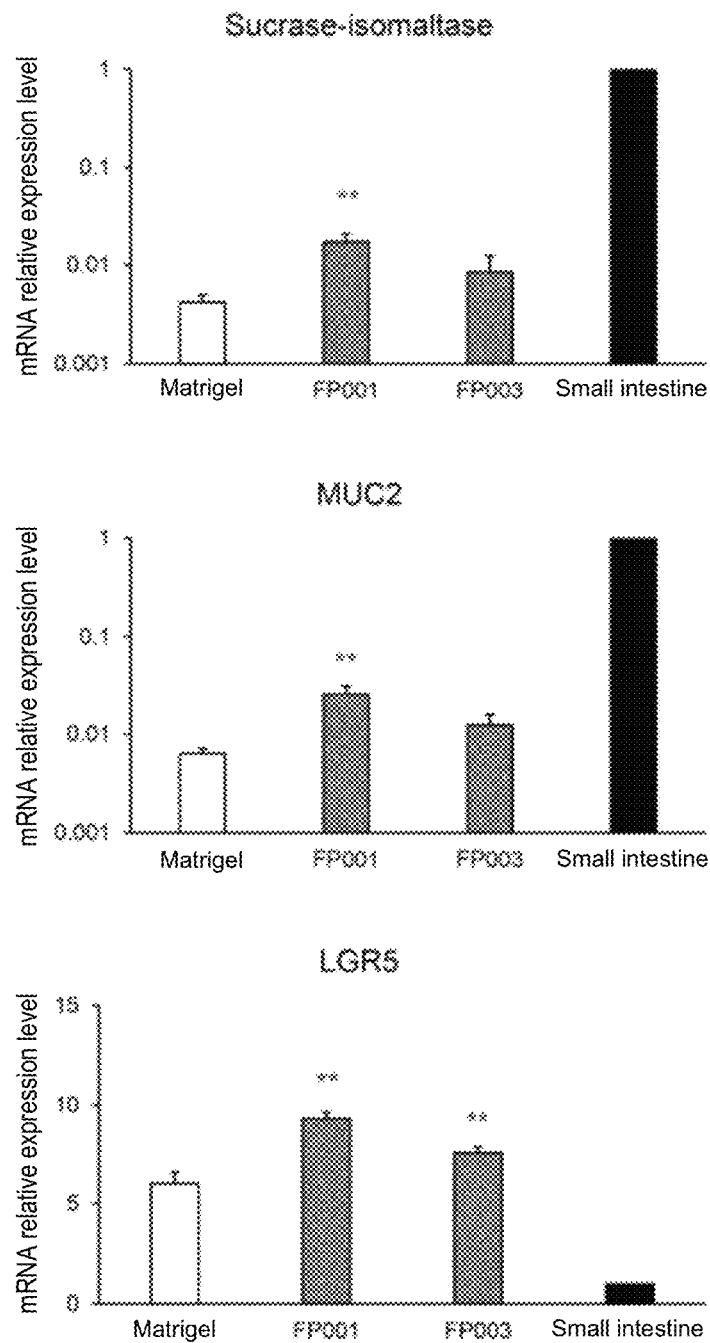

[Fig. 14-4]
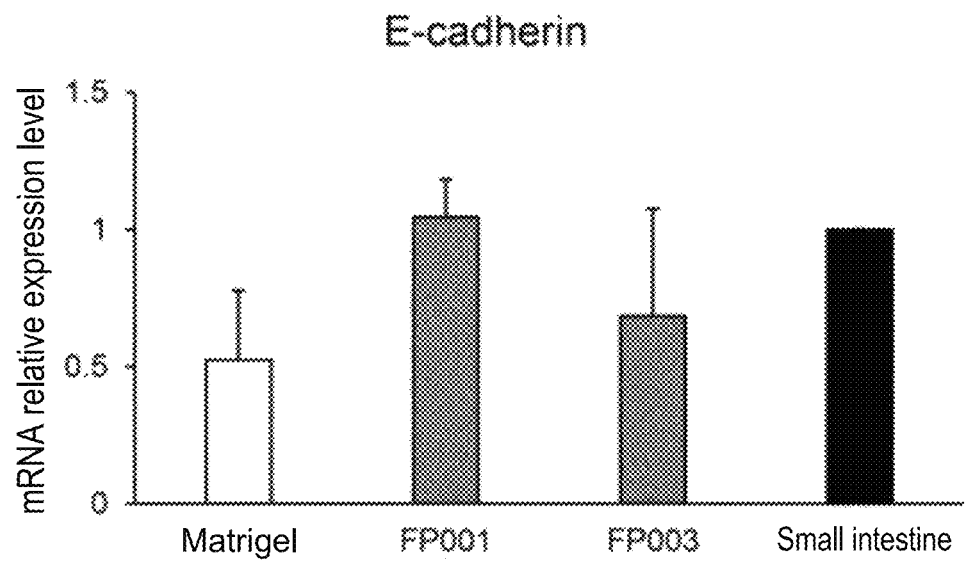
[Fig. 15]
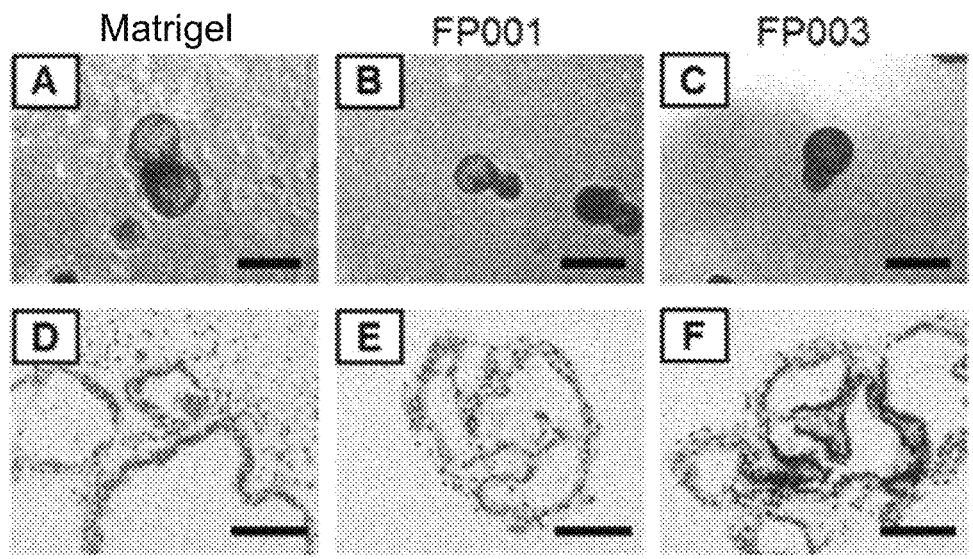

[Fig. 16]
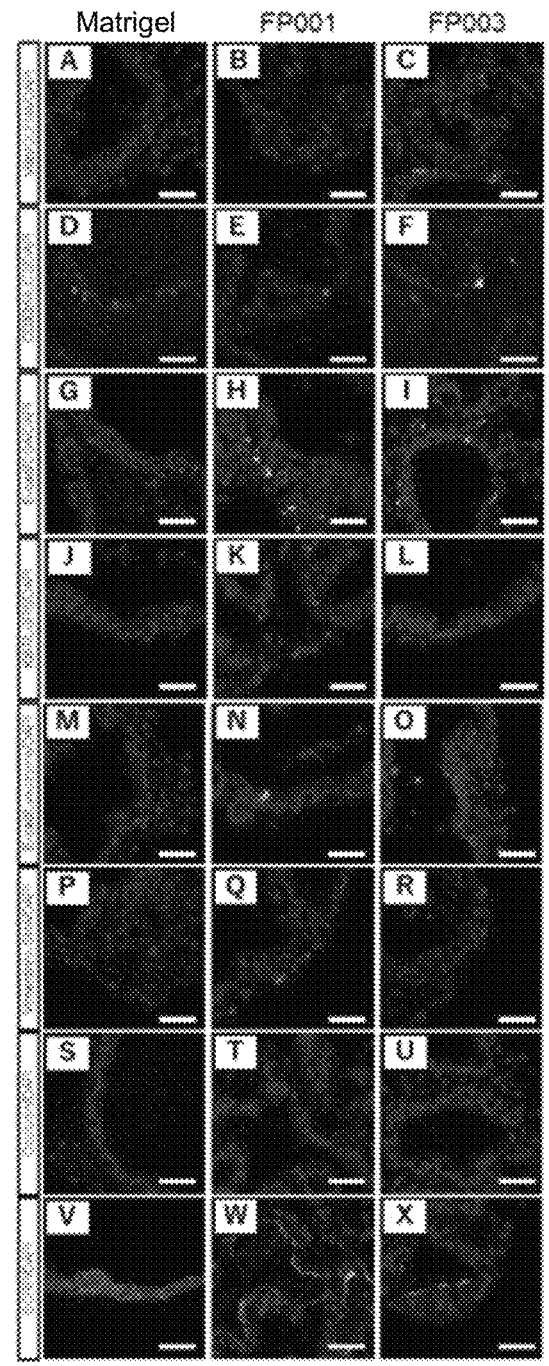

[Fig. 17]
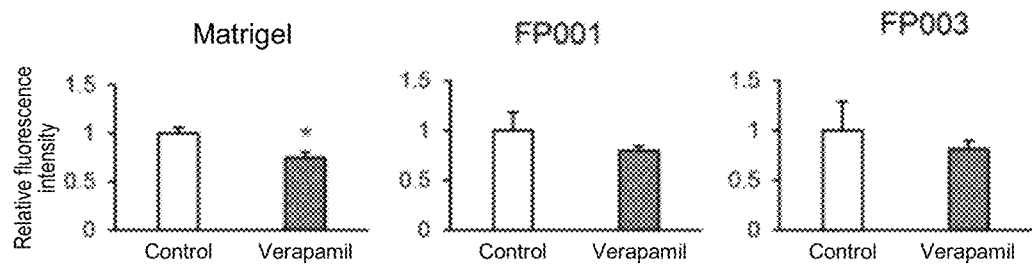
[Fig. 18]
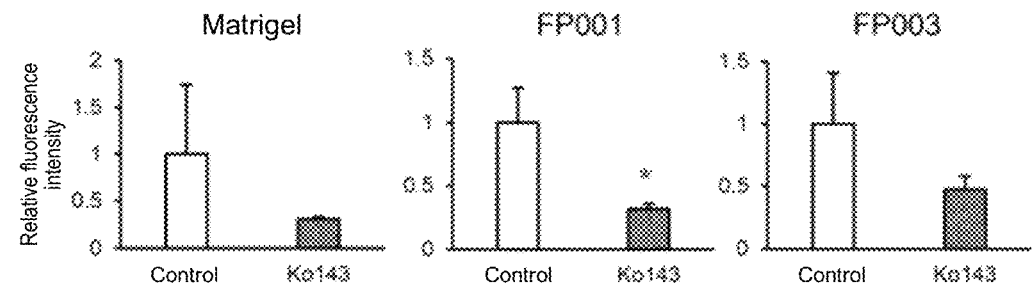
[Fig. 19]
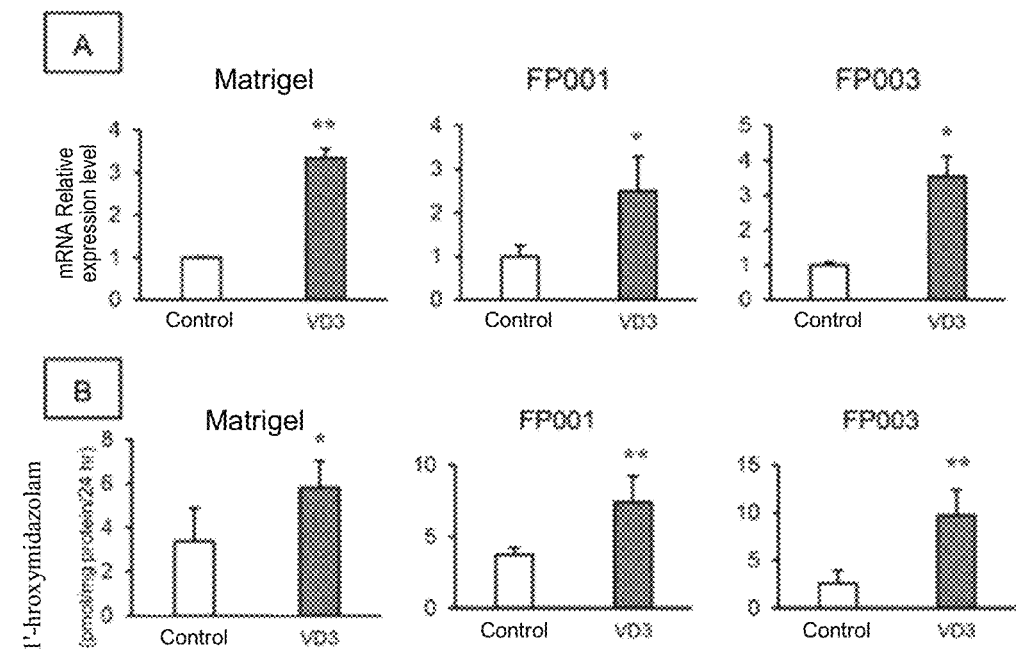

[Fig. 20]
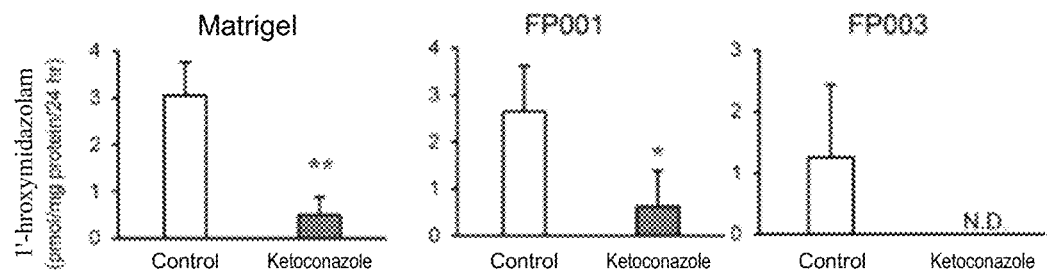

METHOD FOR PREPARING INTESTINAL TRACT CELL LAYER DERIVED FROM PLURIPOTENT STEM CELL

CROSS REFERENCE TO RELATED APPLICATIONS

This application is a National Stage of International Application No. PCT/JP2019/042938 filed Oct. 31, 2019, claiming priority to Japanese Patent Application No. 2018-207108 filed Nov. 2, 2018 and Japanese Patent Application No. 2019-092336 filed May 15, 2019, the contents of all of which are incorporated herein by reference in their entirety.

TECHNICAL FIELD

The present invention relates to a method for preparing an intestinal organoid derived from a pluripotent stem cell and use thereof.

BACKGROUND ART

The small intestine is an extremely important organ in investigating in vivo kinetics of a drug orally administered. For comprehensive evaluation of pharmacokinetics (absorption, excretion, metabolism) in the human small intestine at a nonclinical stage, primary small-intestinal epithelial cells are desirably used; however, it is difficult to obtain the primary small-intestinal epithelial cells, themselves. Recently, a three-dimensional tissue structure (organoid), which mimics the intestinal tract tissue, has attracted attention as a new in-vitro evaluation system. The intestinal organoid is highly expected as an important tool for investigating and treating intestinal diseases. Currently, an intestinal organoid derived from a human tissue is experimentally used; however, due to extremely high invasiveness its availability and stable supply thereof are very difficult. Then, human induced pluripotent stem (iPS) cell-derived intestinal organoid, which is low in invasiveness and also available as a disease model, attracts attention.

Non-human mammals are useful as disease models and for biomedical research. Particularly, cynomolgus monkeys, which are used as experimental animals in drug discovery research, are quite similar to humans in many points. The amino acid sequences of a drug-metabolizing enzyme and a drug transporter of them have a homology of 90 to 95%, and substrate specificities of them are analogous. Because of this, if the correlations in vivo and in vitro in a nonclinical stage are checked by using cynomolgus monkeys, humans can be (more) accurately estimated.

It has been reported that an intestinal epithelial cells were prepared from an ES cell and an iPS cell by two dimensional (2D) culture (see, for example, Patent Documents 1 and 2); and that an intestinal organoid was prepared by three dimensional (3D) culture using e.g., Matrigel (see, for example, Patent Documents 3, 4, Non-Patent Documents 1 to 4).

PRIOR ART DOCUMENTS

Patent Documents

Patent Document 1: International Publication WO 2014/132933
Patent Document 2: International Publication WO 2012/060315
Patent Document 3: International Publication WO 2016/093222
Patent Document 4: JP Patent Publication (Kokai) No. 2006-239169A

Non-Patent Documents

Non-Patent Document 1: Drug Metab. Pharmacokinetic Vol. 29 (1). P. 44-51 (2014)
Non-Patent Document 2: Nature, Vol. 470, P. 105-109 (2011)
Non-Patent Document 3: Stem Cells, vol. 24, P. 2618-2626 (2006)
Non-Patent Document 4: Biochem. Biophys. Res. Commun., Vol. 391 (1), No. 7, P. 38-42 (2010)

SUMMARY OF INVENTION

Object to be Solved by the Invention

In the intestinal organoid prepared by "differentiation induction" currently in use, since the structure of the intestinal tract is still incomplete, crypt-villus structures of the intestinal tract are not reproduced. The intestinal organoid is principally prepared through culture using Matrigel as an embedding substance; however, since the volume of the culture is limited, it is difficult to apply the culture using Matrigel to the analysis, such as high throughput assay, requiring a large number of intestinal organoids. Then, a first object of the present invention is to prepare an intestinal organoid, which has characteristics (more) close to those of the small intestine of a living body, from a pluripotent stem cell; and a second object of the present invention is to improve the production efficiency of an intestinal organoid.

Means for Solving the Object

The present inventors added original ideas to culture condition (particularly, combination of low-molecular compounds and the presence or absence of procedure for passage culture) during differentiation induction and whether the ideas are effective or not was checked. As a result, they succeeded in preparing a "budding" intestinal organoid having a structure close to that of the intestinal tract of a living body. In other words, (culture) condition for preparing an intestinal organoid having characteristics closer to those of the small intestine of a living body was found out. They also succeeded in improving a culture method, thereby preparing highly uniform intestinal organoids in a large number. When usefulness of the intestinal organoid prepared was evaluated, it was found that the organoid can be highly practically used/applied to, e.g., a drug screening system. Note that, factors employed as a new combination are all low-molecular compounds low in cost and lot-to-lot variability. These features provide not only reducing production cost but also improving quality and reliability of the intestinal organoid.

As a result of further studies conducted by the inventors, they succeeded in increasing the function of an intestinal organoid by adding a predetermined low-molecular compound to the final-stage of suspension culture. In addition, they also succeeded in constructing a two-dimensional evaluation model, which is (more) suitable for high throughput assay, by collecting cells from the intestinal organoid to form a cell layer; at the same time, they found a condition effective for enhancing the function thereof.

The following inventions are principally based on the aforementioned outcomes.

[1] A method for preparation of an intestinal organoid from a pluripotent stem cell, comprising the following steps (1) to (5):
  (1) differentiating the pluripotent stem cell into an endoderm-like cell;
  (2) differentiating the endoderm-like cell obtained in step (1) into an intestinal stem cell-like cell;
  (3) culturing the intestinal stem cell-like cell obtained in step (2) in the presence of an epidermal growth factor, a fibroblast growth factor, a TGF β receptor inhibitor, a GSK-3 β inhibitor, and a ROCK inhibitor;
  (4) culturing the cell obtained in step (3) to form a spheroid; and
  (5) differentiating the spheroid formed in step (4) to form an intestinal organoid, wherein the differentiation comprises culturing in the presence of an epidermal growth factor, a BMP inhibitor, and a Wnt signal activator.

[2] The preparation method according to [1], wherein the culture of step (3) is carried out by using a culture surface coated with a basal membrane component.

[3] The preparation method according to [2], wherein the basal membrane component is laminin 511 or an E8 fragment thereof.

[4] The preparation method according to any one of [1] to [3], wherein, in step (3), a procedure for passage culture is carried out.

[5] The preparation method according to [4], wherein the number of times of the procedure for passage culture is 1 or 2.

[6] The preparation method according to any one of [1] to [5], wherein the fibroblast growth factor is FGF2, FGF4 or FGF10; the TGF β receptor inhibitor is A-83-01; the GSK-3 β inhibitor is CHIR99021, SB216763, CHIR98014, TWS119, Tideglusib, SB415286, BIO, AZD2858, AZD1080, AR-A014418, TDZD-8, LY2090314, IM-12, Indirubin, Bikinin or 1-Azakenpaullone; and the ROCK inhibitor is Y-27632.

[7] The preparation method according to any one of [1] to [6], wherein the period of the culture of step (3) is 2 to 14 days.

[8] The preparation method according to any one of [1] to [7], wherein, in the culture of step (4), a plurality of spheroids are simultaneously formed by using a culture vessel having a plurality of wells uniform in shape and size formed on a low cell-adhesive or non cell-adhesive culture surface.

[9] The preparation method according to any one of [1] to [8], wherein a plurality of spheroids formed in step (4) are simultaneously cultured in a suspension state, by using a liquid medium adding a material for forming a three-dimensional network structure in an aqueous solution for the culture of step (5).

[10] The preparation method according to [9], wherein the material is at least one selected from the group consisting of a polymer gel and a polysaccharide.

[11] The preparation method according to [9], wherein the material comprises deacylated gellan gum.

[12] The preparation method according to any one of [1] to [11], wherein, the BMP inhibitor is Noggin, and the Wnt signal activator is R-spondin-1. [13] The preparation method according to any one of [1] to [12], wherein the culture period of step (5) is 12 to 36 days.

[14] The preparation method according to any one of [1] to [13], wherein the culture of step (5) is carried out in the presence of an MEK1/2 inhibitor, a DNA methylation inhibitor, a TGF β receptor inhibitor, and a γ-secretase inhibitor in addition to an epidermal growth factor, a BMP inhibitor, and a Wnt signal activator.

[15] The preparation method according to any one of [1] to [13], wherein the culture of step (5) is carried out in the presence of an MEK1/2 inhibitor, a DNA methylation inhibitor, and a TGF β receptor inhibitor in addition to an epidermal growth factor, a BMP inhibitor, and a Wnt signal activator.

[16] The preparation method according to any one of [1] to [15], wherein the pluripotent stem cell is an induced pluripotent stem cell or an embryonic stem cell.

[17] The preparation method according to any one of [1] to [15], wherein the pluripotent stem cell is a human induced pluripotent stem cell.

[18] The preparation method according to [17], wherein the human induced pluripotent stem cell is derived from a patient having an intestinal disease.

[19] An intestinal organoid obtained by the preparation method according to any one of [1] to [18].

[20] A method for evaluating in vivo kinetics or toxicity of a test substance by using the intestinal organoid according to [19].

[21] The evaluation method according to [20], wherein the in vivo kinetics is metabolism, absorbency, membrane permeability, drug interaction, induction of a drug-metabolizing enzyme, or induction of a drug transporter.

[22] The method according to [21], comprising the following steps (I) and (II):
  (I) contacting the test substance with the intestinal organoid according to [19]; and
  (II) determining/evaluating test substance's metabolism, absorbency, membrane permeability, drug interaction, induction of a drug-metabolizing enzyme, or induction of a drug transporter, or toxicity.

[23] A method for preparing an intestinal disease model, comprising inducing a pathological condition of an intestinal disease in the intestinal organoid obtained by the preparation method according to any one of [1] to [17].

[24] A transplant material comprising the intestinal organoid according to [19].

[25] A preparation method for an intestinal tract cell layer from a pluripotent stem cell, comprising the following steps (1) to (6):
  (1) differentiating the pluripotent stem cell into an endoderm-like cell;
  (2) differentiating the endoderm-like cell obtained in step (1) into an intestinal stem cell-like cell;
  (3) culturing the intestinal stem cell-like cell obtained in step (2) in the presence of an epidermal growth factor, a fibroblast growth factor, a TGF β receptor inhibitor, a GSK-3 β inhibitor, and a ROCK inhibitor;
  (4) culturing the cell obtained in step (3) to form a spheroid;
  (5) differentiating the spheroid formed in step (4) to form an intestinal organoid, wherein the differentiation comprises culturing in the presence of an epidermal growth factor, a BMP inhibitor, and a Wnt signal activator; and (6) subjecting the cells constituting the intestinal organoid formed in step (5) to plane culture carried out in the presence of an epidermal growth factor and a TGF β receptor inhibitor.

[26] The preparation method according to [25], wherein the culture of step (6) is carried out in the presence of a cAMP activation substance in addition to an epidermal growth factor and a TGF β receptor inhibitor.

[27] The preparation method according to [25], wherein the culture of step (6) is carried out in the presence of a cAMP activation substance and a γ-secretase inhibitor in addition to an epidermal growth factor and a TGF β receptor inhibitor.

[28] The preparation method according to [25], wherein the culture of step (6) is carried out in the presence of a cAMP activation substance and a GSK-3 β inhibitor in addition to an epidermal growth factor and a TGF β receptor inhibitor.

[29] The preparation method according to [25], wherein at least part of the plane culture of step (6) is air-liquid interface culture.

[30] The preparation method according to [29], wherein the air-liquid interface culture is carried out in the presence of a factor activating a cAMP signal in addition to an epidermal growth factor and a TGF β receptor inhibitor.

[31] The preparation method according to [30], wherein the factor is a cAMP derivative, a cAMP-degrading enzyme inhibitor or a cAMP activation substance.

[32] The preparation method according to [30], wherein the factor is forskolin.

[33] An intestinal tract cell layer obtained by the method according to any one of [25] to [32].

[34] A method for evaluating in vivo kinetics or toxicity of a test substance by using the intestinal tract cell layer according to [33].

[35] The method according to [34], wherein the in vivo kinetics is metabolism, absorbency, membrane permeability, drug interaction, induction of a drug-metabolizing enzyme, or induction of a drug transporter.

[36] The method according to [34] or [35], comprising the following steps (i) to (iii):
(i) preparing the intestinal tract cell layer according to [33];
(ii) contacting a test substance with the intestinal tract cell layer; and
(iii) quantifying the test substance passed through the intestinal tract cell layer and evaluating the test substance's metabolism, absorbency, membrane permeability, drug interaction, induction of a drug-metabolizing enzyme, or induction of a drug transporter, or toxicity.

[37] The method according to [34] or [35], comprising the following steps (I) and (II):
(I) contacting the test substance with the intestinal tract cell layer according to [33]; and
(II) determining/evaluating test substance's metabolism, absorbency, membrane permeability, drug interaction, induction of a drug-metabolizing enzyme, or induction of a drug transporter, or toxicity.

[38] A method for preparing an intestinal disease model, comprising inducing a pathological condition of an intestinal disease in the intestinal tract cell layer obtained by the preparation method according to any one of [25] to [32].

BRIEF DESCRIPTION OF DRAWINGS

FIG. 1 shows morphology of intestinal organoids prepared in accordance with a new intestinal organoid preparation method. (A) control group (a group of intestinal organoids formed by seeding cells on Day 7 after differentiation induction on EZSPHERE (registered trademark)). (B) cells obtained by seeding cells on Day 7 after differentiation induction on iMatrix511 and culturing the cells by using culture medium 5 up to Day 11. The cells were passaged every two days. (C) cells obtained by seeding cells on Day 7 after differentiation induction on iMatrix511 and culturing the cells by using culture medium 5 up to Day 14. The cells were passaged every two days. (D) Cells obtained by culturing cells by using SB216763 (2 μmol/L) in place of CHIR99021. (E) Cells obtained by culturing cells by using SB415286 (10 μmol/L) in place of CHIR99021. (F) Cells obtained by culturing cells by using CHIR98014 (200 nmol/L) in place of CHIR99021. (G) Cells obtained by culturing cells by using (2'Z,3'E)-6-Bromoindirubin-3'-oxime (1 μmol/L) in place of CHIR99021. (H) Cells obtained by culturing cells by using AZD1080 (2 μmol/L) in place of CHIR99021. (I) Cells obtained by culturing cells by using LY2090314 (4 μmol/L) in place of CHIR99021. Scale bar: 500 μm.

FIG. 2 shows gene expression of an intestinal organoid prepared by a new intestinal organoid preparation method. Average±S.D. (n=3). Control: Cells on Day 7 after differentiation induction. Day 11: Cells obtained by seeding cells on Day 7 after differentiation induction on iMatrix511silk and culturing the cells by using culture medium 5 up to Day 11. Day 14: Cells obtained by seeding cells on Day 7 after differentiation induction on iMatrix511silk and culturing the cells by using culture medium 5 up to Day 14. "Passaged": Cells passaged every two days by seeding cells on iMatrix511silk and culturing them by using culture medium 5. "Non passaged": Cells cultured by using culture medium 5 without being passaged. The mRNA expression level of adult small intestine was regarded as 1.

FIG. 3 shows morphology of intestinal organoids analyzed by a new intestinal organoid preparation method. (A) Stained with HE. Scale bar: 100 μm. (B) Stained with Alcian Blue. Scale bar: 100 μm. (C) Immunofluorescent staining. DAPI: nuclear staining. Scale bar: 50 μm.

FIG. 4 shows characteristics of an intestinal organoid prepared by a new intestinal organoid preparation method. Average±S.D. (n=3). The mRNA expression level of adult colon was regarded as 1.

FIG. 5 shows gene expression analysis and immunofluorescent staining of a drug transporter of an intestinal organoid prepared by a new intestinal organoid preparation method. (A) Expression of a pharmacokinetics-related gene of an intestinal organoid prepared by a new intestinal organoid preparation method. Average±S.D. (n=3). The mRNA expression level of adult small intestine was regarded as 1. (B) Immunofluorescent staining of an intestinal organoid prepared by a new intestinal organoid preparation method. DAPI: Nuclear staining. Scale bar: 50 μm.

FIG. 6 shows mRNA expression analysis of cells immediately before seeding on EZSPHERE. Average±S.D. (n=3). Control: Cells on Day 7 after differentiation induction. Day 11: Cells obtained by seeding cells on Day 7 after differentiation induction on iMatrix511silk and culturing the cells by using culture medium 5 up to Day 11. Day 14: Cells obtained by seeding cells on Day 7 after differentiation induction on iMatrix511silk and culturing the cells by using culture medium 5 up to Day 14. "Passaged": Cells passaged every two days by seeding cells on iMatrix511silk and culturing them by using culture medium 5. "Non passaged": Cells cultured by using culture medium 5 without being passaged. The mRNA expression level of the control was regarded as 1.

FIG. 7-1 shows preparation of an inflammatory bowel disease model in the case of TNF-α addition. (A) Protocol for preparation of an inflammatory bowel disease model. (B) The mRNA expression analysis of an intestinal organoid in the cases of TNF-α and infliximab addition. Average±S.D. (n=3). The mRNA expression level of the control was regarded as 1. (C) Immunofluorescent staining of an intestinal organoid in the cases of TNF-α and infliximab addition. DAPI: Nuclear staining. Scale bar: 50 µm.

FIG. 7-2 shows the figure continued from FIG. 7.

FIG. 8 shows preparation of a fibrosis model in the cases of TNF-α and TGF-β addition. (A) A protocol for preparation of a fibrosis model. (B) The mRNA expression analysis of an intestinal organoid in the cases of addition of TNF-α+TGF-β and TGF-β inhibitor (SB431542, Repsox). Average±S.D. (n=3). The mRNA expression level of the control was regarded as 1.

FIG. 9 shows the protocol of differentiation from a human iPS cell to an intestinal organoid and the list of mediums used for differentiation induction. PS (100 units/mL penicillin G, 100 µg/mL streptomycin).

FIG. 10 shows a change in gene expression level of intestinal organoid in the case of addition of a low-molecular compound. A low-molecular compound was added from Day 19 after initiation of differentiation up to completion of differentiation (1: 20 µmol/L PD98059, 5 µmol/L 5-aza-2'-deoxycytidine, 0.5 µmol/L A-83-01. 2: 20 µmol/L PD98059, 5 µmol/L 5-aza-2'-deoxycytidine, 0.5 µmol/L A-83-01, 2.5 µmol/L DAPT). Data shown were "average±S.D. (n=3)". The mRNA expression level of adult small intestine was regarded as 1.

FIGS. 11-1A and 11-1A show mRNA expression analysis (A) and measurement of membrane resistance value (B) of the new plane culture system prepared. Intestinal organoid: Intestinal organoid on Day 34 after differentiation induction. Plane culture: Cells obtained by passaging the intestinal organoid on iMatrix511silk, adding a low-molecular compound (30 µmol/L forskolin, 2.5 µmol/L DAPT, 3 µmol/L CHIR99021) to culture medium 7 (see, FIG. 9), and culturing the cells for 7 days. Control: Cells obtained in the absence of a low-molecular compound. The mRNA expression level of adult small intestine was regarded as 1. (n=1)

FIG. 11-2 shows the figure continued from FIG. 11.

FIG. 12 shows induction test of CYP3A4 using a new plane culture system. Cells obtained by passaging an intestinal organoid on iMatrix511silk and culturing by using culture medium 7 and a low-molecular compound (30 µmol/L forskolin, 2.5 µmol/mL DAPT (96 hours after seeding), 3 µmol/L CHIR99021 (96 hours after seeding), 10 µmol/L Y-27632 (24 hours after seeding)) for 8 days and exposed to an inducer (DMSO: solvent, rifampicin: 3 µmol/L, activated vitamin $D_3$: 10 nmol/L) for 48 hours. The mRNA expression level of DMSO was regarded as 1 (n=1).

FIG. 13 shows formation of a villus-like structure in the case of a air-liquid interface culture and addition of a low-molecular compound. (A-E): intestinal organoid was passaged on iMatrix511silk and cultured by using culture medium 7 containing a low-molecular compound (2.5 µmol/L DAPT (96 hours after seeding), 3 µmol/L CHIR99021 (96 hours after seeding), 10 µmol/L Y-27632 (24 hours after seeding)) and test factors (A: A83-01 not added, 30 µmol/L forskolin; B: A83-01 added, forskolin not added; C: A83-01 added, 30 µmol/L forskolin; D: A83-01 added, 1 mmol/L 8-Br-cAMP; E: A83-01 added, 500 µmol/L IBMX) for 10 days. Scale bar: 100 µm. Graph (F) shows the mRNA expression level measured by q PCR in the plane culture system prepared in accordance with the protocol (C). Data shown were "average±S.D. (n=3)". The mRNA expression level of adult small intestine was regarded as 1.

FIG. 14-1 shows the effect of polysaccharide polymers (FP001, FP003) on differentiation of a human iPS cell to an intestinal organoid. Data shown were "average±S.D. (n=3)". The expression level of small intestine was used as a reference (small intestine=1). *P<0.05, **P<0.01 vs Matrigel FIG. 14-2 shows the figure continued from FIG. 14.

FIG. 14-3 shows the figure continued from FIG. 14.

FIG. 14-4 shows the figure continued from FIG. 14.

FIG. 15 shows morphology of human intestinal organoids obtained by differentiation induction with polysaccharide polymers (FP001, FP003). (A)-(C): Observation in a bright field. Scale bar: 500 (D)-(F): Stained with HE. Scale bar 100 µm.

FIG. 16 shows immunofluorescent staining of human intestinal organoids obtained by differentiation induction with polysaccharide polymers (FP001, FP003). (A)-(C): Villin/OLFM4. (D)-(F): CDX2 (cell lineage of intestinal tract system)/MUC2. (G)-(I): E-cad (epithelial cell adhesion factor)/CHGA (Chromogranin A). (J)-(L): Ki67 (proliferative cell marker)/LGR5 (stem cell marker). (M)-(O): E-cad/Lyso (Lysozyme). (P)-(R): Vim (Vimentin: fibroblast marker)/α-SMA (smooth muscle marker). (S)-(U): Occludin (tight junction). (V)-(X): ABCG2/BCRP (efflux transporter). DAPI: nuclear staining. Scale bar: 50 µm.

FIG. 17 shows functions of ABCB1/MDR1 of human intestinal organoids obtained by differentiation induction with polysaccharide polymers (FP001, FP003), evaluated by use of rhodamine 123. As an inhibitor of ABCB1/MDR1, verapamil (100 µmol/L) was used. Data shown were "average±S.D. (n=3)". The value of a control group (no inhibitor added) was used as a reference (control group=1). *P<0.05 vs control group.

FIG. 18 shows functions of ABCG2/BCRP of human intestinal organoids obtained by differentiation induction with polysaccharide polymers (FP001, FP003), evaluated by use of Hoechst 33342. As an inhibitor of ABCG2/BCRP, Ko143 (20 µmol/L) was used. Data shown were "average±S.D. (n=3)". The value of a control group (inhibition agent was not added) was used as a reference (control group=1). *P<0.05 vs control group.

FIG. 19 shows CYP3A4 induction potency of human intestinal organoids obtained by differentiation induction with polysaccharide polymers (FP001, FP003). (A) Data shown were "average±S.D. (n=3)". Control: Inducer-free group. **P<0.01, *P<0.05 vs control group. The value of a control group was used as a reference (control group=1). (B) Data shown were "average±S.D. (n=4)". Control: Inducer-free group. **P<0.01, *P<0.05 vs control group.

FIG. 20 shows CYP3A4 metabolic activity of human intestinal organoids obtained by differentiation induction with polysaccharide polymers. Data shown were "average±S.D. (n=4)". Control: ketoconazole-free group. N.D.: not detected. **P<0.01, *P<0.05 vs control group.

EMBODIMENT OF CARRYING OUT THE INVENTION

1. Method for Preparing Intestinal Organoid

The present invention relates to a method for preparing an intestinal organoid from a pluripotent stem cell (hereinafter referred to also as "the preparation method of the invention"). According to the present invention, it is possible to obtain an intestinal organoid, which is a three-dimensional tissue structure (that mimics the intestinal tract tissue) having analogous characteristics as those of the intestinal tract tissue of a living body.

The "pluripotent stem cell" refers to a cell having not only an ability (pluripotency) to differentiate into any types of cells constituting a living body but also an ability (self-replicating ability) to produce daughter cells having the same differentiation ability as their own through cell division. Pluripotency can be evaluated by transplanting an evaluation target cell to a nude mouse and examining whether a teratoma containing individual cells of three germ layers (ectoderm, mesoderm, endoderm) is formed or not.

Examples of the pluripotent stem cell include an embryonic stem cell (ES cell), an embryonic germ cell (EG cell), and an induced pluripotent stem cell (iPS cell); however, the pluripotent stem cell is not limited to these as long as it has both pluripotency and self-replicating ability. Preferably, an ES cell or an iPS cell is used. Further preferably an iPS cell is used. The pluripotent stem cell is preferably that of a mammal (for example, a primate such as a human, a chimpanzee, a cynomolgus monkey, and a rodent such as a mouse and a rat) and particularly preferably a human cell.

The ES cell is established by culturing, for example, an early embryo before implantation, inner cell mass constituting an early embryo, or a single blastomere (Manipulating the Mouse Embryo A Laboratory Manual, Second Edition, Cold Spring Harbor Laboratory Press (1994); Thomson, J. A. et al., Science, 282, 1145-1147 (1998)). As the early embryo, an early embryo prepared by implanting a nucleus of a somatic cell, may be used (Wilmut et al., (Nature, 385,810 (1997)), Cibelli et al., (Science, 280, 1256 (1998)), Akira Iritani et al. (Protein Nucleic Acid Enzyme, 44, 892 (1999)), Baguisi et al., (Nature Biotechnology, 17, 456 (1999)), Wakayama et al., (Nature, 394, 369 (1999); Nature Genetics, 22, 127 (1999); Proc. Natl. Acad. Sci. USA, 96, 14984 (1999)), Rideout III et al., (Nature Genetics, 24, 109 (2000), Tachibana et al., (Human Embryonic Stem Cells Derived by Somatic Cell Nuclear Transfer, Cell, 153, 1228-1238 (2013)). As the early embryo, a parthenogenetic embryo may be used (Kim et al., (Science, 315, 482-486 (2007)), Nakajima et al., (Stem Cells, 25, 983-985 (2007)), Kim et al., (Cell Stem Cell, 1, 346-352 (2007)), Revazova et al., (Cloning Stem Cells, 9, 432-449 (2007)), Revazova et al., (Cloning Stem Cells, 10, 11-24 (2008))). Other than the papers listed above, ES cells may be prepared with reference to Strelchenko N., et al., Reprod Biomed Online. 9: 623-629, 2004; Klimanskaya I., et al., Nature 444: 481-485, 2006; Chung Y., et al., Cell Stem Cell 2: 113-117, 2008; Zhang X., et al., Stem Cells 24: 2669-2676, 2006; and Wassarman, P. M. et al., Methods in Enzymology, Vol. 365, 2003. Note that, a fused ES cell obtained by cell fusion of an ES cell and a somatic cell is also included in the embryonic stein cell to be used in the preparation method of the invention.

Of the ES cells, ES cells available from a culture collection and commercially available ES cells are known. For example, human ES cells (for example, KhES-1, KhES-2, and KhES-3) can be obtained from, e.g., the Institute for Frontier Life and Medical Sciences, Kyoto University, WiCell Research Institute, and ESI BIO.

ES cells can be established, for example, by culturing primordial germ cells in the presence of LIF, bFGF, and SCF (Matsui et al., Cell, 70, 841-847 (1992), Shamblott et al., Proc. Natl. Acad. Sci. USA, 95 (23), 13726-13731 (1998), Turnpenny et al., Stem Cells, 21 (5), 598-609, (2003)).

The "induced pluripotent stem cell (iPS cell)" is a cell having a multipotency (pluripotency) and a proliferative ability and prepared by reprogramming a somatic cell by introducing initialization factors and the like. The induced pluripotent stem cell exhibits properties close to an ES cell. The somatic cell to be used for producing an iPS cell, although it is not particularly limited, may be a differentiated somatic cell or an undifferentiated stem cell. The cell from which an iPS cell is derived, although it is not particularly limited, is preferably a somatic cell of a mammal (for example, a primate such as a human, a chimpanzee, a cynomolgus monkey and a rodent such as a mouse and a rat); and particularly preferably a human somatic cell. The iPS cell can be prepared by any one of the methods so far reported. Needless to say, a method that will be developed in future for preparing an iPS cell, is presumably applied.

If an iPS cell derived from a patient having an intestinal disease (iPS cell prepared from a patient's somatic cell) is used, an intestinal organoid specific to the disease can be prepared. The iPS cell is prepared from a somatic cell (for example, skin, blood, mononucleosis) taken from a patient. Examples of the intestinal disease include a refractory inflammatory bowel disease (Crohn's disease, ulcerative colitis), polyp, colorectal cancer, and drug-induced enteritis. A disease-specific intestinal organoid is useful as an intestinal tract pathology model and use thereof in a drug evaluation system and contribution to elucidation of a disease mechanism (molecular mechanism of, e.g., onset, production/progression of a pathological condition).

The most basic method for preparing an iPS cell is a method of introducing four transcription factors, Oct3/4, Sox2, Klf4 and c-Myc, into a cell by use of a virus (Takahashi K, Yamanaka S: Cell 126 (4), 663-676, 2006; Takahashi K, et al.: Cell 131 (5), 861-72, 2007). It is reported that a human iPS cell is established by introduction of four factors, Oct4, Sox2, Lin28 and Nonog (Yu J, et al: Science 318 (5858), 1917-1920, 2007). It is also reported that an iPS cell is established by introducing three factors except c-Myc (Nakagawa M, et al: Nat. Biotechnol. 26 (1), 101-106, 2008), two factors, Oct3/4 and Klf4 (Kim J B, et al: Nature 454 (7204), 646-650, 2008), or Oct3/4 alone (Kim J B, et al: Cell 136 (3), 411-419, 2009). In addition, a method of introducing a gene expression product, i.e., a protein, into a cell, is reported (Zhou H, Wu S, Joo J Y, et al: Cell Stem Cell 4, 381-384, 2009; Kim D, Kim C H, Moon J I, et al: Cell Stem Cell 4, 472-476, 2009). In addition, there are reports that a production efficiency can be improved and the number of factors to be introduced can be reduced by use of an inhibitor BIX-01294 of histone methyltransferase G9a and a histone deacetylase inhibitor such as valproic acid (VPA) or BayK 8644 (Huangfu D, et al: Nat. Biotechnol. 26 (7), 795-797, 2008; Huangfu D, et al: Nat. Biotechnol. 26 (11), 1269-1275, 2008; Silva J, et al: PLoS. Biol. 6 (10), e253, 2008). Studies on a gene introduction method have been conducted and a technique of introducing a gene using, other than retroviruses, a lentivirus (Yu J, et al: Science 318 (5858), 1917-1920, 2007), an adenovirus (Stadtfeld M, et al: Science 322 (5903), 945-949, 2008), a plasmid (Okita K, et al: Science 322 (5903), 949-953, 2008), a transposon vector (Woltjen K, Michael I P, Mohseni P, et al: Nature 458, 766-770, 2009; Kaji K, Norrby K, Paca A, et al: Nature 458, 771-775, 2009; Yusa K, Rad R, Takeda J, et al: Nat Methods 6, 363-369, 2009) or an episomal vector (Yu J, Hu K, Smuga-Otto K, Tian S, et al: Science 324, 797-801, 2009) has been developed.

The cell transformed into an iPS cell, that is, the initialized (reprogrammed) cell, can be screened based on expression of a pluripotent stem cell marker (undifferentiation-cell marker), such as Fbxo15, Nanog, Oct/4, Fgf-4, Esg-1 and Cript, as an index. The screened cell is recovered as an iPS cell.

Induced pluripotent stem cell (iPS cell) can be provided from, for example, Kyoto University or National Research and Development Corporation Riken Bioresource Center.

In the specification, the term "be differentiated"/"induce" refers to conduct a procedure so as to differentiate along a predetermined cell lineage. In the present invention, a procedure is conducted to differentiate a pluripotent stem cell into an intestinal organoid. The preparation method of the invention roughly includes five culture steps of: (1) differentiating a pluripotent stem cell into an endoderm-like cell (step (1)); differentiating the endoderm-like cell obtained in step (1) into an intestinal stem cell-like cell (step (2)); culturing the intestinal stem cell-like cell obtained in step (2) in the presence of an epidermal growth factor, a fibroblast growth factor, a TGF β receptor inhibitor, a GSK-3 β inhibitor, and a ROCK inhibitor (step (3)); culturing the cell obtained in step (3) to form a spheroid (step (4)); and differentiating the spheroid formed in step (4) to form an intestinal organoid, wherein the differentiation includes culturing in the presence of an epidermal growth factor, a BMP inhibitor, and a Wnt signal activator (step (5)). The individual steps will be more specifically described below.

<Step (1) Differentiation into Endoderm-Like Cell>

In this step, a pluripotent stem cell is cultured to differentiate into an endoderm-like cell. In other words, a pluripotent stem cell is cultured in the condition for inducing differentiation into an endoderm-like cell. Culture condition is not particularly limited as long as a pluripotent stem cell differentiates into an endoderm-like cell in the condition. For example, a pluripotent stem cell is cultured in a medium containing activin A in accordance with a routine method. In this case, the concentration of activin A in the medium is set to be, for example, 10 ng/mL to 200 ng/mL, and preferably, 20 ng/mL to 150 ng/mL. In view of, e.g., a cell proliferation rate and maintenance, it is preferable to add serum or a serum replacement (e.g., Knockout serum replacement (KSR)) to a medium. The serum is not limited to fetal bovine serum and, e.g., human serum and sheep serum, can be used. The addition amount of serum or a serum replacement is, for example, 0.1% (v/v) to 10% (v/v).

An inhibitor (for example, hexachlorophene, quercetin, a Wnt ligand such as Wnt3a) of the Wnt/β-catenin signal pathway may be added to a culture medium to promote differentiation into an endoderm-like cell.

As step (1), culture may be carried out in two stages. The first-stage culture is carried out in a medium containing a relatively low-concentration serum (for example, 0.1% (v/v) to 1% (v/v)); whereas, the subsequent second-stage culture is carried out in a medium containing the serum in a concentration higher than the first stage (serum concentration is, for example, 1% (v/v) to 10% (v/v)). Such a two-stage culture is preferably employed because proliferation of undifferentiated cells is suppressed by the first-stage culture and differentiated cells are proliferated by the second-stage culture.

The period (culture period) of step (1) is, for example, 1 to 10 days, and preferably, 2 to 7 days. If two-stage culture is employed as step (1), the culture period of the first stage is set to be, for example, 1 to 7 days, and preferably, 2 to 5 days; whereas, the culture period of the second stage is set to be, for example, 1 to 6 days, and preferably, 1 to 4 days.

<Step (2) Differentiation into Intestinal Stem Cell-Like Cell>

In this step, the endoderm-like cell obtained in step (1) is cultured to differentiate into an intestinal stem cell-like cell. In other words, the endoderm cell is cultured in condition for inducing differentiation into an intestinal stem cell-like cell. The culture condition is not particularly limited as long as the endoderm-like cell differentiates into the intestinal stem cell-like cell, in the condition. If a human cell is used as the pluripotent stem cell to be subjected to step (1), culture is preferably carried out in the presence of FGF4 (fibroblast growth factor 4) and a Wnt agonist (for example, Wnt3a, BML-284, 2-Amino-4-(3,4-(methylenedioxy)benzylamino)-6-(3-methoxyphenyl)pyrimidine). As FGF4, human FGF4 (for example, human recombinant FGF4) is preferably used. In another case where, e.g., a cynomolgus cell, a rhesus cell or a chimpanzee cell is used as the pluripotent stem cell to be subjected to step (1), culture is preferably carried out in the presence of FGF2 (fibroblast growth factor 2) and a GSK-3 inhibitor (for example, CHIR99021, CHIR98014, BIO, SB415286, SB216763, TWS119, A1070722). As FGF2, for example, human FGF2 (for example, human recombinant FGF2) is used.

Typically, a cell population or a part thereof obtained through step (1) is subjected to step (2) without screening. However, an endoderm-like cell is screened from the cell population obtained through step (1), and then, step (2) may be carried out. The endoderm-like cell may be screened by a flow cytometer (cell sorter) with, for example, a cell surface marker used as an index.

The phrase "in the presence of FGF4 and a Wnt agonist" is the same in meaning as "in the condition of a medium containing FGF4 and a Wnt agonist". Thus, culture in the presence of FGF4 and a Wnt agonist may be carried out by using a culture medium containing FGF4 and a Wnt agonist. The concentration of FGF4 to be added is, for example, 100 ng/mL to 5 μg/mL, and preferably, 300 ng/mL to 1 μg/mL. The concentration of the Wnt agonist (e.g., Wnt3a) to be added is, for example, 100 ng/mL to 5 μg/mL and preferably, 300 ng/mL to 1 μg/mL.

The phrase "in the presence of FGF2 and a GSK-3 inhibitor" is the same in meaning as "in the condition of a medium containing FGF2 and a GSK-3 inhibitor". Thus, culture in the presence of FGF2 and a GSK-3 inhibitor may be carried out in a culture medium containing FGF2 and a GSK-3 inhibitor. The concentration of FGF2 to be added is, for example, 50 ng/mL to 2.5 μg/mL, and preferably, 150 ng/mL to 500 ng/mL. The concentration of a GSK-3 inhibitor (e.g., CHIR99021) to be added is, for example, 600 nmol/L to 60 μmol/L, and preferably, 1 μmol/L to 20 μmol/L.

Note that, if compounds different from the compounds shown as examples, i.e., Wnt3a and CHIR99021, are used, the concentrations of the compounds to be added can be determined by those skilled in the art in consideration of difference in property (particularly, difference in activity) between the compounds to be used and the compounds mentioned as examples and in accordance with the above ranges of concentrations. Whether the concentration range thus determined is appropriate or not can be checked by a preliminary experiment according to Examples described later.

The period (culture period) of step (2) is, for example, 2 to 10 days, and preferably, 3 to 7 days. If the culture period is excessively short, the desired effect (increasing efficiency of differentiation, promoting an intestinal stem cell to acquire function) cannot be sufficiently obtained. In contrast, if the culture period is excessively long, efficiency of differentiation decreases.

Differentiation into an intestinal stem cell-like cell can be determined or evaluated with, for example, expression of an intestinal stem cell marker used as an index. Examples of the intestinal stem cell marker include leucine rich repeat-containing G protein-coupled receptor 5 (LGR5) and an ephrin B2 receptor (EphB2).

<Step (3) Induction of Differentiation into Intestinal Tract>

In this step, the intestinal stem cell-like cell obtained in step (2) is cultured in the presence of an epidermal growth factor, a fibroblast growth factor, a TGF β receptor inhibitor, a GSK-3 β inhibitor, and a ROCK inhibitor. (Although not sticking to a theory), in consideration of the experimental results (described later), this step can be interpreted as "the stage of inducing differentiation into the Intestinal tract while maintaining characteristics of a stem cell". This step is important to obtain morphology (crypt-villus structures) of an intestinal organoid finally obtained and function (gene expressions of an intestinal tract marker and a drug transporter are close to those in the adult small intestine) and is the most notable characteristic of the present invention.

Typically, the cell population or a part thereof obtained through step (2) is subjected to step (3) without screening. However, an intestinal stem cell-like cell is screened from the cell population obtained through step (2), and then, step (3) may be carried out. The intestinal stem cell-like cell may be screened by a flow cytometer (cell sorter) with, for example, a cell surface marker used as an index.

The phrase "in the presence of an epidermal growth factor, a fibroblast growth factor, a TGF β receptor inhibitor, a GSK-3 β inhibitor, and a ROCK inhibitor" is the same in meaning as "in the condition of a medium containing these compounds". Thus, culture in the presence of an epidermal growth factor, a fibroblast growth factor, a TGF β receptor inhibitor, a GSK-3 β inhibitor, and a ROCK inhibitor may be carried out by using a culture medium containing these compounds.

As the fibroblast growth factor, FGF2, FGF4 or FGF10, may be employed. Two or three elements of the FGF family may be used in combination. As the TGF β receptor inhibitor, for example, A-83-01 can be used. Examples of the GSK-3 β inhibitor include CHIR99021, SB216763, CHIR98014, TWS119, Tideglusib, SB415286, BIO, AZD2858, AZD1080, AR-A014418, TDZD-8, LY2090314, IM-12, Indirubin, Bikinin, and 1-Azakenpaullone. As the ROCK inhibitor, for example, Y-27632 can be used.

The concentration of the epidermal growth factor to be added is, for example, 10 ng/mL to 500 ng/mL, and preferably, 50 ng/mL to 200 ng/mL. The concentration of the fibroblast growth factor (e.g., FGF2) to be added is, for example, 5 ng/mL to 200 ng/mL, and preferably, 20 ng/mL to 50 ng/mL. The concentration of the TGF β receptor inhibitor (e.g., A-83-01) to be added is, for example, 0.1 µM to 5 µM, and preferably, 0.3 µM to 3 µM. The concentration of the GSK-3 β inhibitor (e.g., CHIR99021) to be added is, for example, 0.5 µM to 100 µM, and preferably, 1 µM to 30 µM. The concentration of the ROCK inhibitor (e.g., Y-27632) to be added is, for example, 1 µM to 50 µM, and preferably, 3 µM to 30 µM.

Note that, if compounds different from the compounds shown as examples, i.e., FGF2, A-83-01, CHIR99021 and Y-27632, are used, the concentrations of the compounds to be added can be determined by those skilled in the art in consideration of difference in property (particularly, difference in activity) between the compounds to be used and the compounds mentioned as examples and in accordance with the above ranges of concentrations. Whether the concentration range thus determined is appropriate or not can be checked by a preliminary experiment according to Examples described later.

A serum replacement can be also used in addition to the above compounds (an epidermal growth factor, a fibroblast growth factor, a TGF β receptor inhibitor, a GSK-3 β inhibitor, and a ROCK inhibitor). In other words, culture is preferably carried out in the medium containing the above compounds and a serum replacement. The serum replacement refers to a composition to be used in place of the serum containing a differentiation inducer since, e.g., an iPS cell or an ES cell is cultured while maintaining its undifferentiated state. Preferably, Knockout serum replacement (KSR) is used. The concentration of the serum replacement (e.g., KSR) to be added is, for example, 5% (v/v) to 20% (v/v), and preferably, 5% (v/v) to 15% (v/v).

For culture in step (3), a culture vessel having a cell-adhesive culture surface is used. As the cell-adhesive culture surface, preferably, a culture surface coated with a basal membrane component (for example, laminin, type-IV collagen, entactin, vitronectin, fibronectin) or a fragment thereof, may be used. In particular, a culture surface coated with laminin 511 or an E8 fragment thereof, may be employed. As the E8 fragment of laminin 511, a product containing a highly purified recombinant thereof (recombinant human laminin 511-E8 protein) (product name: iMatrix-511, manufactured by Nippi Inc., and sold by Matrixome Inc.) is commercially available. Note that, the culture vessel is not particularly limited, for example, a dish, a flask and a multi-well plate can be used.

The period (culture period) of step (3) is, for example, 2 to 14 days, and preferably, 3 to 12 days. If the culture period is excessively short, the desired effect (induction of differentiation into a desired type of cell for forming a functional intestinal organoid having crypto-villus structures) cannot be sufficiently obtained. Note that, if a procedure for passage culture is repeated, the culture period can be extended.

In a preferred embodiment, a procedure for passage culture is carried out in step (3). More specifically, passage culture is carried out in the middle of step (3). The procedure for passage culture is considered effective particularly for purifying an intestinal epithelial stem cell-like cell (improvement in purity and uniformity) and more selectively inducing differentiation into the Intestinal tract. This is incidentally found in the experiment described later in Examples and extremely important for understanding specificity, value or significance of the invention of the present application.

The number of the procedures for passage culture is, for example, 1 to 5, preferably 1 to 3, and further preferably 1 or 2. If the number of the procedures for passage culture is excessively large, damage to a cell increases, with the result that production efficiency decreases. The procedure for passage culture may be carried out in accordance with a routine manner. For example, when cells become confluent or sub-confluent, the cells are partly picked up, transferred to another culture vessel and further cultured. In collecting cells, e.g., a cell dissociation solution may be used. As the cell dissociation solution, proteolytic enzymes such as trypsin-EDTA, collagenase IV and metalloprotease may be used alone or appropriately in combination. It is preferable to use a cell dissociation solution low in cytotoxicity. As the cell dissociation solution as mentioned above, for example, a commercially available product such as Dispase (EIDIA Co., Ltd.), TrypLE (Invitrogen) or Accutase (MILLIPORE) is available.

<Step (4) Formation of Spheroid>

In this step, the cell obtained in step (3) is cultured to form a spheroid. It is suitable to use suspension culture for forming a spheroid. In the suspension culture, usually a culture vessel having a low cell-adhesive or non cell-adhesive culture surface (obtained by treating the culture surface with, for example, a polymer material or a hydrogel or binding a polymer material or a hydrogel to the cell surface) is used. The cell is cultured away from the culture surface (in a suspension state). Examples of the culture vessel that can be used for suspension culture include, but are not particularly limited to, a dish, a flask, a multi-well plate, a tube, a tray, and a culture bag. Preferably, a culture vessel having a low cell-adhesive or non cell-adhesive culture surface in which a plurality of wells having a uniform shape and size are formed (generally referred to as a pattern plate; for example, EZSPHERE (registered trademark) manufactured by AGC TECHNO GLASS CO., LTD. and Elplasia manufactured by Kuraray Co., Ltd., can be mentioned) is used to form a plurality of spheroids at the same time. In this way, spheroids can be efficiently formed, with the result that production efficiency of an intestinal organoid is improved.

In the case of suspension culture, a cell/cell mass may be subjected to stationary culture, gyratory culture or shake culture as long as it can be maintained not to adhere to a culture surface. Preferably, suspension culture herein is carried out in a stationary state. Culture in a stationary state has many advantages, that is, a special apparatus is not required; less impact or damage to cells is expected; and the volume of a culture solution can be reduced.

The culture condition is not particularly limited as long as a spheroid can be formed. Typically, in order to form a spheroid while maintaining the characteristics of stem cells, suspension culture is carried out in the presence of an epidermal growth factor (EGF), a BMP inhibitor, and a Wnt signal activator; in other words, in a culture medium containing these components.

The epidermal growth factor to be used, is expected to produce an effect to promote cell proliferation. The BMP inhibitor to be used is expected to suppress differentiation of a stem cell and maintain the characteristics of the stem cell. The Wnt signal activator to be used is expected to proliferate a stem cell and maintain the characteristics of the stem cell.

As the BMP inhibitor, for example, Noggin can be used. As the Wnt signal activator, for example, R-spondin-1 can be used.

The concentration of the epidermal growth factor to be added is, for example, 10 ng/mL to 500 ng/mL, and preferably, 50 ng/mL to 200 ng/mL. The concentration of the BMP inhibitor (e.g., Noggin) to be added is, for example, 10 ng/mL to 500 ng/mL, and preferably, 50 ng/mL to 200 ng/mL. The concentration of the Wnt signal activator (e.g., R-spondin-1) to be added is, for example, 10 ng/mL to 1000 ng/mL, and preferably, 50 ng/mL to 500 g/mL.

Note that, if compounds different from the compounds shown as examples, i.e., Noggin, R-spondin-1, are used, the concentrations of the compounds to be added can be determined by those skilled in the art in consideration of difference in property (particularly, difference in activity) between the compounds to be used and the compounds mentioned as examples and in accordance with the above ranges of concentrations. Whether the concentration range thus determined is appropriate or not can be checked by a preliminary experiment according to Examples described later.

The period (culture period) of step (4) is, for example, 1 to 10 days, and preferably, 2 to 7 days. If the culture period is excessively short, a spheroid having a sufficient size cannot be formed. In contrast, if the culture period is excessively long, a spheroid grows more than needed, necrosis of the inner cells may occur. Preferably, a spheroid having a diameter of about 100 µm to 200 µm is formed. Spheroids of this size can be formed by use of a pattern plate in which wells having a diameter of, for example, 400 to 500 µm and a depth of 100 to 200 µm, are uniformly formed.

<Step (5) Formation of Intestinal Organoid>

In this step, the spheroid formed in step (4) is differentiated to form an intestinal organoid. In this step, it is not essential to actively induce differentiation and culture is carried out in the identical or analogous condition to that in step (4), in an embodiment (first embodiment). More specifically, culture is carried out in the presence of an epidermal growth factor, a BMP inhibitor, and a Wnt signal activator, in other words, in the medium containing these components. Examples of each compound and the concentration of each compound to be added are the same as in step (4). Note that, the period (culture period) in step (5) is, for example, 12 days to 36 days.

In order to form an intestinal organoid from a spheroid, the culture of step (5) is carried out by suspension culture. In the suspension culture in this step, a liquid medium, which is prepared by adding a material for forming a three-dimensional network structure in an aqueous solution, is preferably used, suspension culture of a plurality of spheroids formed in step (4) are simultaneously carried out (that is, a plurality of spheroids are present together in a single culture vessel). In a preferred embodiment, the whole or part (2 or more) of the spheroids formed in step (4) is subjected to suspension culture using a special liquid medium.

If the material for forming a three-dimensional network structure in an aqueous solution (hereinafter referred to as a "cohesive material") is used, spheroids can be captured or trapped by the network structure or the viscosity of the culture medium is increased to limit movement of spheroids, with the result that association or aggregation of spheroids can be prevented. Thus, a plurality of spheroids can be simultaneously cultured in a suspension state to effectively form intestinal organoids.

As the cohesive material, for example, a polymer gel and a polysaccharide can be used. Examples of the polymer gel include collagen, a polymer hydrogel, Matrigel™ (ordinary Matrigel, growth factor reduced (GFR) Matrigel, that is, Matrigel reduced in content of growth factor). Examples of the polysaccharide include gellan gum, crystalline cellulose, nanocellulose, carboxycellulose, and carboxymethyl cellulose. Two types or more materials may be used in combination.

In a preferable embodiment, a high molecular compound having an anionic functional group is used as a cohesive material. Examples of the anionic functional group include a carboxy group, a sulfone group, a phosphate group and salts of these. A carboxy group or a salt thereof is preferable. The high molecular compound that can be used in the present invention is a compound having one or two or more selected from the group consisting of the anionic functional groups. The high molecular compound to be used in the invention is not particularly limited; for example, a polysaccharide formed by polymerizing 10 or more monosaccharides (for example, triose, tetrose, pentose, hexose, heptose) is preferable, and an acid polysaccharide having an anionic functional group is more preferable. The acid polysaccharide is not particularly limited as long as it has an anionic functional group in the structure. Examples thereof include polysaccharides having uronic acid (for example, glucuronic acid, iduronic acid, galacturonic acid, mannuronic acid), polysaccharides having a sulfuric acid group or a phosphate group partly in the structure, or polysaccharides having both structures. Not only naturally obtained polysaccharides but also microbially obtained polysaccharide, polysaccharides produced by a genetic engineering method or artificially and enzymatically synthesized polysaccharides, are included. Specific examples thereof include a mixture constituted of one or two or more selected from the group consisting of hyaluronic acid, gellan gum, deacylated gellan gum, Rhamsan gum, diyutan gum, xanthan gum, carrageenan, xanthan gum, hexuronic acid, fucoidan, pectin, pectic acid, pectinic acid, heparan sulfate, heparin, heparitin sulfuric acid, kerato sulfuric acid, chondroitin sulfuric acid, dermatan sulfuric acid, rhamnan sulfuric acid and salts of these. The polysaccharide is preferably hyaluronic acid, deacylated gellan gum, diyutan gum, xanthan gum, carrageenan or any one of the salts of these. To attain an object by using a polysaccharide in a low-concentration, it is considered that deacylated gellan gum is most preferably used. Examples of the salt mentioned herein include salts of alkali metals such as lithium, sodium and potassium; salts of alkaline earth metals such as calcium, barium and magnesium; or salts of aluminum, zinc, copper, iron, ammonium, an organic base and an amino acid.

The weight-average molecular weight of the above high molecular compound (e.g., polysaccharide) is preferably 10,000 to 50,000,000, more preferably 100,000 to 20,000,000, and further preferably 1,000,000 to 10,000,000. The molecular weight can be determined, for example, based on pullulan conversion by gel permeation chromatography (GPC).

As to deacylated gellan gum, phosphorylated deacylated gellan gum can be used. A known method can be employed for phosphorylation.

In the present invention, a plurality of types of polysaccharides mentioned above can be used in combination (preferably two types). The combination of polysaccharides different in type is not particularly limited as long as association and aggregation of spheroids can be prevented; however, at least deacylated gellan gum or a salt thereof is preferably included in the combination. More specifically, examples of a suitable combination of polysaccharides include deacylated gellan gum or a salt thereof and a polysaccharide (e.g., xanthan gum, alginic acid, carrageenan, diyutan gum, methyl cellulose, locust bean gum or any one of salt of them) except deacylated gellan gum or a salt thereof. Examples of combination of polysaccharides include, but not limited to, deacylated gellan gum and Rhamsan gum; deacylated gellan gum and diyutan gum; deacylated gellan gum and xanthan gum; deacylated gellan gum and carrageenan; deacylated gellan gum and xanthan gum; deacylated gellan gum and locust bean gum; deacylated gellan gum and κ-carrageenan; deacylated gellan gum and sodium alginate; and deacylated gellan gum and methyl cellulose.

Further preferable examples of the cohesive material to be used in the present invention include hyaluronic acid, deacylated gellan gum, diyutan gum, carrageenan and xanthan gum, and salts of them. The most preferable example thereof is deacylated gellan gum or a salt thereof. As deacylated gellan gum, a commercially available one such as "KELCOGEL (registered trademark of CP Kelco) CG-LA" manufactured by Sansho Co., Ltd.; and "KELCOGEL (registered trademark of CP Kelco)" manufactured by San-Ei Gen F.F.I., Inc., can be used. As the native gellan gum, "KELCOGEL (registered trademark of CP Kelco) HT" manufactured by San-Ei Gen F.F.I., Inc. can be used. As a particularly preferable example of the cohesive material, polymer FP001 or polymer FP003 manufactured by Nissan Chemical Industries, Ltd., can be mentioned. Note that, polymer FP001 is a component of a series of 3d culture mediums FCeM (registered trademark) manufactured by Nissan Chemical Industries, Ltd.; whereas, polymer FP003 is a component of 3d culture medium FCeM (registered trademark) Advance Preparation Kit.

The amount of a cohesive material to be used, that is, the amount of the cohesive material to be added in a culture medium, is not particularly limited as long as the aforementioned desired effect can be produced; however, the amount of a cohesive material is adjusted such that the viscosity of a culture medium falls, for example, in the range of 5 mPas·s to 2000 mPas·s. If the viscosity of a culture medium is excessively low, an effect to prevent association and aggregation of spheroids cannot be obtained. Whereas, if the viscosity of a culture medium is excessively high, operability (handling) is affected (for example, recovery procedure becomes complicated) and supply of a medium component to cells may be affected. Note that, the amount of a cohesive material (e.g., Matrigel) to be used may be preferably about 1% to 10% of the amount usually used in the matrix for a three dimensional culture. The amount of deacylated gellan gum to be added in a medium may be 0.001% to 1.0% (w/v), preferably 0.003% to 0.5% (w/v), more preferably 0.005% to 0.3% (w/v), further preferably 0.01% to 0.05% (w/v), and most preferably, 0.01% to 0.03% (w/v) of the amount usually used in the medium.

Examples of the culture vessel that can be used for suspension culture include, but are not particularly limited to, a dish, a flask, a multi-well plate, a tube, a tray and a culture bag.

In another embodiment of the present invention (second embodiment), culture in step (5) is carried out in the presence of an MEK1/2 inhibitor, a DNA methylation inhibitor, a TGF β receptor inhibitor, and a γ-secretase inhibitor in addition to an epidermal growth factor, a BMP inhibitor, and a Wnt signal activator to actively induce differentiation. Use of a combination of an MEK1/2 inhibitor, a DNA methylation inhibitor, a TGF β receptor inhibitor, and a γ-secretase inhibitor, which is characteristic particularly in the present invention, increases a differentiation induction efficiency and contributes to promoting maturation of an intestinal organoid. Of the factors to be used in the second embodiment, e.g., examples and concentration of an epidermal growth factor, a BMP inhibitor, and a Wnt signal activator are the same as in the first embodiment. Thus, further explanation is omitted for brevity's sake. Whereas, examples of the MEK1/2 inhibitor include PD98059, PD184352, PD184161, PD0325901, U0126, MEK inhibitor I, MEK inhibitor II, MEK1/2 inhibitor II and SL327. Examples of the DNA methylation inhibitor include 5-aza-2'-deoxycytidine, 5-azacytidine, RG108 and zebularine. As the TGF β receptor inhibitor, preferably, an inhibitor exhibiting an inhibitory activity to at least one of TGF-β receptors ALK4, ALK5 and ALK7, may be used. For example, A-83-01, SB431542, SB-505124, SB525334, D4476, ALK5 inhibitor, LY2157299, LY364947, GW788388 and RepSox satisfy the above condition. Examples of the γ-secretase inhibitor include N-[(3,5-difluorophenyl) acetyl]-L-alanyl-2-phenyl-1, 1-dimethylethyl ester-glycine (DAPT), L-685, 458, Compound E (CAS209986-17-4), (R)-Flurbiprofen, BMS299897, JLK6, LY-411575, R04929097, MK-0752, SCP0004, SCP0025, gamma-Secretase Inhibitor XI, gamma-Secretase Inhibitor XVI, gamma-Secretase Inhibitor 1, gamma-Secretase Inhibitor VII, Semagacestat (LY450139), gamma-Secretase Inhibitor III, Compound 34, BMS-708163, Compound W, YO-01027 (Dibenzazepine) and Avagacestat (BMS-708163). Note that, not all of four types of compounds, that is, an MEK1/2 inhibitor, a DNA methylation inhibitor, a TGF β receptor inhibitor, and a γ-secretase inhibitor are added; more specifically, three types of compounds (an MEK1/2 inhibitor, a DNA methylation inhibitor, and a TGF β receptor inhibitor) except a γ-secretase inhibitor, may be added.

The concentration of an MEK1/2 inhibitor (e.g., PD98059) to be added is, for example, 4 µM to 100 µM, and preferably, 10 to 40 µM. The concentration of a DNA methylation inhibitor (e.g., 5-aza-2'-deoxycytidine) to be added is, for example, 1 µM to 25 µM, and preferably, 2.5 µM to 10 µM. The concentration of a TGF β receptor inhibitor (e.g., A-83-01) is, for example, 0.1 µM to 2.5 µM, and preferably, 0.2 µM to 1 µM. The concentration of a γ-secretase inhibitor (e.g., DAPT) to be added is, for example, 1 nM to 20 µM, and preferably, 0.1 µM to 10 µM.

Note that, if compounds different from the compounds shown as examples, i.e., PD98059, 5-aza-2'-deoxycytidine, A-83-01 and DAPT, are used, the concentrations of the compounds to be added can be determined by those skilled in the art in consideration of difference in property (particularly, difference in activity) between the compounds to be used and the compounds mentioned as examples and in accordance with the above ranges of concentrations. Whether the concentration range thus determined is appropriate or not can be checked by a preliminary experiment according to Examples described later.

In the second embodiment, preferably, as step (5), the following step (5-1) and step (5-2) are carried out in this order. In this embodiment, a combination of low-molecular compounds characteristic in step (5) (that is, a combination of an MEK1/2 inhibitor, a DNA methylation inhibitor, a TGF β receptor inhibitor, and a γ-secretase inhibitor) is used in step (5-2).

<Step (5-1)>

This step is a preliminary stage carried out before promoting active differentiation induction by a combination of four types of low-molecular compounds (an MEK1/2 inhibitor, a DNA methylation inhibitor, a TGF β receptor inhibitor, and a γ-secretase inhibitor). If this step is intervened, growth of a spheroid is promoted and a functional intestinal organoid is advantageously constructed. In this step, culture can be carried out in the same condition as in step (4) (that is, suspension culture in the presence of an epidermal growth factor, a BMP inhibitor, and a Wnt signal activator); however, preferably, a plurality of spheroids formed in step (4) are simultaneously subjected to suspension culture carried out in a liquid medium, which is prepared by adding a material (cohesive material) for forming a three-dimensional network structure to an aqueous solution, to improve operability and efficiency.

The period (culture period) of step (5-1) is, for example, 3 to 15 days, and preferably, 6 to 12 days. If the culture period is extremely short, a small spheroid is formed and cell death easily occurs. In contrast, if the culture period is extremely long, the effect produced by a low-molecular compound cannot be sufficient.

<Step (5-2)>

In this step, suspension culture is carried out in the presence of an MEK1/2 inhibitor, a DNA methylation inhibitor, a TGF β receptor inhibitor, and a γ-secretase inhibitor in addition to an epidermal growth factor, a BMP inhibitor, and a Wnt signal activator, with the result that active differentiation induction is promoted to form an intestinal organoid. Since the culture condition is the same as in the above step (5-1), further explanation is omitted for brevity's sake.

The period (culture period) of step (5-2) is, for example, 3 to 21 days, and preferably, 9 to 18 days. If the culture period is excessively short, functional improvement is not sufficient. In contrast, if the culture period is excessively long, a spheroid may be damaged, leading to cell death.

In another embodiment (third embodiment) of the present invention, the culture of step (5) is carried out in the presence of an MEK1/2 inhibitor, a DNA methylation inhibitor, a TGF β receptor inhibitor, and an epidermal growth factor (EGF) (the condition will be hereinafter referred to as a "first condition") and in the condition where cAMP is supplied to a cell (the condition will be hereinafter referred to as a "second condition") to carry out active differentiation induction. Since the first condition is the same as in the above second embodiment, further explanation is omitted for brevity's sake. In contrast, the second condition, in other words, the condition where cAMP is supplied to a cell, is equivalent to the condition where a compound that can be taken up into a cell and then serves as cAMP inside the cell is present. Thus, in order to satisfy the second condition, a culture medium containing, for example, a cAMP derivative which can be taken up into a cell, may be used. Examples of the cAMP derivative to be employed include a PKA activator (for example, 8-Br-cAMP (8-Bromoadenosine-3',5'-cyclic monophosphate sodium salt, CAS Number: 76939-46-3), 6-Bnz-cAMP (N6-Benzoyladenosine-3',5'-cyclic monophosphate sodium salt, CAS Number: 1135306-29-4), cAMPS-Rp ((R)-Adenosine, cyclic 3',5'-(hydrogenphosphorothioate) triethylammonium salt, CAS Number: 151837-09-1), cAMPS-Sp ((S)-Adenosine, cyclic 3',5'-(hydrogenphosphorothioate) triethylammonium salt, CAS Number: 93602-66-5), Dibutyryl-cAMP (N6,02'-Dibutyryl adenosine 3',5'-cyclic monophosphate sodium salt, CAS Number: 16980-89-5), 8-Cl-cAMP (8-Chloroadenosine-3',5'-cyclic monophosphate salt, CAS Number: 124705-03-9)), Epac activator (Rp-8-Br-cAMPS (8-Bromoadenosine 3',5'-cyclic Monophosphothioate, Rp-Isomer. Sodium salt, CAS Number: 129735-00-8), 8-CPT-cAMP (8-(4-Chlorophenylthio)adenosine 3',5'-cyclic monophosphate, CAS Number: 93882-12-3) and 8-pCPT-2'-O-Me-cAMP (8-(4-Chlorophenylthio)-2'-O-methyladenosine 3',5'-cyclic monophosphate monosodium, CAS Number: 634207-53-7)). The concentration of the cAMP derivative (e.g., 8-Br-cAMP) to be added is, for example, 0.1 mM to 10 mM, preferably 0.2 mM to 5 mM, and further preferably, 0.5 mM to 2 mM. Note that, if compounds different from the compound shown as an example, i.e., 8-Br-cAMP, are used, the concentrations of the compounds to be added can be determined by those skilled in the art in consideration of difference in property (particularly, difference in activity) between the compounds to be used and the compound (8-Br-cAMP) shown as an example, and in accordance with the above ranges of concentrations. Whether the concentration range thus determined is appropriate or not can be checked by a preliminary experiment according to Examples described later.

In a third embodiment, preferably, any one of the following culture steps A to C is carried out as step (5).

<Culture Step A>

In culture step A, culture is carried out in the presence of (a-1) an MEK1/2 inhibitor, a DNA methylation inhibitor, a TGF β receptor inhibitor, and an epidermal growth factor, and subsequently in the presence of (a-2) an MEK1/2 inhibitor, a DNA methylation inhibitor, a TGF β receptor inhibitor, and an epidermal growth factor, and in the condition where cAMP can be supplied to a cell. In short, two culture stages different in the presence or absence of the condition where cAMP is supplied to a cell is carried out. If so, differentiation into an intestinal epithelial cell can be promoted, and maturation into an intestinal epithelial cell and acquisition of function thereof can be effectively obtained. The culture period (a-1) is, for example, 1 to 5 days. The culture period (a-2) is, for example, 3 to 15 days. Note that, to the matters (e.g., compounds that can be used for each culture and the concentration thereof to be added) not particularly described, the corresponding explanation to the above is applied.

The culture (a-2) may be carried out in the presence of a cAMP-degrading enzyme inhibitor in addition to an MEK1/2 inhibitor, a DNA methylation inhibitor, a TGF β receptor inhibitor, and an epidermal growth factor. If this condition is employed, degradation of cAMP is inhibited to suppress a decrease of an intracellular cAMP concentration. As a result, it can be expected that differentiation induction into the intestinal epithelium is promoted, particularly acquisition of function as an intestinal epithelial cell is promoted. In short, the condition is advantageous to preparation for a (more) functional intestinal organoid. Examples of the cAMP-degrading enzyme inhibitor include IBMX (3-isobutyl-1-methylxanthine) (MIX), Theophylline, Papaverine, Pentoxifylline (Trental), KS-505, 8-Methoxymethyl-IBMX, Vinpocetine (TCV-3B), EHNA, Trequinsin (HL-725), Lixazinone (RS-82856), (LY-186126), Cilostamide (OPC 3689), Bemoradan (RWJ-22867), Anergrelide (BL4162A), Indolidan (LY195115), Cilostazol (OPC-13013), Milrinone (WIN47203), Siguazodan (SKF-94836), 5-Methyl-imazodan (CI 930), SKF-95654, Pirilobendan (UD-CG 115 BS), Enoximone (MDL 17043), Imazodan (CL 914), SKF-94120, Vesnarinone (OPC 8212), Rolipram (Ro-20-1724), (ZK-62711), Denbufyll'ine, Zaprinast (M&B-22, 948), Dipyridamole, Zaprinast (M&B-22, 948), Dipyridamole, Zardaverine, AH-21-132, and Sulmazol (AR-L 115 BS). The concentration of the cAMP-degrading enzyme inhibitor (e.g., IBMX) to be added is, for example, 0.05 mM to 5 mM, preferably, 0.1 mM to 3 mM, and further preferably 0.2 mM to 1 mM. Note that, if compounds different from the compound shown as an example, i.e., IBMX, are used, the concentrations of the compounds to be added can be determined by those skilled in the art in consideration of difference in property (particularly, difference in activity) between the compounds to be used and the compounds mentioned as examples and in accordance with the above ranges of concentrations. Whether the concentration range thus determined is appropriate or not can be checked by a preliminary experiment according to Examples described later.

After the culture (a-2), culture (culture (a-3)) in the presence of an MEK1/2 inhibitor, a DNA methylation inhibitor, a TGF β receptor inhibitor, and an epidermal growth factor, may be carried out. The period of the culture is specified as, for example, 1 to 10 days. If this culture is carried out, that differentiation into an intestinal epithelial cell can be promoted, and maturation into an intestinal epithelial cell and acquisition of function thereof can be effectively obtained.

<Culture Step B>

In culture step B, culture (b-1) in the presence of an MEK1/2 inhibitor, a DNA methylation inhibitor, a TGF β receptor inhibitor, and an epidermal growth factor and in the condition where cAMP is supplied to a cell is carried out; and subsequently, culture (b-2) in the presence of an MEK1/2 inhibitor, a DNA methylation inhibitor, a TGF β receptor inhibitor, an epidermal growth factor, and a cAMP-degrading enzyme inhibitor is carried out. If culture is carried out in the condition where a cAMP is supplied to a cell, and subsequently, in the presence of a cAMP-degrading enzyme inhibitor in this manner, differentiation into an intestinal epithelial cell can be promoted, and maturation into an intestinal epithelial cell and acquisition of function thereof can be effectively obtained. The period of culture (b-1) is, for example, 3 to 15 days. The period of culture (b-2) is, for example, 3 to 15 days. Note that, to the matters (e.g., compounds that can be used for each culture and the concentration thereof to be added) not particularly described, the corresponding explanation to the above is applied.

The culture (b-1) may be carried out in the presence of a cAMP-degrading enzyme inhibitor in addition to an MEK1/2 inhibitor, a DNA methylation inhibitor, a TGF β receptor inhibitor, and an epidermal growth factor. If the condition is employed, a decrease of the intracellular cAMP concentration can be suppressed from the early stage. As a result, it is expected that induction of differentiation into the intestinal epithelium, in particular, acquisition of function as the intestinal epithelial cells is promoted. In other words, the condition is advantageous to effective preparation of a (more) functional intestinal organoid.

After culture (b-2), culture (b-3) in the presence of an MEK1/2 inhibitor, a DNA methylation inhibitor, a TGF β receptor inhibitor, and an epidermal growth factor, may be carried out. The period of the culture is, for example, 1 to 10 days. If this culture is carried out, differentiation into an intestinal epithelial cell can be promoted, and maturation into an intestinal epithelial cell and acquisition of function thereof can be effectively obtained.

<Culture Step C>

In culture step C, culture (c-1) in the presence of an MEK1/2 inhibitor, a DNA methylation inhibitor, a TGF β receptor inhibitor, and an epidermal growth factor, and in the condition where cAMP is supplied to a cell, is carried out. The period of culture (c-1) is, for example, 3 to 15 days. Note that, to the matters (e.g., compounds that can be used for each culture and the concentration thereof to be added) not particularly described, the corresponding explanation to the above is applied.

The culture (c-1) may be carried out in the presence of a cAMP-degrading enzyme inhibitor (the condition where cAMP is supplied to a cell may be used in combination) in addition to an MEK1/2 inhibitor, a DNA methylation inhibitor, a TGF β receptor inhibitor, and an epidermal growth factor. If the condition is employed, it is possible to suppress a decrease of the intracellular cAMP concentration while cAMP is supplied to a cell. Thus, the condition is effective for maintaining the intracellular cAMP at a high level and efficient differentiation induction into an intestinal epithelial cell can be expected.

After culture (c-1), culture (c-2) in the presence of an MEK1/2 inhibitor, a DNA methylation inhibitor, a TGF β receptor inhibitor, and an epidermal growth factor, may be carried out. The period of the culture is, for example, 1 to 10 days. If the culture is carried out, differentiation into an intestinal epithelial cell can be promoted, and maturation into an intestinal epithelial cell and acquisition of function thereof can be effectively obtained.

In another embodiment (fourth embodiment) of present invention, culture of step (5) may be carried out by using an MEK1/2 inhibitor, a DNA methylation inhibitor, a TGF β receptor inhibitor, an epidermal growth factor, and a cAMP activation substance in combination to induce active differentiation. In the differentiation induction, if a cAMP activation substance is used, the intracellular cAMP level is aggressively enhanced. The phrase "using an MEK1/2 inhibitor, a DNA methylation inhibitor, a TGF β receptor inhibitor, an epidermal growth factor, and a cAMP activation substance in combination" means that all of these compounds are required for carrying out at least one of culture processes constituting step (5) and does not means that all of these compounds are simultaneously used; in other words, using a medium containing all of these compounds is not essential condition for culturing.

In the fourth embodiment, step (5) is constituted of at least one culture process (details will be described later). In individual culture processes constituting step (5), for example, a culture medium containing an epidermal growth factor and a cAMP activation substance as essential components; a culture medium containing an MEK1/2 inhibitor, a DNA methylation inhibitor, a TGF β receptor inhibitor, and an epidermal growth factor as essential components; a culture medium containing an epidermal growth factor as an essential component; or a culture medium containing an MEK1/2 inhibitor, a DNA methylation inhibitor, a TGF β receptor inhibitor, an epidermal growth factor, and a cAMP activation substance as essential components, is used.

Since the MEK1/2 inhibitor, DNA methylation inhibitor, TGF β receptor inhibitor, and epidermal growth factor are the same as those of condition 1 in the third embodiment, further explanation is omitted for brevity's sake. Examples of the cAMP activation substance that can be used include forskolin, indomethacin, NKH477 (colforsin daropate), a cell-derived toxin protein (pertussis toxin, cholera toxin), PACAP-27, PACAP-38, and SKF83822. Forskolin exhibits an adenylate cyclase activating action and promotes synthesis intracellular cAMP. The concentration of the cAMP activation substance (e.g., forskolin) to be added is, for example, 1 μM to 200 μM, and preferably, 5 μM to 100 μM. Note that, if compounds different from the compound shown as an example, i.e., forskolin, are used, the concentrations of the compounds to be added can be determined by those skilled in the art in consideration of difference in property (particularly, difference in activity) between the compounds to be used and the compound (forskolin) shown as an example and in accordance with the above ranges of concentrations. Whether the concentration range thus determined is appropriate or not can be checked by a preliminary experiment according to Examples described later.

In the fourth embodiment, step (5) may be carried out in the condition where cAMP is supplied to a cell (referred to as "additional condition 1"), and the condition where a cAMP-degrading enzyme inhibitor is present (referred to as "additional condition 2") or in either one of these conditions, in addition to the aforementioned conditions. Additional condition 1 is equivalent to the first condition of the third embodiment. Additional condition 2 is equivalent to the condition that can be employed in culture steps A to C in the third embodiment.

In the fourth embodiment, preferably, any one of the following culture processes A to D is carried out as step (5)

<Culture Step A>

In culture step A, (a-1) culture in the presence of an epidermal growth factor and an intracellular cAMP synthetic accelerator is carried out, and subsequently, (a-2) culture in the presence of an MEK1/2 inhibitor, a DNA methylation inhibitor, a TGF β receptor inhibitor, and an epidermal growth factor are carried out. If a two-stage culture is carried out in this way, it is expected that differentiation into an intestinal epithelial cell can be promoted, and maturation into an intestinal epithelial cell and acquisition of function thereof can be effectively obtained. The period of culture (a-1) is, for example, 2 to 10 days, and preferably, 4 to 8 days. The period of culture (a-2) is, for example, 9 to 29 days, and preferably, 7 to 27 days. Note that, to the matters (e.g., compounds that can be used for each culture and the concentration thereof to be added) not particularly described, the corresponding explanation to the above is applied.

Culture (a-1) may be carried out in the condition where cAMP is supplied to a cell (referred to as "additional condition 1"), and in the conditions where a cAMP-degrading enzyme inhibitor is present (referred to as "additional condition 2"), or in either one of these conditions. The same applied to Culture (a-2). The details of additional condition 1 and additional condition 2 are the same as mentioned above.

<Culture Step B>

In culture step B, (b-1) culture in the presence of an epidermal growth factor is carried out, and subsequently, (b-2) culture in the presence of an MEK1/2 inhibitor, a DNA methylation inhibitor, a TGF β receptor inhibitor, an epidermal growth factor and an intracellular cAMP synthetic accelerator are carried out. If a two-stage culture is carried out in this way, it is expected that differentiation into an intestinal epithelial cell can be promoted, and maturation into an intestinal epithelial cell and acquisition of function thereof can be effectively obtained. The period of culture (b-1) is, for example, 2 to 10 days, and preferably, 4 to 8 days. The period of culture (b-2) is, for example, 9 to 19 days, and preferably, 7 to 17 days. Note that, to the matters (e.g., compounds that can be used for each culture and the concentration thereof to be added) not particularly described, the corresponding explanation to the above is applied.

Culture (b-1) may be carried out in the condition where cAMP is supplied to a cell (referred to as "additional condition 1"), and in the conditions where a cAMP-degrading enzyme inhibitor is present (referred to as "additional condition 2"), or in either one of these conditions. The same applied to Culture (b-2). The details of additional condition 1 and additional condition 2 are the same as mentioned above.

After culture (b-2), culture in the presence of an MEK1/2 inhibitor, a DNA methylation inhibitor, a TGF β receptor inhibitor, and an epidermal growth factor (culture (b-3)) may be carried out. The period of the culture is specified as, for example, 1 to 10 days. If this culture is carried out, it is expected that differentiation into an intestinal epithelial cell can be promoted, and maturation into an intestinal epithelial cell and acquisition of function thereof can be effectively obtained.

<Culture Step C>

In culture step C, culture in the presence of an epidermal growth factor and intracellular cAMP synthetic accelerator (c-1) is carried out, and subsequently, culture (c-2) in the presence of an MEK1/2 inhibitor, a DNA methylation inhibitor, a TGF β receptor inhibitor, an epidermal growth factor, and a intracellular cAMP synthetic accelerator, is carried out. If a two-stage culture is carried out in this way, it is expected that differentiation into an intestinal epithelial cell can be promoted, and maturation into an intestinal epithelial cell and acquisition of function thereof can be effectively obtained. The period of culture (c-1) is, for example, 2 to 10 days, and preferably, 4 to 8 days. The period of culture (c-2) is, for example, 9 to 19 days, and preferably, 7 to 17 days. Note that, to the matters (e.g., compounds that can be used for each culture and the concentration thereof to be added) not particularly described, the corresponding explanation to the above is applied.

Culture (c-1) may be carried out in the condition where cAMP is supplied to a cell (referred to as "additional condition 1"), and in the conditions where a cAMP-degrading enzyme inhibitor is present (referred to as "additional condition 2"), or in either one of these conditions. The same applied to culture (c-2). The details of additional condition 1 and additional condition 2 are the same as mentioned above.

After culture (c-2), culture in the presence of an MEK1/2 inhibitor, a DNA methylation inhibitor, a TGF β receptor inhibitor, and an epidermal growth factor (culture (c-3)) may be carried out. The period of the culture is, for example, 1 to 10 days. If this culture is carried out, it is expected that differentiation into an intestinal epithelial cell can be promoted, and maturation into an intestinal epithelial cell and acquisition of function thereof can be effectively obtained.

<Culture Step D>

In culture step D, (d-1) culture in the presence of an MEK1/2 inhibitor, a DNA methylation inhibitor, a TGF receptor inhibitor, epidermal growth factor and intracellular cAMP synthetic accelerator is carried out. The culture step is particularly advantageous because the culture procedure is simple; and differentiation into an intestinal epithelial cell is effectively carried out. In addition, due to compounds, an effect can be desirably and stably obtained. The period of culture (d-1) is, for example, 15 to 25 days, and preferably, 17 to 23 days. Note that, to the matters (e.g., compounds that can be used for each culture and the concentration thereof to be added) not particularly described, the corresponding explanation to the above is applied.

Culture (d-1) may be carried out in the condition where cAMP is supplied to a cell (referred to as "additional condition 1"), and in the conditions where a cAMP-degrading enzyme inhibitor is present (referred to as "additional condition 2"), or in either one of these conditions. The details of additional condition 1 and additional condition 2 are the same as mentioned above.

After culture (d-1), culture in the presence of an MEK1/2 inhibitor, a DNA methylation inhibitor, a TGF β receptor inhibitor, and an epidermal growth factor (culture (d-2)) may be carried out. The period of the culture is specified as, for example, 1 to 10 days. If this culture is carried out, it is expected that differentiation into an intestinal epithelial cell can be promoted, and maturation into an intestinal epithelial cell and acquisition of function thereof can be effectively obtained.

The other culture conditions (e.g., culture temperature) to be employed in individual steps constituting the present invention should be the same conditions routinely employed in culture for animal cells. More specifically, culture may be carried out, for example, at 37° C., in an environment of 5% $CO_2$. Examples of a base medium that can be used include Iscove's Modified Dulbecco Medium (IMDM) (e.g., GIBCO), Ham F12 medium (HamF12) (e.g., SIGMA, Gibco), Dulbecco's modified Eagle's Medium (D-MEM) (e.g., Nacalai Tesque Inc., Sigma, Gibco), Glasgow Minimum Essential Medium (e.g., Gibco) and RPMI1640 medium. At least two types of base mediums may be used in combination. In step (4) and step (5), it is preferable to use a base medium (for example, a mixed medium of D-MEM and Ham F12 medium, D-MEM) suitable for culturing epithelial cells. Examples of components that can be added to a culture medium include bovine serum albumin (BSA), an antibiotic substance, 2-mercapto ethanol, PVA, a non-essential amino acid (NEAA), insulin, transferrin and selenium.

In the middle of step (1) and step (2) constituting the present invention, passage culture may be carried out. For example cells that become confluent or sub-confluent are partly taken and transferred to another culture vessel and subsequently cultured. In collecting cells, e.g., a cell dissociation solution may be used. As the cell dissociation solution, proteolytic enzymes such as trypsin-EDTA, collagenase IV and metalloprotease, can be used alone or appropriately in combination. It is preferable to use a cell dissociation solution low in cytotoxicity. As the cell dissociation solution low in cytotoxicity, a commercially available product such as Dispase (EIDIA Co., Ltd.), TrypLE (Invitrogen) or Accutase (MILLIPORE), can be used. The cells recovered may be processed by e.g., a cell strainer so as to obtain a dispersion (discrete) state, and then, subjected to passage culture. In individual steps constituting the present invention, if necessary, medium exchange is carried out, for example, at a frequency once per 24 hours to 3 days.

As described above, in step (3), it is preferable to carry out passage culture. In step (5), passage culture can be carried out, for example, 1 to 5 times. In this case, procedure for passage culture may be carried out, for example, in accordance with the following procedure. First, cell mass (spheroids) is recovered, if necessary, washed and treated with a dispersion/dissociation solution for spheroids (for example, EDTA of Thermo Fisher Scientific, Dispase II of Roche or Gentle Cell Dissociation Reagent of STEMCELL Technologies). Subsequently, the spheroids are dispersed or suspended by, e.g., pipetting, and then, seeded and subsequently cultured.

For collecting cells at the time of passage culture and medium exchange, it is desirable that the cells are previously treated with a ROCK (Rho-associated coiled-coil forming kinase/Rho binding kinase) inhibitor such as Y-27632, in order to suppress cell death.

According to the present invention described above, an intestinal organoid having a structure close to the structure of the Intestinal tract of a living body, in other words, a budding intestinal organoid, can be prepared. The intestinal organoid of the present invention is analogous not only in structure but also in function to the Intestinal tract of a living body and has a pharmacokinetic function specific to the Intestinal tract, more specifically, a metabolic function (absorption, efflux). Whether an intestinal organoid has such a function or not can be evaluated based on, e.g., expressions of various transporters (e.g., peptide transporter, efflux transporter, organic anion transporter) and expressions/activities of drug-metabolizing enzymes. The presence or absence and degree of drug response are useful as indexes for evaluating the functions of an intestinal organoid. Examples of the peptide transporter include SLC15A1/PEPT1 (SLC (solute carrier) family member 15A1/peptide transporter 1). Examples of the efflux transporter include ABCB1/MDR1

(ATP-binding cassette transporter B1/multi-drug resistant protein 1), ABCC2/MRP2 (ATP-binding cassette transporter C2/multi-drug resistance associated protein 2) and ABCG2/BCRP (ATP-binding cassette transporter G2/breast cancer resistant protein). Examples of the organic anion transporter include SLCO2B1/OATP2B1 (SLC (solute carrier) organic anion transporter 2B1). Examples of the drug-metabolizing enzyme include CYP3A4 (cytochrome P450 3A4) and CYP3A8 (cytochrome P450 3A8). Drug response can be evaluated based on induction of expression of, e.g., a drug-metabolizing enzyme CYP3A (for example, CYP3A4 in the case of a human, CYP3A8 in the case of cynomolgus monkey) via rifampicin or vitamin D receptor.

Note that, e.g., CDX2 (Caudal-type homeobox 2), Chromogranin A, E-cad (E-cadherin; epithelial cadherin), LGR5 (leucine rich repeat-containing G protein-conjugated receptor), Lysozyme, MUC2 (mucin 2 glycoprotein), OLFM4 (Olfactmedin 4), Villin and Vim (Vimentin) are also useful for evaluating the structure or function of an intestinal organoid.

2. Method for Preparing Intestinal Tract Cell Layer

According to another aspect of the present invention, there is provided a method for preparing an intestinal tract cell layer having analogous characteristics to the intestinal tract tissue of a living body (hereinafter also referred to as "the intestinal tract cell layer preparation method of the present invention"). The intestinal tract cell layer preparation method of the present invention employs an intestinal organoid obtained in accordance with the above aspect; more specifically, the intestinal organoid is subjected to plane culture (that is, transfer/conversion to a two dimensional culture system) to form a cell layer. More specifically, the intestinal tract cell layer preparation method of the present invention is characterized by the following steps of (1) to (6):

(1) differentiating a pluripotent stem cell into an endoderm-like cell;
(2) differentiating the endoderm-like cell obtained in step (1) into an intestinal stem cell-like cell;
(3) culturing the intestinal stem cell-like cell obtained in step (2) in the presence of an epidermal growth factor, a fibroblast growth factor, a TGF β receptor inhibitor, a GSK-3 β inhibitor, and a ROCK inhibitor;
(4) culturing the cell obtained in step (3) to form a spheroid;
(5) differentiating the spheroid formed in step (4) to form an intestinal organoid, wherein the differentiation includes culturing in the presence of an epidermal growth factor, a BMP inhibitor, and a Wnt signal activator; and
(6) subjecting the cells constituting the intestinal organoid formed in step (5) to plane culture carried out in the presence of an epidermal growth factor and a TGF β receptor inhibitor.

Since steps (1) to (5) are the same as those of the first aspect, further explanation is omitted for brevity's sake. In step (6) following step (5), cells constituting the intestinal organoid formed in step (5) are subjected to plane culture in the presence of an epidermal growth factor and a TGF β receptor inhibitor. In other words, cells are collected from the intestinal organoid formed, transferred to a two-dimensional culture system and cultured in a predetermined condition. Typically, the whole or part of a cell population collected from an intestinal organoid is subjected to plane culture without sorting. For collecting cells from an intestinal organoid, e.g., a cell dissociation solution is desirably used. As the cell dissociation solution, proteolytic enzymes such as trypsin-EDTA, collagenase IV and metalloprotease can be used alone or appropriately in combination. A cell dissociation solution low in cytotoxicity is preferable. As the cell dissociation solution low in cytotoxicity, a commercially available product such as Dispase (EIDIA Co., Ltd.), TrypLE (Invitrogen) or Accutase (MILLIPORE) can be used. The cells recovered may be processed by e.g., a cell strainer to increase dispersiveness (degree of dispersion) of cells. Note that, for collecting cells, it is desirable that the cells are previously treated with a ROCK (Rho-associated coiled-coil forming kinase/Rho binding kinase) inhibitor such as Y-27632, in order to suppress cell death.

The culture condition of step (6): "in the presence of an epidermal growth factor and a TGF β receptor inhibitor" is the same in meaning as in the condition containing these compounds in the medium. Thus, culture in the presence of an epidermal growth factor and a TGF β receptor inhibitor may be carried out in a culture medium containing these compounds. As the TGF β receptor inhibitor, for example, A-83-01 can be used.

The concentration of the epidermal growth factor to be added is, for example, 10 ng/mL to 500 ng/mL, and preferably, 50 ng/mL to 200 ng/mL. The concentration of the TGF β receptor inhibitor (e.g., A-83-01) to be added is, for example, 0.1 μM to 5 μM, and preferably, 0.3 μM to 3 μM. Note that, if compounds different from the compound shown as an example, i.e., A-83-01, are used, the concentrations of the compounds to be added can be determined by those skilled in the art in consideration of difference in property (particularly, difference in activity) between the compounds to be used and the compound mentioned as an example and in accordance with the above ranges of concentrations. Whether the concentration range thus determined is appropriate or not can be checked by a preliminary experiment according to Examples described later.

The culture of step (6) is carried out preferably in the presence of a cAMP activation substance in addition to an epidermal growth factor and a TGF β receptor inhibitor to enhance the function of the cell layer to be formed. Further preferably, not only a cAMP activation substance but also a y-secretase inhibitor, and/or a GSK-3 β inhibitor are added to further enhance the function of the cell layer to be formed.

Examples of the cAMP activation substance that can be used include forskolin, indomethacin, NKH477 (colforsin daropate), a cell-derived toxin protein (pertussis toxin, cholera toxin), PACAP-27, PACAP-38 and SKF83822. Examples of the y-secretase inhibitor include N-[(3,5-difluorophenyl) acetyl]-L-alanyl-2-phenyl-1,1-dimethylethyl-ester-glycine (DAPT), L-685, 458, Compound E (CAS209986-17-4), (R)-Flurbiprofen, BMS299897, JLK6, LY-411575, R04929097, MK-0752, SCP0004, SCP0025, gamma-Secretase Inhibitor XI, gamma-Secretase Inhibitor XVI, gamma-Secretase Inhibitor I, gamma-Secretase Inhibitor VII, Semagacestat (LY450139), gamma-Secretase Inhibitor III, Compound 34, BMS-708163, Compound W, YO-01027 (Dibenzazepine) and Avagacestat (BMS-708163). Examples of the GSK-3 β inhibitor include CHIR99021, SB216763, CHIR98014, TWS119, Tideglusib, SB415286, BIO, AZD2858, AZD1080, AR-A014418, TDZD-8, LY2090314, IM-12, Indirubin, Bikinin and 1-Azakenpaullone.

The concentration of the cAMP activation substance (e.g., forskolin) to be added is, for example, 1 μM to 200 μM, and preferably, 5 μM to 100 μM. The concentration of the y-secretase inhibitor (e.g., DAPT) to be added is, for example, 1 nM to 20 μM, and preferably, 0.1 μM to 10 μM. The concentration of the GSK-3 β inhibitor (e.g., CHIR99021) to be added is, for example, 0.5 µM to 100 µM, and preferably, 1 µM to 30 µM. Note that, if compounds different from the compounds shown as examples, i.e., forskolin, DAPT, CHIR99021, are used, the concentrations of the compounds to be added can be determined by those skilled in the art in consideration of difference in property (particularly, difference in activity) between the compounds to be used and the compounds shown as examples and in accordance with the above ranges of concentrations. Whether the concentration range thus determined is appropriate or not can be checked by a preliminary experiment according to Examples described later.

For culture in step (6), a culture vessel having a cell-adhesive culture surface is used. As the cell-adhesive culture surface, preferably, a culture surface coated with a basal membrane component (for example, laminin, type-IV collagen, entactin, vitronectin, fibronectin) or a fragment thereof, may be used. In particular, a culture surface coated with laminin 511 or an E8 fragment thereof, is desirably employed. As the E8 fragment of laminin 511, a product obtained by highly purifying a recombinant thereof (recombinant human laminin 511-E8 protein) (product name: iMatrix-511, manufactured by Nippi Inc., and sold by Matrixome Inc.) is commercially available. Note that, the culture vessel is not particularly limited, for example, a dish, a flask and a multi-well plate can be used.

In an embodiment, cells are cultured on a semi-permeable membrane (porous membrane) to form a cell layer. More specifically, a culture vessel having an insert (for example, Transwell (registered trademark) provided by Corning Incorporated) is used. Cells are seeded in the insert and cultured to obtain a cell layer. According to the embodiment, a cell layer suitable for an evaluation system in which a test substance passed through the cell layer is quantified, can be obtained. Note that, how to construct the evaluation system and how to use the system will be described later (4. Use of intestinal tract cell layer).

In a preferable embodiment, at least a part of the plane culture in step (6) is carried out by air-liquid interface culture. For example, after cells are seeded on a semi-permeable membrane. After cells adhere to a culture surface (that is, the semi-permeable membrane), air-liquid interface culture is partly initiated. Preferably, after it is confirmed that a cell layer is formed, switching to air-liquid interface culture is carried out. The timing of switching to air-liquid interface culture is roughly about 3 hours to 3 days (for example, 6 hours, 8 hours, 12 hours, 24 hours, 36 hours, 48 hours, 60 hours) after seeding. Since time required for adhesion of cells to a culture surface and time required for formation of a cell layer may vary depending on the state of cells and other conditions (for example, culture medium to be used), the timing for switching to air-liquid interface culture may be determined by carrying out a preliminary experiment. Alternatively, appropriate timing for switching to air-liquid interface culture may be determined by careful watching the cells after seeding.

The term "air-liquid interface culture" refers to culturing cells in the state where the entire cell surface (except a site in contact with the culture surface and a site in contact with or adhering to other cells) is not in contact with a medium, that is, a part of the cell surface is in contact with a gas phase. For example, if a culture vessel having an insert as mentioned above (typically, constituted of an insert and a well plate supporting the insert) is used, cells are seeded in the insert and allowed to adhere to the insert (preferably, after a cell layer is formed), and then, the culture solution within the insert is removed. If so, a gas phase will be present at the upper side of the cells; whereas, a liquid phase (culture medium) will be present at the lower side of the cells (that is, the side of the cells adhering to the insert). In this state, air-liquid interface culture can be initiated. In place of removing the culture solution within the insert, the culture solution in wells may be removed to form the state where a gas phase is present at the upper side of the cells; whereas, a liquid phase is present at the lower side of the cells. In this state, a air-liquid interface culture can be carried out.

The air-liquid interface culture is desirably carried out in the presence of a factor activating a cAMP signal in addition to an epidermal growth factor and a TGF β receptor inhibitor, that is, in a culture medium containing these three types of substances. As the factor activating a cAMP signal, a cAMP derivative, a cAMP-degrading enzyme inhibitor or a cAMP activation substance can be used. At least two substances of these may be used in combination.

Examples of the cAMP derivative that can be employed include a PKA activator (e.g., 8-Br-cAMP (8-Bromoadenosine-3',5'-cyclic monophosphate sodium salt, CAS Number: 76939-46-3), 6-Bnz-cAMP (N6-Benzoyladenosine-3',5'-cyclic monophosphate sodium salt, CAS Number: 1135306-29-4), cAMPS-Rp ((R)-Adenosine, cyclic 3',5'-(hydrogenphosphorothioate) triethylammonium salt, CAS Number: 151837-09-1), cAMPS-Sp ((S)-Adenosine, cyclic 3',5'-(hydrogenphosphorothioate) triethylammonium salt, CAS Number: 93602-66-5), Dibutyryl-cAMP (N6, 02'-Dibutyryl adenosine 3',5'-cyclic monophosphate sodium salt, CAS Number: 16980-89-5), 8-Cl-cAMP (8-Chloroadenosine-3', 5'-cyclic monophosphate salt, CAS Number: 124705-03-9)); and an Epac activator (e.g., Rp-8-Br-cAMPS (8-Bromoadenosine 3',5'-cyclic Monophosphothioate, Rp-Isomer. sodium salt, CAS Number: 129735-00-8), 8-CPT-cAMP (8-(4-Chlorophenylthio)adenosine 3',5'-cyclic monophosphate, CAS Number: 93882-12-3), 8-pCPT-2'-O-Me-cAMP (8-(4-Chlorophenylthio)-2'-O-methyladenosine 3',5'-cyclic monophosphate monosodium, CAS Number: 634207-53-7)). The concentration of the cAMP derivative (e.g., 8-Br-cAMP) to be added is, for example, 0.1 mM to 10 mM, preferably, 0.2 mM to 5 mM, and further preferably 0.5 mM to 2 mM. Note that, if compounds different from the compound shown as an example, i.e., 8-Br-cAMP, are used, the concentration of the compounds to be added can be determined by those skilled in the art in consideration of difference in property (particularly, difference in activity) between the compounds to be used and the compound (8-Br-cAMP) mentioned as an example and in accordance with the above ranges of concentrations. Whether the concentration range thus determined is appropriate or not can be checked by a preliminary experiment according to Examples described later.

Examples of the cAMP-degrading enzyme inhibitor include IBMX (3-isobutyl-1-methylxanthine) (MIX), Theophylline, Papaverine, Pentoxifylline (Trental), KS-505, 8-Methoxymethyl-IBMX, Vinpocetine (TCV-3B), EHNA, Trequinsin (HL-725), Lixazinone (RS-82856), (LY-186126), Cilostamide (OPC3689), Bemoradan (RWJ-22867), Anergrelide (BL4162A), Indolidan (LY195115), Cilostazol (OPC-13013), Milrinone (WIN47203), Siguazodan (SKF-94836), 5-Methyl-imazodan (CI930), SKF-95654, Pirilobendan (UD-CG 115 BS), Enoximone (MDL 17043), Imazodan (CL 914), SKF-94120, Vesnarinone (OPC 8212), Rolipram (Ro-20-1724), (ZK-62711), Denbufyll'ine, Zaprinast (M&B-22, 948), Dipyridamole, Zaprinast (M&B-22, 948), Dipyridamole, Zardaverine, AH-21-132 and Sulmazol (AR-L 115 BS). The concentration of the cAMP-degrading enzyme inhibitor (e.g., IBMX) to be added is, for example, 0.05 mM to 5 mM, preferably, 0.1 mM to 3 mM, and further preferably, 0.2 mM to 1 mM. Note that, if compounds different from the compound shown as an example, i.e., IBMX, are used, the concentrations of the compounds to be added can be determined by those skilled in the art in consideration of difference in property (particularly, difference in activity) between the compounds to be used and the compound (IBMX) mentioned as an example and in accordance with the above ranges of concentrations. Whether the concentration range thus determined is appropriate or not can be checked by a preliminary experiment according to Examples described later.

Examples of the cAMP activation substance that can be used include forskolin, indomethacin, NKH477 (colforsin daropate), a cell-derived toxin protein (pertussis toxin, cholera toxin), PACAP-27, PACAP-38, SKF83822. The concentration of the cAMP activation substance (e.g., forskolin) to be added is, for example, 1 µM to 200 µM, and preferably, 5 µM to 100 µM. Note that, if compounds different from the compound shown as an example, i.e., forskolin, are used, the concentrations of the compounds to be added can be determined by those skilled in the art in consideration of difference in property (particularly, difference in activity) between the compounds to be used and the compound (forskolin) mentioned as an example and in accordance with the above ranges of concentrations. Whether the concentration range thus determined is appropriate or not can be checked by a preliminary experiment according to Examples described later.

The air-liquid interface culture is carried out, for example, for 3 to 21 days, preferably, 4 to 18 days, and further preferably 5 to 14 days. Note that, the air-liquid interface culture is typically carried out in an aerobic condition; however, an anaerobic condition may be employed.

The period (culture period) of step (6) is, for example, 12 to 36 days. In the middle of step (6), passage culture may be carried out. For example, cells that become confluent or sub-confluent are partly taken, transferred to another culture vessel and subsequently cultured. In collecting cells, e.g., a cell dissociation solution may be used. As the cell dissociation solution, proteolytic enzymes such as trypsin-EDTA, collagenase IV and metalloprotease may be used alone or appropriately in combination. It is preferable to use a cell dissociation solution low in cytotoxicity. As the cell dissociation solution as mentioned above, for example, a commercially available product such as Dispase (EIDIA Co., Ltd.), TrypLE (Invitrogen) or Accutase (MILLIPORE) can be used. It is desirable that the cells collected are processed by e.g., a cell strainer so as to obtain a dispersion (discrete) state and then subjected to passage culture. In step (6), if necessary, medium exchange is carried out, for example, at a frequency once per 24 hours to 3 days. For collecting cells at the time of passage culture and medium exchange, it is desirable that the cells are previously treated with a ROCK (Rho-associated coiled-coil forming kinase/Rho binding kinase) inhibitor such as Y-27632, in advance, in order to suppress cell death.

The other culture conditions (e.g., culture temperature) should be the conditions routinely employed in animal cell cultures. More specifically, culture may be carried out, for example, at 37° C., in an environment of 5% $CO_2$. The base medium is not particularly limited, a base medium suitable for culturing epithelial cells (for example, a mixed medium of D-MEM and Ham F12, D-MEM) is preferably used. Examples of the components that can be added in a culture medium include bovine serum albumin (BSA), an antibiotic substance, 2-mercapto ethanol, PVA, a non-essential amino acid (NEAA), insulin, transferrin and selenium.

As described later (4. Use of intestinal tract cell layer), the intestinal tract cell layer is, similarly to an intestinal organoid, useful for evaluation of pharmacokinetics (e.g., absorption, metabolism) and toxicity in the intestinal tract (particularly small intestine) or preparation of, e.g., an inflammatory bowel disease model and a fibrosis model. Due to a two dimensional structure, the intestinal tract cell layer makes it possible to perform high(er) throughput analysis. Further, use in construction of a co-culture system with enterobacteria and assay using the co-culture system can be expected.

3. Use of Intestinal Organoid

A second aspect of the present invention relates to use of the intestinal organoid obtained by the preparation method of the invention. As a first use, various assays are provided. The intestinal organoid of the present invention can be used for an intestinal tract model, particularly a small intestine model (system) and is useful for evaluation of pharmacokinetics (e.g., absorption, metabolism) in the intestinal tract, particularly in the small intestine, and toxicity evaluation. In other words, the intestinal organoid of the present invention can be used for evaluation of in-vivo kinetics of a compound and toxicity evaluation.

More specifically, test substance's metabolism, absorbency, membrane permeability, drug interaction, induction of a drug-metabolizing enzyme, or induction of a drug transporter, or toxicity can be tested by using the intestinal organoid of the present invention. In other words, the present invention provides, as one of the uses of the intestinal organoid, a method for evaluating, e.g., test substance's metabolism, absorbency, membrane permeability, drug interaction, induction of a drug-metabolizing enzyme, or induction of a drug transporter, or toxicity. In the method, the following steps are carried out: (I) contacting the test substance with the intestinal organoid obtained by the preparation method of the present invention; and (II) determining/evaluating test substance's metabolism, absorbency, membrane permeability, drug interaction, induction of a drug-metabolizing enzyme, or induction of a drug transporter, or toxicity.

In step (I), the "contact" is typically carried out by adding a test substance to a culture medium. The timing of addition of a test substance is not particularly limited. Thus, culture may be initiated in a culture medium containing no test substance, and thereafter, a test substance may be added at a certain time point, or culture may be initiated in a culture medium already containing a test substance.

As a test substance, any one of organic compounds or inorganic compounds different in molecular size can be used. Examples of the organic compounds include a nucleic acid, a peptide, a protein, a lipid (a simple lipid, a complex lipid (e.g., phosphoglyceride, sphingolipid, glycosyl glyceride, cerebroside)), prostaglandin, isoprenoid, terpene, steroid, polyphenol, catechin and vitamin (e.g., B1, B2, B3, B5, B6, B7, B9, B12, C, A, D, E). Any one of the existing components or candidate components of pharmaceuticals, nutritional foods, food additives, agricultural chemicals and cosmetics is a preferable test substance. A plant extract, a cell extract and a culture supernatant may be used as a test substance. At least two test substances may be simultaneously added to check, e.g., interaction and synergetic effect between the test substances. A test substance may be a naturally occurring substance or a synthesized substance. In the latter case, an efficient assay system can be constructed by use of, for example, a combinatorial synthesis technique.

The period during which a test substance is allowed to be in contact with an intestinal organoid can be arbitrarily determined. The contact period is, for example, 10 minutes to 3 days, and preferably, one hour to one day. The contact may be discretely carried out in a plurality of times.

After step (I), test substance's metabolism, absorbency, membrane permeability, drug interaction, induction of a drug-metabolizing enzyme, or induction of a drug transporter, or toxicity are determined or evaluated (step (II)). Immediately after step (I), that is, after contact with a test substance, metabolism and others may be determined/evaluated without a substantial interval. Alternatively, metabolism and others may be determined/evaluated at a predetermined interval (for example, 10 minutes to 5 hours). Metabolism can be determined by detection of, for example, a metabolite. In this case, usually, the culture solution of step (I) is used as a sample and a presumable metabolite is qualitatively or quantitatively measured. The measuring method may be appropriately selected depending on the metabolite. For example, mass spectrometry, liquid chromatography, immunological analysis (for example, fluorescence immunoassay (FIA) and enzyme immunoassay (EIA)) can be employed.

Typically, if a metabolite of a test substance is detected, it is determined or evaluated that the "test substance was metabolized". The amount of a test substance metabolized can be evaluated based on the amount of its metabolite. Based on the detection results of a metabolite and the amount of a test substance used (typically, the amount of the test substance added to a culture medium), the metabolic efficiency of the test substance may be calculated.

Whether a test substance was metabolized or not can be determined based on expression of a drug-metabolizing enzyme (e.g., cytochrome P450 (particularly, CYP3A4 in a human, CYP3A8 in a cynomolgus monkey), uridine 2 phosphate-glucuronosyltransferase (particularly, UGT1A8, UGT1A10) and/or sulfotransferase (particularly, SULT1A3)) in an intestinal organoid, as an index. Expression of a drug-metabolizing enzyme can be evaluated based on mRNA level or protein level. For example, if the mRNA level of a drug-metabolizing enzyme increases, it can be determined that "expression level at a gene level increased". If the activity of a drug-metabolizing enzyme increases, it can be determined that a "test substance was metabolized". Similarly to the case where determination is made based on a metabolite as an index, quantitative determination/evaluation may be made based on the expression level of a drug-metabolizing enzyme.

Absorption of a test substance is evaluated by measuring, for example, the residual amount of a test substance in a culture solution. Usually, the culture solution of step (I) is used as a sample to quantify a test substance. An appropriate measuring method may be selected depending on the test substance. For example, mass spectrometry, liquid chromatography, immunological analysis (for example, fluorescence immunoassay (FIA) and enzyme immunoassay (EIA)) can be employed. Typically, if the content of a test substance in a culture solution decreased, it is determined that a "test substance was absorbed". The absorption amount or absorption efficiency of a test substance can be determined/evaluated by the degree of a decrease. Note that, absorption can be evaluated by measuring the amount of a test substance taken in a cell.

Note that, determination/evaluation of metabolism and absorption may be simultaneously or parallelly carried out.

As shown in Examples (described later), the intestinal organoid obtained by the preparation method of the invention can reproduce a pathological condition of an intestinal disease. Then, as a second use of the intestinal organoid of the present invention, an intestinal disease model, a method for preparing the model, and an assay using the model, are provided.

If the intestinal organoid of the present invention is used, it is possible to prepare an intestinal disease model, for example, a pathological model of inflammatory bowel disease, a pathology model (fibrosis model) reproducing fibrosis of a tissue developed by inflammation of inflammatory bowel disease, and a cancer pathological model. A pathological model of inflammatory bowel disease may be prepared by culturing the intestinal organoid of the present invention in the presence of, e.g., at least one of inflammatory cytokines such as TNF-α, IFN-γ, IL-1, IL-6, IL-17a to develop inflammation or disorder. A pathological model may be produced by co-culturing the intestinal organoid and immune cells. A fibrosis model may be produced by inducing fibrosis by use of, e.g., TGF-β or TNF-α and TNF-β in combination.

An intestinal disease model is useful for drug screening. More specifically, if an intestinal disease model is used, an in-vitro evaluation system for screening a substance effective for an intestinal disease (active ingredient or lead compound of a pharmaceutical), can be constructed. In the evaluation system, the action and effect of a test substance on a pathological condition reproduced by an intestinal disease model are examined and the effectiveness of the test substance is evaluated.

As a third use of the intestinal organoid obtained by the preparation method of the invention, a transplant material containing an intestinal organoid is provided. The transplant material of the present invention is applicable to treatments of various intestinal diseases (for example, refractory inflammatory bowel disease). Particularly, the transplant material is presumably used as a regeneration/reconstruction material for damaged intestinal tract tissue (including dysfunctional intestinal tract tissue). In other words, contribution of the transplant material to regenerative medicine can be expected. The transplant material of the present invention can be directly used as a transplant material or used after disposing Matrigel and collagen gel embedding. In addition, the transplant material is conceivably used as various intestinal disease pathological models for screening therapeutic drug candidate compounds and for elucidation of pathological mechanisms. Substances such as dimethyl sulfoxide (DMSO) and serum albumin for protecting cells, antibiotic substances for inhibiting contamination with bacteria and various components (e.g., vitamins, cytokine, growth factors, steroid) for activating, proliferating or inducing differentiation of cells may be contained in the transplant material of the present invention. Further, pharmaceutically acceptable additives (for example, carrier, excipient, disintegrant, buffer, emulsifier, suspension, painless agent, stabilizer, preservative, preservative, saline) may be contained in the transplant material of the present invention.

The transplant material of the present invention can be used for constructing an in-vivo experimental system. For example, a humanized animal (human intestinal tract model) can be prepared by transplanting a transplant material containing an intestinal organoid prepared by using a human pluripotent stem cell to an experimental animal such as a mouse, a rat, a guinea pig, a hamster, a pig, a cynomolgus monkey, a rhesus monkey and a chimpanzee. Such a humanized animal is particularly useful for, e.g., pharmacokinetic experiments and toxicity tests and contribution of the humanized animal to investigation of, e.g., a first pass effect of an oral drug and drug-induced enteritis, is expected.

An intestinal organoid prepared by using an iPS cell derived from a patient with an intestinal disease can be used as an intestinal tract pathology model not only in a drug evaluation system but also in experiments for elucidating mechanisms of onset, formation of pathological conditions and/or progress of intestinal diseases.

4. Use of Intestinal Tract Cell Layer

Another aspect of the present invention relates to use of an intestinal tract cell layer. Similarly to the intestinal organoid, the intestinal tract cell layer is useful for evaluation of drug kinetics (e.g., absorption, metabolism) in the intestinal tract (particularly, in the small intestine) and toxicity. Since an assay using an intestinal tract cell layer is a two-dimensional evaluation system, a high(er) throughput assay can be made.

More specifically, the intestinal tract cell layer of the present invention can be used for examining, e.g., test substance's metabolism, absorbency, membrane permeability, drug interaction, induction of a drug-metabolizing enzyme, or induction of a drug transporter, or toxicity. That is, the present invention provides, as the use of the intestinal tract cell layer, a method (first embodiment) for examining, e.g., test substance's metabolism, absorbency, membrane permeability, drug interaction, induction of a drug-metabolizing enzyme, or induction of a drug transporter, or toxicity. In the method, the following steps are carried out: (i) preparing the intestinal tract cell layer obtained by the intestinal tract cell layer preparation method of the present invention; (ii) contacting a test substance with the intestinal tract cell layer; and (iii) quantifying the test substance passed through the intestinal tract cell layer and determining/evaluating the test substance's metabolism, absorbency, membrane permeability, drug interaction, induction of a drug-metabolizing enzyme, or induction of a drug transporter, or toxicity.

In step (i), typically, an intestinal tract cell layer is formed/prepared by culturing cells collected from an intestinal organoid on a semi-permeable membrane (porous membrane).

Since step (ii) herein is the same as step (I) in the evaluation method using an intestinal organoid, further explanation thereof is omitted for brevity's sake.

In step (iii), a test substance passed through a cell layer is quantitatively determined. If, e.g., a culture vessel having an insert such as Transwell (registered trademark) is used, a test substance passed through the insert, more specifically, a test substance, which passes through the cell layer and migrates to the upper or lower portion of the vessel, is quantified by a measurement means such as mass spectrometry, liquid chromatography, immunological method (for example, fluorescence immunoassay (FIA), enzyme immunoassay (EIA), which varies depending on the test substance. Based on the quantitation results (the amount of the test substance passed through the cell layer) and the supply amount of the test substance (typically the amount of the test substance added to a culture medium), the test substance's metabolism, absorbency, membrane permeability, drug interaction, induction of a drug-metabolizing enzyme, or induction of a drug transporter, or toxicity can be determined/evaluated. Note that, the evaluation method of the embodiment is particularly useful for evaluating test substance's metabolism, absorbency or membrane permeability.

According to another embodiment (second embodiment) of the invention, there is provided an evaluation method including the steps of: (I) contacting the test substance with the intestinal tract cell layer obtained by the intestinal tract cell layer preparation method of the present invention; and (II) determining/evaluating test substance's metabolism, absorbency, induction of a drug-metabolizing enzyme, or induction of a drug transporter, or toxicity.

Step (I) and step (II) herein are the same as step (I) and step (II) in the evaluation method using an intestinal organoid, respectively, and thus, further explanation thereof is omitted for brevity's sake.

As a second use of the intestinal tract cell layer of the present invention, e.g., an intestinal disease model, a method for preparing the model, and an assay using the model are provided. Similarly to the intestinal organoid, if the intestinal tract cell layer of the present invention is used, it is possible to prepare an intestinal disease model, for example, a pathological model of inflammatory bowel disease, a pathology model (fibrosis model) reproducing fibrosis of a tissue developed by inflammation of inflammatory bowel disease, and a cancer pathological model. A method for preparing individual pathological models may follow the case using an intestinal organoid. Similarly to the case of using an intestinal organoid, an intestinal disease model prepared by use of the intestinal tract cell layer of the present invention is useful for drug screening.

EXAMPLES

<Preparation of iPS Cell-Derived Intestinal Organoid>

In order to find a new method for producing a functional intestinal organoid, the following studies were carried out. Note that, attention was paid to the fact that a two-dimensional culture system (plane culture) is useful for high throughput assay. An intestinal organoid was prepared and cells were collected from the intestinal organoid, and then, whether a pathological model and a two dimensional evaluation model available for drug screening can be produced or not was investigated.

1. Method (1) Cell

Human iPS cells (iPS-51: Windy), which were prepared by introducing, to human fetal lung fibroblast MRC-5, octamer binding protein 3/4 (OCT3/4), sex determining region Y-box2 (SOX2), kruppel-like factor 4 (KLF4) and v-myc myelocytomatosis viral oncogene homolog (avian) (c-MYC) by use of a Pantropic retroviral vector, and then, cloning a human ES cell-like colony, were provided by Dr. Akihiro Umezawa, (the National Center for Children's Health and Development). As the feeder cells, mouse fetal fibroblasts (MEF) were used.

(2) Culture Medium

For culturing MEF, Dulbecco modified Eagle's medium (DMEM) containing 10% fetal bovine serum (FBS), 2 mmol/L L-glutamine (L-Glu), a 1% non-essential amino acid (NEAA), 100 units/mL penicillin G, and 100 µg/mL streptomycin, was used. A 0.05% trypsin-ethylenediamine tetraacetic acid (EDTA) solution was used as an MEF cell dissociation solution, CELLBANKER 1 was used as a MEF preservative solution. For maintenance culture of human iPS cells, DMEM Ham's F-12 (DMEM/F12) containing a 20% knockout serum replacement (KSR), a 0.8% NEAA, 2 mmol/LL-Glu, 0.1 mmol/L 2-mercapto ethanol (2-MeE), and 5 ng/mL fibroblast growth factor (FGF) 2, was used. Dulbecco phosphate buffered saline (PBS) containing 1 mg/mL collagenase IV, 0.25% trypsin, 20% KSR, and 1 mmol/L calcium chloride, was used as a dissociation solution for human iPS cells. A cryopreservation solution for primate ES/iPS cells was used as a preservation solution for human iPS cells.

(3) Culture of Human iPS Cells

Human iPS cells were seeded on MEF ($6 \times 10^5$ cells/100 mm dish) treated with mitomycin C and cultured in the condition of 5% $CO_2$/95% air in a $CO_2$ incubator at 37° C. After culture for 3 to 5 days, passage culture of human iPS cells was carried out at a split ratio of 1:2 to 1:3. The culture medium of the human iPS cells was exchanged 48 hours after thawed and thereafter every day.

(4) Differentiation of Human iPS Cells into Intestinal Organoid

Differentiation of human iPS cells into intestinal organoid was carried out as follows: human iPS cells were seeded in a culture dish coated with Matrigel (growth factor was removed) diluted 30 fold with a human iPS cell medium in passage culture, and cultured in StemSure (registered trademark) hPSC culture medium containing 35 ng/mL FGF2. At the state where the ratio of undifferentiated colonies reached about 80%, differentiation of the human iPS cells into intestinal organoid was initiated. Culture was carried out in the Roswell Park Memorial Institute (RPMI) culture medium containing 100 ng/mL activin A, 100 units/mL penicillin G, 100 μg/mL streptomycin, and 2 mmol/L L-Glu for one day; in RPMI culture medium containing 0.2% FBS, 100 ng/mL activin A, 100 units/mL penicillin G, 100 μg/mL streptomycin and 2 mmol/L L-Glu for one day; and RPMI culture medium containing 2% FBS, 100 ng/mL activin A, 100 units/mL penicillin G, 100 μg/mL streptomycin and 2 mmol/L L-Glu for one day. In this manner, differentiation into the endoderm was carried out. Thereafter, culture was carried out in RPMI+glutamax medium containing 2% FBS, 500 ng/mL FGF4, 3 μmol/L CHIR99021, 100 units/mL penicillin G and 100 μg/mL streptomycin for 4 days. In this manner, differentiation into intestinal stem cells was carried out. A treatment with FGF4 and CHIR99021 was carried out, and thereafter, Y-27632 (Rho binding kinase inhibitor) was added so as to obtain a concentration of 10 μmol/L; and cells were treated in the condition of 5% $CO_2$/95% air in a $CO_2$ incubator at 37° C. for 60 minutes and removed by a 0.05% trypsin-EDTA solution, crushed by a cell strainer with 40 μm nylon mesh and seeded on a 100-mm dish coated with iMatrix511silk diluted with PBS (−) up to a concentration of 0.16 μg/mL so as to obtain a cell density of $2.0 \times 10^6$ cells. The cells were cultured in Advanced-DMEM/F12 containing 1% glutamax, 10% KSR, 100 units/mL penicillin G, 100 μg/mL streptomycin, 100 ng/mL epidermal growth factor (EGF), 30 ng/mL FGF2, 0.5 μmol/L A-83-01, 3 μmol/L CHIR99021, and 10 μmol/L Y-27632. Thereafter, the cells were removed with Accutase every two days at most twice and seeded on a 100-mm dish coated with iMatrix511silk diluted with PBS (−) to a concentration of 0.16 μg/mL so as to obtain a density of $2.0 \times 10^6$ cells. The cells were cultured in Advanced-DMEM/F12 containing 1% glutamax, 10% KSR, 100 units/mL penicillin G, 100 μg/mL streptomycin, 100 ng/mL epidermal growth factor (EGF), 30 ng/mL FGF2, 0.5 μmol/L A-83-01, 3 μmol/L CHIR99021, and 10 μmol/L Y-27632. Two or three days later, the cells were removed in the same manner as above, $3.0 \times 10^6$ cells were seeded on 100-mm EZSPHERE (registered trademark). Thereafter, the cells were cultured with Advanced-DMEM/F12 containing 1% glutamax, 2% B27 supplement, 1% N2 supplement, 100 units/mL penicillin G, 100 μg/mL streptomycin, 100 ng/mL EGF, 100 ng/mL Noggin, 200 ng/mL R-spondin-1, and 10 μmol/L Y-27632 for two days and subjected to suspension culture on an ultra-low adhesive 100-mm dish with Advanced-DMEM/F12 containing 1% glutamax, 2% B27 supplement, 1% N2 supplement, 100 units/mL penicillin G, 100 μg/mL streptomycin, 100 ng/mL EGF, 100 ng/mL Noggin, 200 ng/mL R-spondin-1 and Matrigel (3%) (growth factor was removed), for 21 days. In this manner, the cells were differentiated into an intestinal organoid. In the following experiment, the cells, which were seeded on EZSPHERE (registered trademark) on Day 7 after differentiation induction to form an intestinal organoid, was used as a control group. The culture method (differentiation protocol) mentioned above is schematically shown in FIG. 9.

To prepare an inflammatory bowel disease model and a fibrosis model, 30 ng/mL TNF-α and 30 ng/mL TNF-α+2 ng/mL TGF-β were added for 96 hours and 48 hours from Day 34 after completion of differentiation induction, respectively. To suppress these reactions, 100 ng/mL infliximab (anti-TNF-α antibody) for the inflammatory bowel disease model and 20 μM SB431542 or 20 μM Repsox serving as a TGF-β inhibitor, for fibrosis model were added, respectively, for the same length of time as above. Note that, to enhance the function of an intestinal organoid, PD98059, 5-aza-2'-deoxycytidine, A-83-01 and N-[(3,5-difluorophenyl) acetyl]-L-alanyl-2-phenyl-1,1-dimethylethylester-glycine (DAPT) were added from Day 19 after initiation of differentiation induction to the completion of differentiation. The addition effects in these cases were checked.

(5) Passage and Plane Culture of Intestinal Organoid on Transwell (Registered Trademark) and Multi-Well Plate Y27632 was added so as to be a concentration of 10 μmol/L to an intestinal organoid prepared in the absence of a low-molecular compound (PD98059, 5-aza-2'-deoxycytidine, A-83-01, DAPT) or in the presence of a low-molecular compound (PD98059, 5-aza-2'-deoxycytidine, A-83-01, DAPT), or to a highly functional intestinal organoid (obtained by culturing 19 to 34 days) prepared in accordance with a new culture method. The cells were treated in the condition of 5% $CO_2$/95% air in a $CO_2$ incubator at 37° C. for 24 hours, removed with a cell dissociation solution (0.05% trypsin-EDTA) and crushed by a cell strainer with 40 μm nylon mesh. On Transwell (registered trademark) insert or multi-well plate coated with iMatrix511silk, the cells were seeded at a density of $3.0 \times 10^5$ cells/cm². After seeding, a treatment with Y-27632 (10 μM) was carried out for 24 hours. Thereafter, culture was carried out in culture medium 7 (see, FIG. 9) for 6 to 14 days. At the time of culture, various compounds were added, the optimal condition was found out.

(6) Extraction of Total Ribonucleic Acid (RNA)

After completion of differentiation induction of human iPS cells, total RNA was extracted in accordance with the manual attached to "Agencourt RNAdvence Tissue".

(7) Reverse Transcription Reaction

Complementary DNA (cDNA) was synthesized by ReverTra Ace qPCR RT MasterMix in accordance with the manual attached thereto.

(8) Real-Time RT-PCR Method

Real-Time RT-PCR was carried out by use of KAPA SYBR Fast qPCR Kit with cDNA used as a template in accordance with the manual attached thereto. The results were corrected with hypoxanthine phosphoribosyl transferase (HPRT) used as an endogenous control.

(9) Staining with Hematoxylin-Eosin (HE) and Staining with Alcian Blue

After completion of differentiation induction, an intestinal organoid was fixed with 4% paraformaldehyde, embedded with an OCT compound and frozen. Frozen sections (10 μm in thickness) of the intestinal organoid were prepared, attached to slide glasses and stained with HE and Alcian Blue. In the case of HE staining, a Mayer's hematoxylin/eosin alcohol solution was used. In the case of Alcian Blue staining, Alcian Blue (pH2.5) was used. Staining for nuclei, nuclear fast red was used.

(10) Immunofluorescent Staining

After completion of differentiation induction, an intestinal organoid was fixed with 4% paraformaldehyde, embedded with an OCT compound and frozen. Frozen sections (10 µm in thickness) of the intestinal organoid were prepared and attached to slide glasses, and then, activation of an antigen was carried out. Blocking was carried out with a 5% FBS solution for 30 minutes, a primary antibody was allowed to react at 4° C., overnight. Thereafter, the slide glasses were washed and a secondary antibody was allowed to react at room temperature for one hour. As nuclear staining, 4',6-diamino-2-phenylindole (DAPI) was used. Encapsulation work was carried out and fluorescence was observed by use of a confocal laser scanning microscope, ZeissLSM510.

Characteristics of marker genes used in this study are shown below.

α-SMA (alpha-smooth muscle actin; smooth muscle marker)

ABCB1/P-gp (ATP-binding cassette transporter B1/multi drug resistant protein 1, P glycoprotein; efflux transporter)

ABCG2/BCRP (ATP-binding cassette transporter G2/breast cancer resistant protein; efflux transporter)

APOB (apolipoprotein B; principally synthesized in the small intestine and having an essential role in absorbing a lipid from the small intestine)

APOC3 (apolipoprotein C3; principally synthesized in the small intestine and having an essential role in absorbing a lipid from the small intestine)

BRACHYURY (encoding a transcriptional regulator having a novel DNA binding domain called as T box, and important for formation of the posterior mesoderm)

Caspase-3 (Cas) (protein involved in execution of apoptosis) CD34 (cell-surface glycoprotein; marker for cells hematopoietic and endothelial progenitor cells derived from the mesoderm system)

CDX2 (Caudal-type homeobox 2; transcription factor involved in proliferation/differentiation of intestinal epithelial cells)

Chromogranin A (CHGA) (specific protein present in secretory granules; intestinal tract endocrine cell marker)

Collagen type 1 (colla-1) (main component in the extracellular matrix; fibrous collagen) CYP3A4 (main drug-metabolizing enzyme in the intestinal tract) E-cadherin (E-cad) (epithelial cadherin; belong to a group of glycoproteins present in a cell surface; a molecule responsible for cell adhesion)

Fibronectin (a huge glycoprotein and serving as a cell adhesion molecule)

FLK1 (KDR active kinase; early mesoderm marker)

HOXA13 (gene HOX determining the front and rear axis and segmentation of a tissue in the early state of animal embryogenesis; colon specific marker)

ISX (intestinal tract-specific homeobox; involved in intestinal tract epithelial metaplasia and cell proliferation)

LGR5 (leucine rich repeat-containing G protein-conjugated receptor; marker for intestinal stem cells)

Lysozyme (Lyso) (hydrolysis enzyme for polysaccharides constituting the cell wall of eubacteria; intestinal tract Paneth cell marker)

MUC2 (mucin 2 glycoprotein; goblet cell marker)

Occludin (main protein involved in formation of tight junction)

SATB2 (protein specifically expressed in the colon and rectal epithelial cells)

SLC15A1/PEPT1 (SLC (solute carrier) family member 15A1/peptide transporter 1; expressed on a top membrane side of the small intestine)

Villin (main component constituting microvillus; absorptive epithelial cell marker)

Vimentin (Vim) (intermediate filaments specific to mesenchymal cells)

ZO-1 (main protein involved in formation of tight junction)

2. Results/Consideration (1) Morphology of Intestinal Organoid Prepared by New Intestinal Organoid Preparation Method Morphology of an intestinal organoid on Day 34 after initiation of differentiation induction was observed. As a result, a spherical shape was observed in a control group (FIG. 1A). In the intestinal organoid passaged, budding form having crypto-villus structures was observed (FIGS. 1B, C). Although CHIR99021 was used as a GSK3 inhibitor in passage culture, other 6 types of GSK3 inhibitors were used for preparation of an intestinal organoid. It was confirmed that the intestinal organoids treated with the GSK3 inhibitors all have budding-form crypto-villus structures (FIGS. 1D to I).

(2) Gene Expression of Intestinal Organoid Prepared by New Intestinal Organoid Preparation Method The expressions of genes in an intestinal organoid on Day 34 after initiation of differentiation induction were compared to those of a control group and the adult small intestine. As a result, the expression of an absorptive epithelial cell marker, villin; a goblet cell marker, MUC2; and intestinal-specific transcription factors, CDX2 and ISX, were extremely high due to procedure for passage culture. In contrast, the expressions of a Paneth cell marker, lysozyme; and an intestinal endocrine cell marker, chromogranin A, were equivalent to those in the control group (FIG. 2).

(3) Morphological Analysis of Intestinal Organoid Prepared by New Intestinal Organoid Preparation Method From the results of staining with HE and Alcian Blue, it was found that an intestinal organoid is constituted of a cell population containing secretory cells (FIGS. 3A, B). It was confirmed by immunofluorescent staining that markers for various cells (absorptive epithelial cell, intestinal stem cell, goblet cell, intestinal endocrine cell, Paneth cell, mesenchymal cell) constituting the intestinal tract express (FIG. 3C). Thus, it was suggested that the intestinal organoid is an intestinal tract tissue analog containing these cells.

(4) Characteristics of Intestinal Organoid Prepared by New Intestinal Organoid Preparation Method In an intestinal organoid, the expressions of small intestine markers, APOB and APOC3, were extremely high; whereas the expressions of colon markers, HOXA13 and SATB2, were low (FIG. 4). The results suggested the possibility that the intestinal organoid has characteristics close to those of the small intestine.

(5) Gene Expression Analysis and Immunofluorescent Staining of Drug Transporter of an Intestinal Organoid Prepared by New Intestinal Organoid Preparation Method The expression level of a transporter, PEPT1 gene, was close to that of an adult small intestine; however, the gene expression level of P-gp was slightly low (FIG. 5A). From the results of immunofluorescent staining, it was found that tight-junction proteins, occludin and ZO-1, and drug transporters, PEPT1 and BCRP, are locally expressed along the lumen of an intestinal organoid (FIG. 5B). From the results, it was confirmed that drug transporters are expressed in the small intestine; and suggested that the lumen side of the intestinal organoid corresponds to the brush border membrane side. Based on morphological observation, it was suggested that the intestinal organoid has a villi-like structure.

(6) Differentiation Induction of the Mesoderm System is Suppressed by New Intestinal Organoid Preparation Method To check the states of individual cells immediately before seeded in EZSPHERE at the time of differentiation induction, mRNA expression was analyzed. As a result, the expression of an intestinal tract-specific transcription factor, CDX2, did not change without being affected by the procedure for passage culture and the effect of culture medium 5; however, the expression of mesoderm markers, BRACHYURY, CD34, and FLK1, decreased when the cells were cultured in culture medium 5, and further decreased by the procedure for passage culture (FIG. 6). The results suggested the possibility that differentiation of cells can be selectively induced into the intestinal tract by carrying out culture in culture medium 5 in combination with procedure for passage culture.

(7) Preparation of Inflammatory Bowel Disease Model Using Intestinal Organoid

Whether an inflammatory bowel disease model can be prepared by using an intestinal organoid prepared by a new differentiation induction method was investigated by adding a main cause, i.e., an inflammatory cytokine, TNF-α, from Day 34 after completion of differentiation induction up to 96 hours (FIG. 7A). The expressions of villin and MUC2 gene decreased by addition of TNF-α; however, the expression of TNF-α increased. The decrease/increase in expression was suppressed by addition of an anti-TNF-α antibody, infliximab (FIG. 7B). Subsequently, expressions of a tight junction protein and an apoptosis marker were confirmed by immunofluorescent staining. It was observed that a tight junction structure is destroyed by addition of TNF-α. The number of cells positive to Caspase-3 increased. These changes were not found in an infliximab addition group (FIG. 7C). In inflammatory bowel disease, it is reported that an inflammatory cytokine affects in-vivo intestinal epithelial cells to destroy tight junction, with the result that the number of mucus secretory cells, i.e., goblet cells, decreases. Thus, it was suggested that an inflammatory bowel disease pathological model can be easily prepared by adding TNF-α in an in-vitro evaluation system and used in drug screening.

(8) Preparation of Fibrosis Model Using Intestinal Organoid

In order to reproduce fibrosis of a tissue in-vitro, which is developed by chronic inflammation in inflammatory bowel disease, TNF-α and TGF-β, each are reported as a main cause, were added for 48 hours from Day 34 after completion of differentiation induction (FIG. 8A). As a result of addition of TNF-α and TGF-β, the mRNA expressions of fibrosis markers, a-SMA, vimentin, fibronectin and collagen type 1, increased. In contrast, expression of an epithelial cell marker, E-cadherin, decreased. The decrease/increase in expression of each of these fibrosis markers was suppressed by addition of a TGF-β inhibitor, SB431542 or Repsox (FIG. 8B). The results suggested the possibility that a fibrosis model can be prepared by adding TNF-α and TGF-β. In addition, the result that the level of a fibrosis marker increases and the level of an epithelial cell marker decreased suggested the possibility that epithelial-mesenchymal transition involved in fibrosis can be reproduced.

(9) Effect of Addition of Low-Molecular Compound on Intestinal Organoid

In order to prepare a highly functional intestinal organoid having a function close to that in a living body, for use in a drug screening system having high(er) reliability and accuracy, culture was carried out by adding a low-molecular compound conceivably effective for differentiation. As a result, the mRNA expression levels of CYP3A4 and MUC2 increased (FIG. 10).

(10) Preparation of New Plane Culture System Applicable to High-Throughput Analysis To prepare a plane culture system (more) suitable for preparing a pathological model and a drug screening system, cells were collected from an intestinal organoid and seeded in the insert of Transwell (registered trademark) to form a cell layer, and characteristics of the cell layer were checked. In a group in which a low-molecular compound (PD98059, 5-aza-T-deoxycytidine, A-83-01, DAPT) was not added at the time of intestinal organoid preparation, the transepithelial electrical resistance (TEER) value increased or was kept stable in some of culture patterns (FIG. 11B). The membrane resistance values of low-molecular compound addition groups did not increase in all culture patterns. In four groups in which a membrane resistance value more or less increased, mRNA expression level was measured. In the group in which only forskolin was added or forskolin and DAPT or CHIR99021 were added in combination, an intestinal tract marker, CDX2, and an intestinal stem cell marker, LGR5, were highly expressed, and CYP3A4 and MUC2 were also expressed (FIG. 11A). From the above, it can be said that the plane culture system prepared is useful for drug screening; and suggested that a further increase in function can be expected by addition of forskolin, DAPT, and/or CHIR99021. Note that, it is said that the condition where a membrane resistance value remarkably increased, more specifically, where forskolin and DAPT were used in combination, is particularly effective.

(11) Induction Test of CYP3A4 Using New Plane Culture System

In the new plane culture system prepared, a test for inducing a major metabolic enzyme in the intestinal tract, CYP3A4, was carried out. Drug response was evaluated by comparing mRNA expression levels by qPCR. The mRNA expression level of CYP3A4 increased about 900 fold by treating the culture system with rifampicin and about 1700 fold with an activated vitamin $D_3$ (FIG. 12). The results suggest that the metabolic enzyme is induced in the new plane culture system prepared via PXR and VDR.

(12) Preparation of Plane Culture System Having Villi-Like Structure

Twenty four hours or more after initiation of plane culture, culture medium was added in only the lower portion (well) of the insert (of a culture vessel) and air-liquid interface culture was carried out. Differentiation induction was promoted by activating cAMP signal. As the culture medium, culture medium 7 containing a low-molecular compound was used. As the factors activating cAMP signals, forskolin, 8-bromo-cAMP (8-Br-cAMP) and 3-isobutyl-1-methylxanthine (IBMX) were used. A plane culture system having a villi-like structure was successfully prepared by carrying out air-liquid interface culture and activating cAMP signal (FIGS. 13B-F). In the case where a TGF-β inhibitor, A83-01, was not added, a villi-like structure was not formed (FIG. 13A). From these results, it was suggested that cAMP signal and TGF-β signal are strongly involved in construction of a tissue-like structure in the plane culture system.

3. Conclusion

As is apparent from the results, a budding intestinal organoid having characteristics close to those of the small intestine of a living body was successfully prepared from human iPS cells in this study. In the intestinal organoid prepared, the gene expressions of intestinal tract markers and drug transporters are both close to those of the adult small intestine. It was suggested that the intestinal organoid prepared has crypto-villus like structures. Also, a large amount of uniform intestinal organoids was successfully obtained by suspension culture using EZSPHERE. Furthermore, an inflammatory bowel disease model and a fibrosis model were successfully prepared by adding cytokines serving as main causes of respective diseases, suggesting the possibility that these models can be useful as screening systems for drugs against these respective pathological conditions. In addition, it was suggested that a model useful for a high throughput assay can be prepared by transferring the prepared intestinal organoid to a plane culture. Furthermore, a high functional evaluation system having a villi structure was successfully constructed by air-liquid interface culture. The evaluation system has not only convenience for social use but also a function as an evaluation system, and is considered extremely useful for use in, e.g., drug discovery research, food-related research, research in co-culture with intestinal tract microbiota and infection research in intestinal tract cells.

<Study on Suspension Culture Condition>

In order to promote differentiation, enhance a function, and construct a culture system containing no components derived from an animal of another species, suspension culture using a culture medium containing a polysaccharide polymer in place of Matrigel was carried out for preparing an intestinal organoid.

1. Method (1) Cell

Human iPS cell (iPS-51: Windy), which is a cell obtained by introducing, to a human fetal lung fibroblast MRC-5, an octamer binding protein 3/4 (OCT3/4), sex determining region Y-box2 (SOX2), kruppel-like factor 4 (KLF4), and v-myc myelocytomatosis viral oncogene homolog (avian) (c-MYC) by use of a pantropic retroviral vector, and then, cloning a human ES cell-like colony; and which was provided by Dr. Akihiro Umezawa of the National Center for Children's Health and Development. As a feeder cell, a mouse fetal fibroblast (MEF) was used.

(2) Culture Medium

MEF was cultured in Dulbecco modified eagle's medium (DMEM) containing 10% fetal bovine serum (FBS), 2 mmol/L L-glutamine (L-Glu), a 1% non-essential amino acid (NEAA), 100 units/mL penicillin G and 100 µg/mL streptomycin. As a cell dissociation solution for MEF, 0.05% trypsin-ethylenediamine tetraacetic acid (EDTA) solution was used. As a preservative solution for MEF, CELL-BANKER 1 was used. As maintenance culture for a human iPS cell, DMEM Ham's F-12 (DMEM/F12) containing 20% knockout serum replacement (KSR), 0.8% NEAA, 2 mmol/L L-Glu, 0.1 mmol/L 2-mercapto ethanol (2-MeE), and 5 ng/mL fibroblast growth factor (FGF) 2, was used. As a dissociation solution for a human iPS cell, Dulbecco phosphate buffered saline (PBS) containing 1 mg/mL collagenase IV, 0.25% trypsin, 20% KSR, and 1 mmol/L calcium chloride, was used. As a preservative solution for a human iPS cell, a cryopreservation solution for primate's ES/iPS cells was used.

(3) Culture for Human iPS Cells

Human iPS cells were seeded on MEF ($6 \times 10^5$ cells/100 mm dish) treated with mitomycin C and cultured in a condition of 5% $CO_2$/95% air, in a $CO_2$ incubator at 37° C. After culture for 3 to 5 days, passage culture of human iPS cells was carried out at a split ratio of 1:2 to 1:3. The culture medium of the human iPS cells was exchanged with a fresh one, 48 hours after thawed, and thereafter, exchange was made every day.

(4) Differentiation of Human iPS Cells into Intestinal Organoid

Human iPS cell was differentiated into an intestinal organoid as follows: human iPS cells were seeded in a culture dish coated with Matrigel (growth factor was removed) diluted 30 fold with a human iPS cell medium at the time of passage culture, and cultured in StemSure (registered trademark) hPSC medium containing 35 ng/mL FGF2. At the state where the ratio of undifferentiated colonies reached about 80%, differentiation was initiated. Culture was carried out in the Roswell Park Memorial Institute (RPMI) medium containing 100 ng/mL activin A, 100 units/mL penicillin G, 100 µg/mL streptomycin, and 2 mmol/L L-Glu, for one day; in RPMI culture medium containing 0.2% FBS, 100 ng/mL activin A, 100 units/mL penicillin G, 100 µg/mL streptomycin and 2 mmol/L L-Glu, for one day; and in RPMI culture medium containing 2% FBS, 100 ng/mL activin A, 100 units/mL penicillin G, 100 µg/mL streptomycin and 2 mmol/L L-Glu, for one day. In this manner, differentiation into the endoderm was carried out. Thereafter, culture was carried out in RPMI+glutamax medium containing 2% FBS, 500 ng/mL FGF4, 3 µmol/L CHIR99021, 100 units/mL penicillin G and 100 µg/mL streptomycin, for 4 days. In this manner, differentiation into intestinal stem cells was carried out. A treatment with FGF4 and CHIR99021 was carried out, and thereafter, Y-27632 (Rho binding kinase inhibitor) was added so as to obtain a concentration of 10 µmol/L; and then, cells were treated in the condition of 5% $CO_2$/95% air in a $CO_2$ incubator at 37° C. for 60 minutes, removed by a 0.05% trypsin-EDTA solution, crushed by a cell strainer (40 µm nylon mesh) and seeded on a 100-mm EZSPHERE (registered trademark) so as to obtain a cell density of $3.0 \times 10^6$ cells. Thereafter, the cells were cultured in Advanced-DMEM/F12 containing 2 mmol/L L-Glu, 2% B27 supplement, 1% N2 supplement, 100 units/mL penicillin G, 100 µg/mL streptomycin, 100 ng/mL epidermal growth factor (EGF), 100 ng/mL Noggin, 200 ng/mL R-spondin-1 and 10 µmol/L, Y-27632, for 3 days and then subjected to suspension culture performed in Advanced-DMEM/F12 containing 2 mmol/L L-Glu, 2% B27 supplement, 1% N2 supplement, 100 units/mL penicillin G, 100 µg/mL streptomycin, 100 ng/mL EGF, 100 ng/mL Noggin, 200 ng/mL R-spondin-1, and Matrigel (3%) (growth factor was removed) or a polysaccharide polymer (deacylated gellan gum), for 24 days on an ultra-low adhesive 6-well plate. In this manner, the cells were differentiated into an intestinal organoid. From Day 19 to Day 34 after initiation of differentiation, a low-molecular compound previously found by the inventors, that is, PD98059 (20 mol/L), 5-aza-2'-deoxycytidine (5 µmol/L) or A-83-01 (0.5 µmol/L), and further, 5 µmol/L N-[(3,5-difluorophenyl) acetyl]-L-alanil-2-phenyl-1,1-dimethyleater-glycine (DAPT) were added. An inducer treatment of a drug-metabolizing enzyme was carried out by adding, to Advanced-DMEM/F12 containing 2 mmol/L L-Glu, 2% B27 supplement, 1% N2 supplement, 100 units/mL penicillin G, 100 µg/mL streptomycin, 100 ng/mL EGF, 100 ng/mL Noggin, 200 ng/mL R-spondin-1, Matrigel (3%) (growth factor was removed) or polysaccharide polymer (deacylated gellan gum) such that the concentration of 1α, 25-dihydroxy vitamin $D_3$ (VD3) became 1 μmol/L and cultured for 72 hours until collection. As the polysaccharide polymer, FP001 or FP003, provided by Nissan Chemical Industries, Ltd. was used in a concentration of 0.015% (w/v) per medium to investigate the effect thereof on differentiation of an intestinal organoid.

(5) Extraction pf Total Ribonucleic Acid (RNA)

After completion of differentiation induction of human iPS cells, total RNA was extracted in accordance with the manual attached to Agencourt RNAdvence Tissue.

(6) Reverse Transcription Reaction

Complementary DNA (cDNA) was synthesized by use of Rever Tra Ace qPCR RT Master Mix in accordance with the manual attached thereto.

(7) Real-Time RT-PCR Method

Real-Time RT-PCR was carried out by use of KAPA SYBR Fast qPCR Kit with cDNA used as a template in accordance with the manual attached thereto. The results were corrected by use of hypoxanthine phosphoribosyl transferase (HPRT) as an intrinsic control.

(8) Hematoxylin-Eosin (HE) Staining

After completion of differentiation induction, an intestinal organoid was fixed with 4% paraformaldehyde, embedded with an OCT compound and frozen. Frozen sections of the intestinal organoid of 10 μm in thickness were prepared, attached to slide glasses and stained by using Meyer hematoxylin and eosin alcohol.

(9) Immunofluorescent Staining

After completion of differentiation induction, an intestinal organoid was fixed with 4% paraformaldehyde, embedded with an OCT compound and frozen. Frozen sections of the intestinal organoid of 10 μm in thickness were prepared, attached to slide glasses, and then, an antigen was activated. Blocking was carried out with a 5% FBS solution for 30 minutes, a primary antibody was allowed to react at 4° C., overnight. Thereafter, the slide glasses were washed and a secondary antibody was allowed to react at room temperature for one hour. As nuclear staining, 4',6-diamizino-2-phenylindole (DAPI) was used. Encapsulation work was carried out and fluorescence was observed by use of a confocal laser scanning microscope, Zeiss LSM510.

(10) Transport Experiment of Rhodamine 123

After completion of differentiation induction, an intestinal organoid was incubated with HBSS containing rhodamine 123 at 37° C. HBSS used herein contained 137 mmol/L sodium chloride, 5.4 mmol/L potassium chloride, 0.81 mmol/L sulfuric acid magnesium, 0.44 mmol/L potassium dihydrogen phosphate, 0.34 mmol/L disodium hydrogen phosphate, 1.3 mmol/L calcium chloride, 4.2 mmol/L sodium hydrogen carbonate, 5.6 mmol/L D-glucose and 10 mmol/L HEPES; and having pH of 7.4. After completion of incubation, the cells were washed with ice-cold PBS to terminate uptake. Incubation was made with PBS warmed to 37° C. for 4 hours to allow rhodamine 123 to discharge outside the organoid. Thereafter, the fluorescence intensity of the supernatant was measured by use of Synergy HTX microplate reader. After completion of the transportation experiment, the amount of protein was measured. The fluorescence intensity value was corrected based on the amount of protein.

(11) Transport Experiment of Hoechst 33342

After completion of differentiation induction, an intestinal organoid was incubated with HBSS containing Hoechst 33342 at 37° C. After completion of incubation, the cells were washed with ice-cold PBS to terminate uptake. Incubation was made with PBS warmed to 37° C. for 4 hours to allow Hoechst 33342 to discharge outside the organoid. Thereafter, the fluorescence intensity of the supernatant was measured by use of Synergy HTX microplate reader. After completion of the transportation experiment, the amount of protein was measured. The fluorescence intensity value was corrected based on the amount of protein.

(12) Drug Metabolism Experiment

After completion of differentiation induction, an intestinal organoid was incubated in a culture medium containing 5 μmol/L midazolam (Advanced-DMEM/F12 containing 2 mmol/L L-Glu, 2% B27 supplement, 1% N2 supplement, 100 units/mL penicillin G, 100 μg/mL streptomycin) at 37° C. for 24 hours. Thereafter, the culture medium was sampled. The metabolic activity was determined based on the amount of 1-hydroxymidazolam contained in the medium and measured by a liquid chromatography-mass spectrometer (LC-MS/MS). After completion of the experiment for metabolism, the amount of protein was measured. The metabolic activity was corrected based on the amount of protein.

The marker genes used in this study were a-SMA, ABCB1/MDR1, ABCG2/BCRP, CDX2, Chromogranin A, CYP3A4, E-cad (E-cadherin), Ki67 (expressed in the cells in G1 phase, S phase, G2 phase, M phase; proliferating cell markers), LGR5, Lysozyme, MUC2, Occludin, OLFM4, PXR (pregnane X receptor; nuclear receptor involved in transcriptional regulation of, e.g., CYP3A4), and Sucrase-isomaltase (transmembrane Type II glycoprotein; expressed in the brush border of intestinal epithelial cells), SLC15A1/PEPT1, Villin, and Vim (Vimentin).

2. Results/Consideration (1) Differentiation Induction of Human Intestinal Organoid Using a Polysaccharide Polymer The effect of a polysaccharide polymer to be added at the time of differentiation induction from a human iPS cell to an intestinal organoid was examined. As a result, mRNA expression levels of various pharmacokinetics-related genes such as intestinal tract related genes and CYP3A, in FP001 and FP003 addition groups increased. Particularly, in a FP001 addition group, compared to a control group to which Matrigel (3%) (growth factor was removed) was added, mRNA expressions of many pharmacokinetic-related genes increased (3.7 times in the case of a major drug-metabolizing enzyme, cytochrome P450 (CYP) 3A4; 4.1 times in the case of a peptide uptake transporter, SLC15A1/PEPT1; and 4.5 times in the case of an efflux transporter, ABCB1/MDR1). The mRNA expression levels of markers of cells constituting the intestinal tract, Villin (absorptive epithelial cells), sucrase-isomaltase (brush border of the epithelial cells), MUC2 (goblet cell) and LGR5 (intestinal stem cell) were the same or more to that of the control group (FIG. 14).

(2) Morphological Observation of Human Intestinal Organoid Differentiated by Using a Polysaccharide Polymer Human iPS cell-derived intestinal organoids differentiated by using Matrigel and a polysaccharide polymer had a spherical shape (FIGS. 15A-C). From the results of HE staining, in the human intestinal organoids differentiated by using a polysaccharide polymer, lumen was observed (FIGS. 15D-F).

(3) Immunofluorescent Staining of Human Intestinal Organoid Differentiated by Using a Polysaccharide Polymer Expressions of markers of various cells constituting the intestinal tract (absorptive epithelial cell, intestinal stem cell, goblet cell, intestinal endocrine cell, Paneth cell, mesenchymal cell), an efflux transporter and a tight junction were observed (FIG. 16). Thus, it was suggested that the intestinal organoid is an intestinal tract tissue analog containing these cells.

(4) Function of ABCB1/MDR1 of Human Intestinal Organoid Differentiated by Using Polysaccharide Polymer, Evaluated by Use of Rhodamine 123

Using rhodamine 123, which is a substrate of an efflux transporter, ABCB1/MDR1, and verapamil, which is an inhibitor thereof, the function of ABCB1/MDR1 was evaluated. It was observed that rhodamine 123 is discharged into an intestinal organoid and that transport in the discharge direction was suppressed by verapamil (FIG. 17). From this, it was suggested that a human intestinal organoid differentiated by using a polysaccharide polymer has a function of ABCB1/MDR1.

(5) Function of ABCG2/BCRP in Human Intestinal Organoid Differentiated by Use of a Polysaccharide Polymer, Evaluated by Using Hoechst 33342

Using a substrate of an efflux transporter, ABCG2/BCRP, Hoechst 33342, and an inhibitor thereof, Ko143, the function of ABCG2/BCRP was evaluated. It was observed that Hoechst 33342 is discharged into an intestinal organoid and that transport in the discharge direction was suppressed by Ko143. (FIG. 18). From this, it was suggested that a human intestinal organoid differentiated by using a polysaccharide polymer has a function of ABCG2/BCRP.

(6) Inducibility of CYP3A4 in a Human Intestinal Organoid Differentiated by Using a Polysaccharide Polymer Using a CYP3A inducer, 1α, 25-dihydroxy vitamin $D_3$ (VD3), whether mRNA expression of CYP3A4 is induced or not was investigated. In a VD3 addition group, the mRNA expression of CYP3A4 was significantly induced, compared to a control group (FIG. 19A). In the VD3 addition group, the metabolic activity of midazolam was significantly increased (FIG. 19B), it was confirmed that CYP3A4 is induced at a protein level. From this, it was suggested that the human intestinal organoid differentiated by using a polysaccharide polymer has a drug response to CYP3A4.

(7) CYP3A4 Metabolic Activity of Human Intestinal Organoid Differentiated by Using a Polysaccharide Polymer Using a substrate for CYP3A4, midazolam, and its inhibitor, ketoconazole, CYP3A4 metabolic activity was evaluated. It was confirmed that a human intestinal organoid has midazolam's metabolic activity and that the activity is significantly inhibited by addition of ketoconazole (FIG. 20). Thus, it was suggested that the human intestinal organoid differentiated by using a polysaccharide polymer has CYP3A4's metabolic capacity.

3. Conclusion

As is apparent from the above results, a flotation agent (cohesive material) useful for differentiation of a human iPS cell into an intestinal organoid was newly found in this research. It was also found that the intestinal organoid prepared by the method of the invention has not only a function to transport an efflux transporter but also various pharmacokinetic functions characteristic to the intestinal tract, such as a drug-metabolizing enzyme activity and inducibility. Since FP001 and FP003 are polysaccharide polymers and do not contain any components derived from an animal of another species, these polymers are considered extremely useful as a culture material when an intestinal organoid is used in regenerative medicine.

INDUSTRIAL APPLICABILITY

The present invention makes it possible to prepare an intestinal organoid having a structure close to that of the intestinal tract of a living body. The factors employed in combination in the present invention are low-molecular compounds low in cost and lot-to-lot variability. This feature is extremely important from a practical point of view. According to the present invention, cost for preparing an intestinal organoid is reduced and quality and reliability of an intestinal organoid are improved. The budding intestinal organoid prepared by the present invention are expected to be used in various applications; for example, application to an in-vitro evaluation system (evaluation of medicinal effect, toxicity, pharmacokinetics), preparation of an intestinal tract pathology model such as refractory inflammatory bowel disease, and elucidation of pathogenesis using the model and transplantation to a living body (e.g., humans, experimental animals).

This invention is not limited by the embodiments and Examples of the invention described above. The invention may be modified in various ways within the scope of the claims as long as those skilled in the art can easily conceived. Such modifications are included in the present invention. All the contents of the papers, Patent Publications (Kokai) and Patent Publications disclosed in the specification are incorporated herein by reference.

The invention claimed is:

1. A preparation method for an intestinal tract cell layer from a pluripotent stem cell, comprising the following steps (1) to (6):
   (1) differentiating the pluripotent stem cell into an endoderm-like cell;
   (2) differentiating the endoderm-like cell obtained in step (1) into an intestinal stem cell-like cell;
   (3) culturing the intestinal stem cell-like cell obtained in step (2) in the presence of an epidermal growth factor, a fibroblast growth factor, a TGF β receptor inhibitor, a GSK-3 β inhibitor, and a ROCK inhibitor;
   (4) culturing the cell obtained in step (3) to form a spheroid;
   (5) differentiating the spheroid formed in step (4) to form a small intestinal organoid, wherein the differentiation comprises culturing in the presence of an epidermal growth factor, a BMP inhibitor, and a Wnt signal activator; and
   (6) subjecting the cells constituting the small intestinal organoid formed in step (5) to plane culture carried out in the presence of an epidermal growth factor and a TGF β receptor inhibitor, wherein at least part of the plane culture of step (6) is air-liquid interface culture.

2. The preparation method according to claim 1, wherein the culture of step (6) is carried out in the presence of a cAMP activation substance and a γ-secretase inhibitor in addition to an epidermal growth factor and a TGF β receptor inhibitor.

3. The preparation method according to claim 1, wherein the culture of step (6) is carried out in the presence of a cAMP activation substance and a GSK-3 β inhibitor in addition to an epidermal growth factor and a TGF β receptor inhibitor.

4. The preparation method according to claim 1, wherein the air-liquid interface culture is carried out in the presence of a factor activating a cAMP signal in addition to an epidermal growth factor and a TGFβ receptor inhibitor.

5. The preparation method according to claim 4, wherein the factor is a CAMP derivative, a cAMP-degrading enzyme inhibitor or a cAMP activation substance.

6. The preparation method according to claim 4, wherein the factor is forskolin.

\* \* \* \* \*